(12) United States Patent
Zhang et al.

(10) Patent No.: US 11,771,736 B2
(45) Date of Patent: *Oct. 3, 2023

(54) COMPOSITION COMPRISING A THERAPEUTIC AGENT AND A CXCR4 SELECTIVE ANTAGONIST AND METHODS FOR USING THE SAME

(71) Applicant: Mainline Biosciences (Shanghai) Co., Ltd., Shanghai (CN)

(72) Inventors: Junge Zhang, Malvern, PA (US); Liang Zeng Yan, Carmel, IN (US)

(73) Assignee: Mainline Biosciences (Shanghai) Co., Ltd., Shanghai (CN)

( * ) Notice: Subject to any disclaimer, the term of this patent is extended or adjusted under 35 U.S.C. 154(b) by 339 days.

This patent is subject to a terminal disclaimer.

(21) Appl. No.: 16/766,741

(22) PCT Filed: Dec. 21, 2018

(86) PCT No.: PCT/US2018/067376
§ 371 (c)(1),
(2) Date: May 25, 2020

(87) PCT Pub. No.: WO2019/126796
PCT Pub. Date: Jun. 27, 2019

(65) Prior Publication Data
US 2021/0205407 A1    Jul. 8, 2021

Related U.S. Application Data

(60) Provisional application No. 62/608,653, filed on Dec. 21, 2017.

(51) Int. Cl.
| | | |
|---|---|---|
| *A61K 38/12* | (2006.01) |
| *A61P 35/00* | (2006.01) |
| *A61K 33/243* | (2019.01) |
| *A61K 38/14* | (2006.01) |
| *A61K 38/50* | (2006.01) |
| *A61K 39/395* | (2006.01) |
| *A61K 38/00* | (2006.01) |
| *C07K 7/06* | (2006.01) |
| *A61K 31/255* | (2006.01) |
| *A61K 31/282* | (2006.01) |
| *A61K 31/337* | (2006.01) |
| *A61K 31/475* | (2006.01) |
| *A61K 31/565* | (2006.01) |
| *A61K 31/7048* | (2006.01) |
| *A61K 31/7068* | (2006.01) |

(52) U.S. Cl.
CPC ............ *A61K 38/12* (2013.01); *A61K 33/243* (2019.01); *A61K 38/00* (2013.01); *A61K 38/14* (2013.01); *A61K 38/50* (2013.01); *A61K 39/3955* (2013.01); *A61P 35/00* (2018.01); *C07K 7/06* (2013.01); *A61K 31/255* (2013.01); *A61K 31/282* (2013.01); *A61K 31/337* (2013.01); *A61K 31/475* (2013.01); *A61K 31/565* (2013.01); *A61K 31/7048* (2013.01); *A61K 31/7068* (2013.01)

(58) Field of Classification Search
CPC ................................ A61K 38/12; A61P 35/00
See application file for complete search history.

(56) References Cited

U.S. PATENT DOCUMENTS

| | | | | |
|---|---|---|---|---|
| 10,351,601 | B2 * | 7/2019 | Zhang | A61P 29/00 |
| 10,870,681 | B2 * | 12/2020 | Zhang | A61P 29/00 |
| 11,123,437 | B2 * | 9/2021 | Zhang | C07K 7/06 |

* cited by examiner

*Primary Examiner* — Kevin E Weddington
(74) *Attorney, Agent, or Firm* — Don D. Cha; HDC Intellectual Property Law, LLP

(57) ABSTRACT

The present invention provides a composition comprising a therapeutic agent and a C-X-C chemokine receptor type 4 (CXCR4) antagonist, and methods for using the same. Compositions and methods of the invention can be used to treat cancer, viral infection, immune disorders (e.g., rheumatoid arthritis), pulmonary fibrosis, or any other clinical condition associated with abnormal expression (e.g., overexpression and/or upregulation) of CXCR4. Compounds of the invention can also be used in stem cell therapeutics.

16 Claims, 6 Drawing Sheets

Specification includes a Sequence Listing.

COMPOSITION COMPRISING A THERAPEUTIC AGENT AND A CXCR4 SELECTIVE ANTAGONIST AND METHODS FOR USING THE SAME

CROSS-REFERENCE TO RELATED APPLICATIONS

This application claims the priority benefit of U.S. Provisional Application No. 62/608,653, filed Dec. 21, 2017, which is incorporated herein by reference in its entirety.

FIELD OF THE INVENTION

The present invention relates to a composition comprising a therapeutic agent and a C-X-C chemokine receptor type 4 (CXCR4) antagonist, and methods for using the same in treating cancer. Compositions and methods of the invention can be used to treat cancer, viral infection, immune disorders (e.g., rheumatoid arthritis), pulmonary fibrosis, or any other clinical condition associated with abnormal expression (e.g., overexpression and/or upregulation) of CXCR4. Compounds of the invention can also be used in stem cell therapeutics.

BACKGROUND OF THE INVENTION

Cancer is a group of diseases involving abnormal cell growth with the potential to invade or spread to other parts of the body. There are more than 100 types of cancer that affect human beings. In 2016, there were an estimated 1,685,210 new cancer cases diagnosed and 595,690 cancer deaths in the U.S. alone (Cancer Statistics 2016—American Cancer Society, Inc.). Cancer is one of the most heterogeneous diseases. While multiple molecularly targeted agents have been an important area of investigational clinical research, a combination of therapeutic agents of different pharmacological mechanisms provides an important potential solution to meet those increasing needs for new and novel therapies for fighting cancers.

Studies have shown CXCL12 (also called stromal cell-derived factor-1 or SDF-1) and CXCR4, a chemokine and chemokine receptor pair play important roles in hematopoiesis, multiple stages of tumorigenesis, and embryonic development (Broxmeyer, H. E. et al., *Int. J. Hematol.* 2001, 74, 9-17; Horuk, R., *Nat. Rev. Drug Discov.* 2009, 8, 23-33). For example, activation of CXCR4 by CXCL12 has shown to direct leukocyte chemotaxis in the immune system in response to inflammation and progenitor cell migration during embryologic development. Activation of CXCR4 by CXCL12 has also been shown to mediate signaling pathway that is involved in breast cancer metastasis and memory T cell migration (Orimo, A., et al., *Cell* 2005, 121, 335-348).

CXCR4, a G-protein-coupled receptor also known as fusin or CD184 (cluster of differentiation 184), is constitutively- or over-expressed in a wide variety of human cancers, promoting local tumor cell proliferation, survival and angiogenesis (Huang, E. H., et al., *J. Surg. Res.* 2009, 155, 231-236). It has also been reported that CXCR4 is a co-receptor for HIV entry and infection of host cells and has been evaluated as a potential HIV therapy (Tamamura, H., et al., *Biochem. Biophys. Res. Commun.* 1998, 253, 877-882; Oberlin, E. et al., *Nature,* 1996, 382, 833-835).

Research by the present inventors in this area has led to several patent applications, including commonly assigned U.S. patent application Ser. No. 15/695,862, filed Sep. 5, 2017, and U.S. Provisional Patent Application No. 62/554,354, filed Sep. 5, 2017, all of which are incorporated herein by reference in their entirety.

Various studies have suggested that activation of the CXCR4-CXCL12 signaling pathway is a potential mechanism of resistance to many cytotoxic cancer therapies, rendering a much reduced and compromised therapeutic outcome of therapeutic interventions (D. G. Duda, et al., *Clin. Cancer Res.* 2011, 17(8), 2074-80). It has been shown that certain chemotherapeutics (e.g., paclitaxel) or vascular-disrupting agents rapidly increased both circulating CXCL12 levels and the mobilization of bone marrow-derived cells expressing CXCR4, including CD11b$^+$ myelo-monocytes, endothelial precursor cells, and hemangiocytes. See, for example, Y. Shaked, et al., *Cancer Cell* 2008, 14, 263-73 and Y. Shaked, et al, *Cancer Res.* 2009, 69, 7524-28. Therefore, inhibition of the CXCR4-CXCL12 signaling pathway may provide an effective method (i) to sensitize tumor cells to traditional and newer biological cancer therapies and/or (ii) to reduce chemotherapy resistance in tumor cells.

In recent years, immunotherapy has become one of the most important advances in cancer treatment. However, it has not achieved the status of being a panacea toward the diverse cancer diseases. For example, patients with pancreatic ductal adenocarcinoma (PDA) had no significant responses to cytotoxic T-lymphocyte associated protein-4 antibody (anti($\alpha$)-CTLA-4) or antibodies to the programed cell death 1/programmed cell death 1 ligand 1(PD-1/PD-L1) receptor/ligand pair (R. E. Royal, et al., *J Immunother* 2010, 33(8), 828-33; J. R. Brahmer, et al., *N Engl, J Med* 2012, 366(26), 2455-65). However, immune control of PDA growth was achieved by depleting carcinoma-associated fibroblasts (CAFs) that express fibroblast activation protein (FAP), which restored the antitumor effects of $\alpha$-CTLA-4 and $\alpha$-PD-L1 (C Feig, et al., PNAS, 2013, 110(50), 20212-17). Without being bound by any theory, it is believed that the immune suppressive activity accounts for the failure of these T-cell checkpoint antagonists. Further investigations suggested that chemokine (C-X-C motif) ligand 12 (CXCL12) explained the overriding immunosuppression by the FAP$^+$ cell: T cells were absent from regions of the tumor containing cancer cells; cancer cells were coated with the chemokine, CXCL12; and the FAP$^+$ CAF was the principal source of CXCL12 in the tumor. Based at least on these observations, the present inventors discovered that administration of a CXCR4 inhibitor can induce rapid T-cell accumulation among cancer cells and act synergistically with $\alpha$-PD-L1 antibody or other immunotherapy to greatly diminish cancer cells.

While using a combination of multiple compounds for treatment of cancer and viral infections are known in the art, there still remains a need for other combination therapies for more effective treatment of cancer and viral infections.

SUMMARY OF THE INVENTION

Some aspects of the invention provide a composition comprising (i) a therapeutic agent (i.e., a drug, preferably a Food and Drug Administration (i.e., US FDA) approved drug) and (ii) a CXCR4 antagonist of the formula:

(SEQ ID NO: 1)

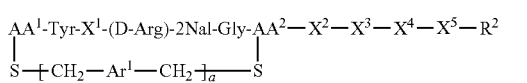

or a pharmaceutically acceptable salt thereof, wherein
a is 0 or 1;
$AA^1$ along with the sulfur atom that is attached thereto is 3-mercaptopropionic acid, optionally substituted cysteine, or optionally substituted homocysteine;
$AA^2$ along with the sulfur atom that is attached thereto is cysteine or homocysteine;
$Ar^1$ is an optionally substituted aryl;
$X^1$ is Arg, Dap, Dab, Orn, Lys, Dap(iPr), Dab(iPr), Orn (iPr), or Lys(iPr);
$X^2$ is Arg, Dap, Dab, Orn, Lys, Dap(iPr), Dab(iPr), Orn (iPr), Lys(iPr), D-Arg, D-Dap, D-Dab, D-Orn, D-Lys, D-Dap(iPr), D-Dab(iPr), D-Orn(iPr), D-Lys(iPr), or absent;
$X^3$ is Lys, Gly or absent, preferably $X^3$ is Gly or absent;
$X^4$ is Lys, Phe, 2Nal, 1Nal, a D-isomer thereof, Gly or absent, preferably $X^4$ is Phe, 2Nal, 1Nal, a D-isomer thereof, or absent;
$X^5$ is Lys, Gly or absent, preferably $X^5$ is Gly or absent;
$R^2$ is —$OR^4$ or —$NHR^5$;
$R^4$ is H or alkyl; and
$R^5$ is H, alkyl, optionally substituted aryl, optionally substituted aralkyl.

In some embodiment, the therapeutic agent is a chemotherapeutic agent that is useful in treating a cancer. Still in another embodiments, the chemotherapeutic agent is selected from the group consisting of Altretamine; Asparaginase; Bleomycin; Busulfan; Carboplatin; Carmustine; Chlorambucil; Cisplatin; Cladribine; Cyclophosphamide; Cytarabine; Dacarbazine; Diethylstilbestrol; Ethinyl; estradiol; Etoposide; Mitomycin; Mitotane; Mitoxantrone; Paclitaxel; Pentastatin; Pipobroman; Plicamycin; Prednisone; Procarbazine; Streptozocin; Tamoxifen; Teniposide; Vinblastine; Vincristine; and a combination thereof.

Yet in another embodiment, the therapeutic agent is an antibody. Exemplary antibodies that can be used in compositions of the invention include, but are not limited to, pembrolizumab, tremelimumab, ipilimumab, nivolumab, pidilizumab, durvalumab, atezolimab, trastuzumab, bevacizumab, cetuximab, panitumumab, rituximab, alemtuzumab, ofatumumab, gemtuzumab, brentuximab, and a combination thereof.

Still in other embodiments, the therapeutic agent is an antiviral agent. Exemplary antiviral agents that are useful in the compositions and methods of the invention include, but are not limited to, abacavir, atazanavir, cobicistat, darunavir, didanosine, dolutegravir, efavirenz, elvitegravir, emtricitabine, enfuvirtide, fosamprenavir, hydroxychloroquine sulfate, indinavir, lamivudine, lopinavir, maraviroc, nelfinavir, raltegravir, ritonavir, saquinavir, stavudine, tenofovir disoproxil fumarate, tipranavir, zidovudine, and a combination thereof.

Compositions and methods of the invention can also be used to treat immune disorders (e.g., rheumatoid arthritis), pulmonary fibrosis, or any other clinical condition associated with abnormal expression (e.g., overexpression and/or upregulation) of CXCR4.

Compounds of the invention can also be used in stem cell therapeutics.

BRIEF DESCRIPTION OF THE DRAWINGS

FIG. 1 is an assay data showing several MLB peptides were able to inhibit the ligand (SDF-1α)-induced cell migration in the TNBC MDA-MB-231 cells. The green colors at 0 hr indicate the initial scratch area; at 12 or 16 hr, green colors indicate the remaining areas without cell migrating to.

FIG. 3 is an assay data showing that MLB peptides also inhibit SDF-1α-induced HCC1806 cell migration. The green colors at 0 hr indicate the initial scratch area; at 12 hr, green colors indicate the remaining areas without cell migrating to.

DETAILED DESCRIPTION OF THE INVENTION

Figure 1:
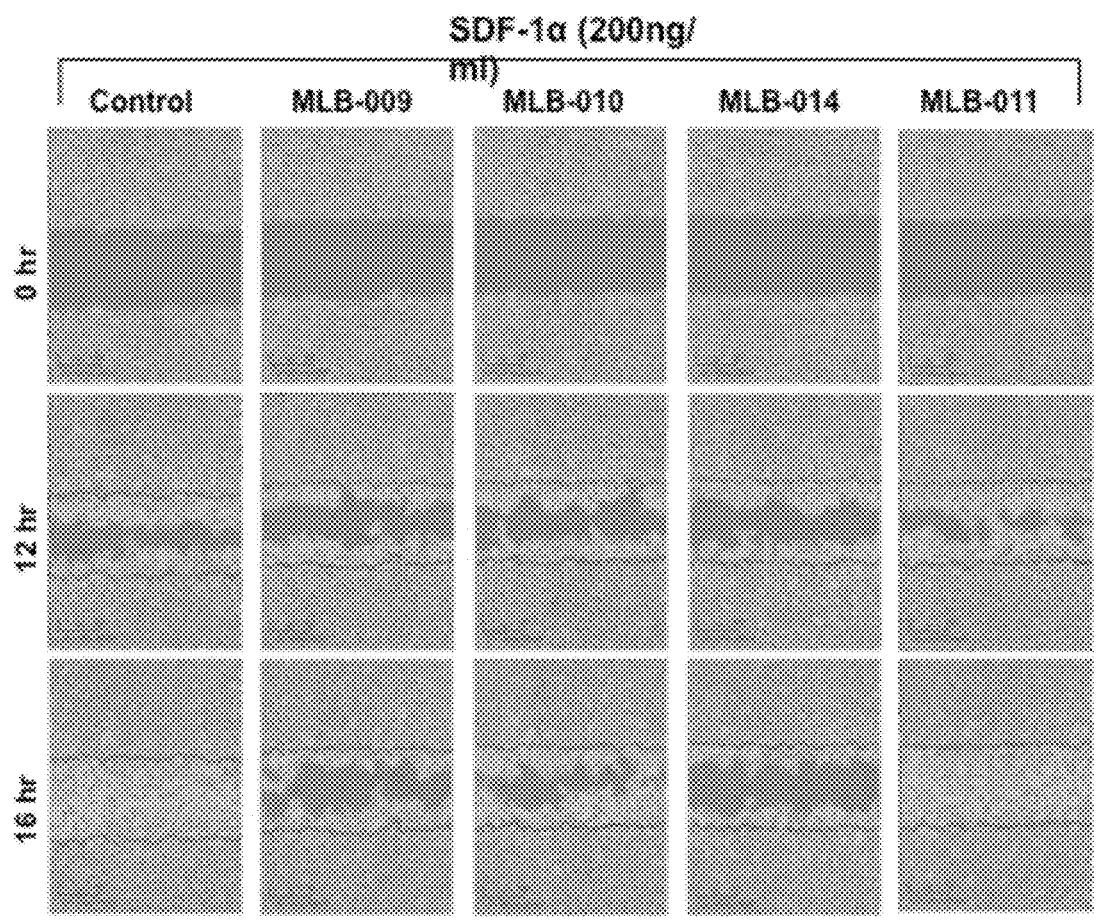

Definitions: The term "alkyl" refers to a saturated linear monovalent hydrocarbon moiety of one to eighteen, typically one to twelve, and often one to six, carbon atoms or a saturated branched monovalent hydrocarbon moiety of three to eighteen, typically three to twelve and often three to six, carbon atoms. Exemplary alkyl group include, but are not limited to, methyl, ethyl, n-propyl, 2-propyl, tert-butyl, iso-butyl, pentyl, neo-pentyl, octyl, dodeclyl, octadecyl and the like.

The term "acyl" refers to a moiety of the formula —C(=O)—$R^a$, where $R^a$ is alkyl as defined herein.

The term "aryl" refers to a monovalent mono-, bi- or tricyclic aromatic hydrocarbon moiety of six to twenty-four ring atoms. Exemplary aryl groups include, but are not limited to, phenyl, naphth-1-yl, naphth-2-yl, anthracenyl, etc. The term "optionally substituted aryl" means the aryl group can optionally be substituted with one or more, preferably one, two, or three, substituents within the ring structure. When two or more substituents are present in an aryl group, each substituent is independently selected. Exemplary substituents of aryl group include, but are not limited to, alkyl, haloalkyl, heteroalkyl, halo, nitro, cyano, acyl, carboxylic acid and the esters (e.g., —$CO_2R$, where R is H or alkyl) and amides thereof, etc.

The terms "halo," "halogen" and "halide" are used interchangeably herein and refer to fluoro, chloro, bromo, or iodo.

"Haloalkyl" means an alkyl group as defined herein in which one or more hydrogen atom is replaced by same or different halides. The term "haloalkyl" also includes perhalogenated alkyl groups in which all alkyl hydrogen atoms are replaced by halogen atoms. Exemplary haloalkyl groups include, but are not limited to, —$CH_2Cl$, —$CF_3$, —$CH_2CF_3$, —$CH_2CCl_3$, and the like.

"Heteroalkyl" means a saturated alkyl moiety containing carbon, hydrogen and one or more heteroatoms in place of a carbon atom, or optionally one or more heteroatom-containing substituents independently selected from =O, —OR$^a$, —C(O)R$^a$, —NR$^b$R$^c$, —C(O)NR$^b$R$^c$ and —S(O)$_n$R$^d$ (where n is an integer from 0 to 2). R$^a$ is hydrogen, alkyl, haloalkyl, or acyl. Each of R$^b$ and R$^c$ is independently hydrogen or alkyl.

"Aralkyl" refers to a moiety of the formula —R$^b$R$^c$ where R$^b$ is an alkylene group and R$^c$ is an aryl group as defined herein. The term "optionally substituted aralkyl" means the aryl group (i.e., R$^c$ moiety) is optionally substituted aryl as defined herein. Exemplary aralkyl groups include, but are not limited to, benzyl, benzyl group in which the phenyl group is optionally substituted, and the like.

"Alkylene" refers to a saturated linear divalent hydrocarbon moiety of one to eighteen, preferably one to twelve, and more preferably one to eight carbon atoms or a branched saturated divalent hydrocarbon moiety of three to eighteen, preferably three to twelve, and more preferably three to eight, carbon atoms. Exemplary alkylene groups include, but are not limited to, methylene, ethylene, propylene, butylene, pentylene, and the like.

"Pharmaceutically acceptable excipient" refers to an excipient that is useful in preparing a pharmaceutical composition that is generally safe, non-toxic and neither biologically nor otherwise undesirable, and includes excipient that is acceptable for veterinary use as well as human pharmaceutical use.

"Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethane-sulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Protecting group" refers to a moiety, except alkyl groups, that when attached to a reactive group in a molecule masks, reduces or prevents that reactivity. Examples of protecting groups can be found in T. W. Greene and P. G. M. Wuts, *Protective Groups in Organic Synthesis*, 3$^{rd}$ edition, John Wiley & Sons, New York, 1999, and Harrison and Harrison et al., *Compendium of Synthetic Organic Methods*, Vols. 1-8 (John Wiley and Sons, 1971-1996), which are incorporated herein by reference in their entirety. Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like.

"Corresponding protecting group" means an appropriate protecting group corresponding to the heteroatom (i.e., N, O, P or S) to which it is attached.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

As used herein, the term "treating", "contacting" or "reacting" refers to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

"$K_i$" values are calculated using IC$_{50}$ values determined in the CXCR4/$^{125}$I-SDF-1α binding assay described below by employing equation 7.22 of *Enzymes, A Practical Introduction to Structure, Mechanism, and Data Analysis*, Robert A. Copeland, Wiley-VCH, New York, 1996, page 207.

The term "SDF-1" includes two isoforms, SDF-1α and SDF-1β, currently understood to exhibit similar functionality.

As used herein, the terms "those defined above" and "those defined herein" when referring to a variable incorporates by reference the broad definition of the variable as well as preferred, more preferred and most preferred definitions, if any.

As used herein "a clinical condition associated with activity of CXCR4" means any disease or abnormal condition in a subject due to overexpression, activation and/or upregulation of CXCR4 or any disease or abnormal clinical condition that can be treated by a compound of the invention. For example, CXCR4 is functionally expressed or overexpressed in a variety of solid and hematological malignancies, including lymphoma and chronic lymphocytic leukemia. Inhibition of CXCR4 by a CXCR4 antagonist can potentially offer a viable treatment for those patients.

The term "therapeutic agent" refers to any molecule or compound that can be used to treat a clinical condition. In some embodiments, clinical conditions that are treated using compositions and/or methods of the invention include clinical conditions associated with overexpression and/or upregulation of CXCR4 or microorganism infections (e.g., bacteria, virus, fungus, etc.) that utilize CXCR4. Exemplary therapeutic agents include, small molecules, peptides, nucleotides, small interfering RNAs (siRNAs), aptamers, antibodies, etc. Typically, a therapeutic agent refers to drugs that have been or are in the process of being or will be developed and approved by the U.S. Food and Drug Administration ("US FDA" or "FDA") for treatment of various clinical conditions, in particular clinical conditions associated with overexpression and/or upregulation of CXCR4 or microorganism infections and other clinical conditions as disclosed or contemplated herein.

The term "chemotherapeutic agent" refers to any molecule or compound that is known or is being developed or will be developed for treatment of a cancer. Exemplary chemotherapeutic agents include, small molecules (e.g., conventional cancer drugs), peptides, nucleotides, small interfering RNAs (siRNAs), aptamers, antibodies, etc.

The term "antiviral agent" refers to any molecule or compound that is capable of treating a viral infection. Exemplary viral infections that can be treated using compositions and methods of the invention include, but are not limited to, human immunodeficiency viral (HIV) infection.

Compounds of the invention: Some aspects of the invention provide a CXCR4 antagonist of the formula:

(SEQ ID NO: 1)

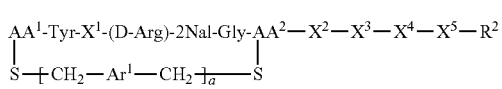

I or a pharmaceutically acceptable salt thereof, where a is 0 or 1; $AA^1$ along with the sulfur atom that is attached thereto is 3-mercaptopropionic acid, optionally substituted cysteine, or optionally substituted homocysteine; $AA^2$ along with the sulfur atom that is attached thereto is cysteine or homocysteine; $Ar^1$ is an optionally substituted aryl; $X^1$ is Arg, Dap, Dab, Orn, Lys, Dap(iPr), Dab(iPr), Orn(iPr), or Lys(iPr); $X^2$ is Arg, Dap, Dab, Orn, Lys, Dap(iPr), Dab(iPr), Orn(iPr), Lys(iPr), D-Arg, D-Dap, D-Dab, D-Orn, D-Lys, D-Dap(iPr), D-Dab(iPr), D-Orn(iPr), D-Lys(iPr), or absent; $X^3$ is Gly or absent; $X^4$ is Phe, 2Nal, 1Nal, or absent; $X^5$ is Gly or absent; and $R^2$ is —$OR^4$ or —$NHR^5$, wherein $R^4$ is H or alkyl; and $R^5$ is H, alkyl, optionally substituted aryl, optionally substituted aralkyl. In one particular embodiment, CXCR4 antagonist of the invention are of the formula:

(SEQ ID NO:2)

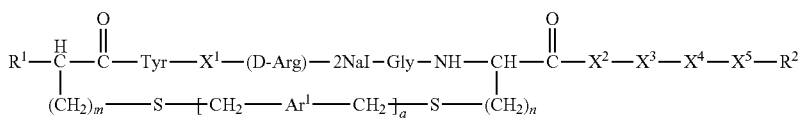

IA or a pharmaceutically acceptable salt thereof, wherein: a is an integer 0 or 1; m and n are independently 1 or 2; $Ar^1$ is an optionally substituted aryl; $R^1$ is H or $NHR^3$, wherein $R^3$ is H, $C_{2-18}$ alkyl, $C_{2-18}$ acyl, optionally substituted $C_{6-24}$ aryl, or a moiety of the formula —$[C(=O)]_a$—$[R^{1a}]_b$ $Ar^{1a}$, where a and b is either 0 or 1, provided at least one of a or b is 1, $R^{1a}$ is alkylene and $Ar^{1a}$ is optionally substituted aryl; $X^1$ is Arg, Dap, Dab, Orn, Lys, Dap(iPr), Dab(iPr), Orn(iPr), or Lys(iPr); $X^2$ is Arg, Dap, Dab, Orn, Lys, Dap(iPr), Dab(iPr), Orn(iPr), Lys(iPr), D-Arg, D-Dap, D-Dab, D-Orn, D-Lys, D-Dap(iPr), D-Dab(iPr), D-Orn(iPr), D-Lys(iPr), or absent; $X^3$ is Gly, Lys, Lys(acyl), or absent; $X^4$ is Phe, 2Nal, 1Nal, or a (D)-isomer thereof, or absent; $X^5$ is Gly or absent; and $R^2$ is OH or $NHR^4$, wherein $R^4$ is H, $C_{1-18}$ alkyl, optionally substituted $C_{6-24}$ aryl or optionally substituted aralkyl.

It should be appreciated that when m is 1, and $R^1$ is —$NH_2$, the left terminal amino acid group in compound of Formula IA is cysteine, whereas when m is 2 and $R^1$ is —$NH_2$, the left terminal amino acid group in compound of Formula IA is homocysteine ("hCys"). Similarly, when n is 1, the amino acid group is cysteine and when n is 2 the amino acid group is homocysteine. When $R^1$ is H and m is 1, the corresponding amino acid moiety, i.e., the moiety of the formula —S—$CH_2CH(R^1)$—C(=O)—, is 3-mercaptopropionic acid moiety.

Throughout this disclosure any amino acid residue, unless explicitly stated, can be either (L)-isomer or (D)-isomer. In addition, both natural and unnatural amino acids are described in three letter codes, which are well known to one skilled in the art. For example, Dap refers to diaminopropionic acid, Dab refers to 2,4-diamino butyric acid, and Orn refers to ornithine, etc. In addition, a substituent that is present in the side-chain functional group of the amino acid residue is indicated by a parenthesis. Thus, Lys(iPr) refers to lysine in which the amine functional group on the side-chain of lysine is substituted with an iso-propyl group. Similarly, Lys(acyl) refers to lysine in which the amine functional group on the side-chain of lysine is substituted with (i.e., attached to) an acyl group (—C(=O)$CH_3$). 2Nal refers to 3-(2-naphthyl)-alanine and 1Nal refers to 1-naphthylalanine. Furthermore, amino acids are generally shown left to right from amino-terminal end to carboxy-terminal end. Amino acid residues within the brackets "[ ]" are within the cyclic structure and groups external to the brackets are outside the cyclized ring.

In some embodiments, $X^1$ is an (L)-isomer amino acid. Yet in other embodiments, $X^2$ can be either (L)- or (D)-isomer or absent. In one particular embodiment, $X^2$ is a (D)-isomer amino acid or absent, i.e., $X^2$ is D-Dab, D-Orn, D-Lys, D-Dap(iPr), D-Dab(iPr), D-Orn(iPr), D-Lys(iPr), or absent. Still in other embodiments, $X^2$ is an (L)-isomer amino acid. Still yet in other embodiments, $X^3$ is an (L)-isomer amino acid. In further embodiments, $X^4$ is an (L)-isomer. Yet still in other embodiments, $X^5$ is an (L)-isomer.

Still in other embodiments, $X^4$ is a (D)-isomer or absent, i.e., D-Phe, D-2Nal, D-1Nal, or absent.

Yet in other embodiments, $R^3$ is H, $C_{2-18}$ alkyl, $C_{2-18}$ acyl, optionally substituted $C_{6-24}$ aryl, optionally substituted benzyl, optionally substituted benzoyl.

Still yet in other embodiments, $R^2$ is OH or $NHR^5$, wherein $R^5$ is H, $C_{1-18}$ alkyl, $C_{6-24}$ optionally substituted aryl or optionally substituted benzyl.

In one particular embodiment, the pharmaceutically acceptable salt is an acetic acid salt or a hydrochloric acid salt.

Still in another particular embodiment, 10 is hydrogen and m=1.

Yet in another particular embodiment, $R^2$ is —NH(Et) and $X^4$ and $X^5$ are absent.

In some embodiments, Ar¹ is phenyl or naphthyl, i.e., a moiety of the formula:

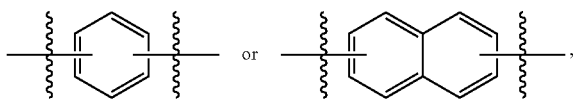

respectively.

The —CH₂— groups can be substituted at 1,2-, 1,3-, 1,4- of the phenyl group or 1,2-, 1,3-, 1,4-, 1,5-, 1,6-, 1,7-, 1,8-, 2,3-, 2,4-, etc. position of the naphthyl group. Typically, Ar¹ is phenyl. In one particular embodiment Ar¹ is 1,2-substituted phenyl, i.e., the —CH₂— groups are substituted at 1,2- positions relative to each other.

Yet in some embodiments, $R^3$ is H, $C_{2-18}$ acyl (i.e., a moiety of the formula —C(=O)—$R^{1b}$, where $R^{1b}$ is $C_{1-17}$ alkyl), or a moiety of the formula —[C(=O)]$_a$—[$R^{1a}$]$_b$—$Ar^{1b}$, where a and b is either 0 or 1, provided at least one of a or b is 1, $R^{1a}$ is alkylene and $Ar^{1a}$ is optionally substituted aryl. In some embodiments, $R^3$ is optionally substituted benzyl or optionally substituted benzoyl. It should be understood that the term "optionally substituted" when referring to aralkyl, benzyl, or benzoyl, means the aromatic moiety is optionally substituted.

Still in other embodiments, $R^4$ is optionally substituted aralkyl. In one particular embodiment, $R^4$ is optionally substituted benzyl.

Some of the specific compounds of the invention include, but are not limited to, products and intermediates in Examples 1-23, such as cyclo[Mpa-Tyr-Lys(iPr)-(D-Arg)-2Nal-Gly-Cys]-Lys(iPr)-Gly-NH(Et) (SEQ ID NO:3); cyclo[Mpa-Tyr-Lys(iPr)-(D-Arg)-2Nal-Gly-Cys]-Lys(iPr)-Gly-NH₂ (SEQ ID NO:4); Ac-cyclo[hCys-Tyr-Lys(iPr)-(D-Arg)-2Nal-Gly-Cys]-Lys(iPr)-Gly-NH₂ (SEQ ID NO:5); Ac-cyclo[hCys-Tyr-Lys(iPr)-(D-Arg)-2Nal-Gly-Cys]-Lys(iPr)-Gly-NH(Et) (SEQ ID NO:6); and compounds of the formulas:

(SEQ ID NO:7)

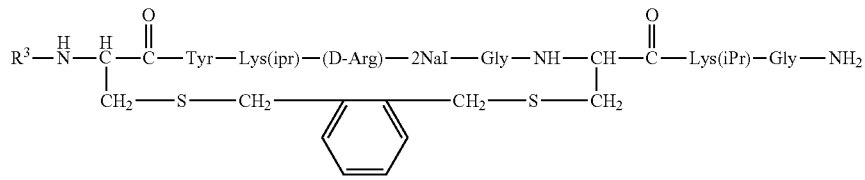

(where $R^3$ is acyl, i.e., a moiety of the formula —C(=O)CH₃, or benzoyl, i.e., a moiety of the formula —C(=O)Ph), (SEQ ID NO:8)

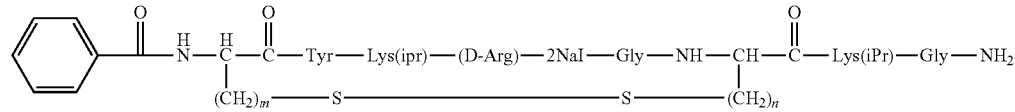

(where m=1 and n=2; and where m=2 and n=1);

(SEQ ID NO:9)

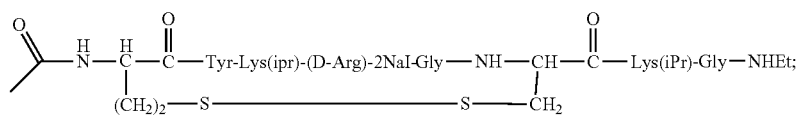

(SEQ ID NO:10)

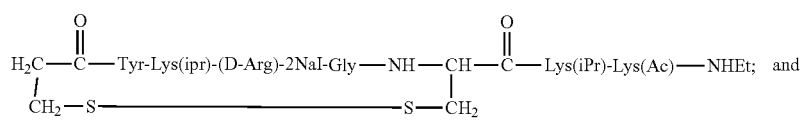

and (SEQ ID NO:11)

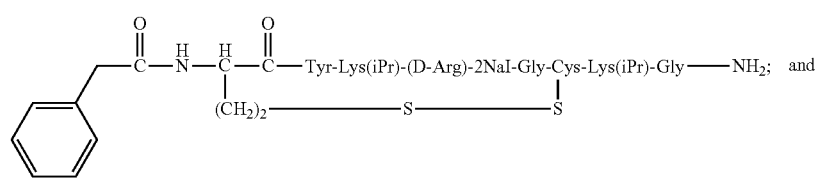

and and a pharmaceutically acceptable salt thereof. It should be appreciated that compound of the formula:

(SEQ ID NO:11)

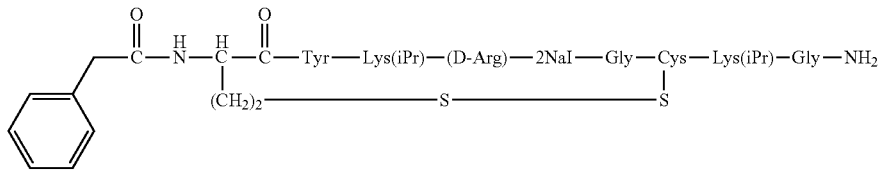

can also be presented as having the following structure:

(SEQ ID NO:11)

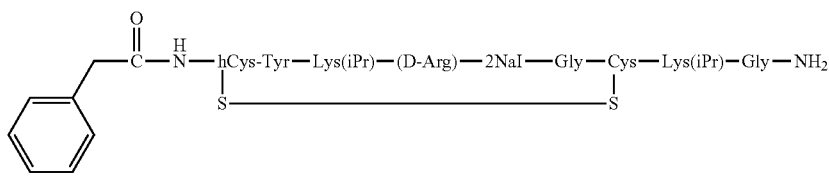

Similarly, compound of the formula:

(SEQ ID NO:10)

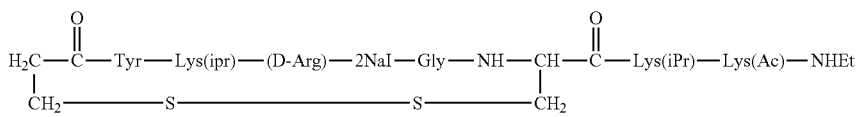

can also be represented by the following formulas:

(SEQ ID NO:10)

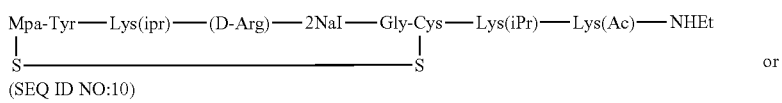

(SEQ ID NO:10)

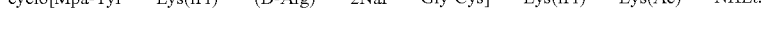

Still further, combinations of the particular embodiments described herein can form other embodiments. For example, in one particular embodiment $R^1$ is hydrogen, m is 1, $R^2$ is —NH(Et) and $X^4$ and $X^5$ are absent. In this manner, a variety of compounds are embodied within the present invention.

As illustrated above, the term "cyclo" in compounds listed above indicates where the cyclic bond is present. Thus, for example, in compound Ac-cyclo[hCys-Tyr-Lys(iPr)-(D-Arg)-2Nal-Gly-Cys]-Lys(iPr)-Gly-NH$_2$ (SEQ ID NO:9), the cyclic bond (e.g., the disulfide bond) is present between the homocysteine sulfur atom and the cysteine sulfur atom. This compound can also be represented by the following formula:

(SEQ ID NO:9)

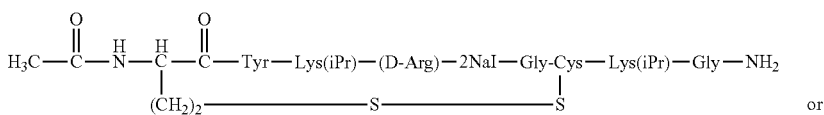

-continued (SEQ ID NO:9)

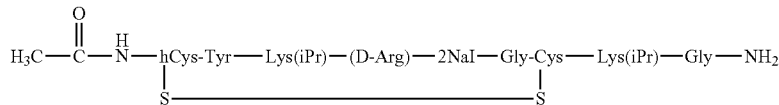

where the —OH group of the carboxyl terminal of the glycine is replaced with an —NH$_2$ group.

Unless otherwise stated, all amino acid chains are written in a conventional form, that is in the direction of amino terminal to carboxyl terminal direction going from left to right.

Pharmaceutical Composition: In another aspect, the present invention provides a pharmaceutical composition comprising a compound of Formula I and/or pharmaceutically acceptable salt thereof. The pharmaceutical composition can also include a pharmaceutically acceptable carrier, diluent, or excipient.

The present invention includes pharmaceutical compositions comprising at least one compound of the invention and/or a pharmaceutically acceptable salt or solvate thereof, together with at least one pharmaceutically acceptable carrier, and optionally a diluent, excipient, and/or other therapeutic and/or prophylactic ingredients.

In general, the compounds of the invention are administered in a therapeutically effective amount by any of the accepted modes of administration for agents that serve similar utilities. Suitable dosage ranges are typically 1-500 mg daily, typically 1-100 mg daily, and often 1-30 mg daily, depending on numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases is typically able, without undue experimentation and in reliance upon personal knowledge and the disclosure of this application, to ascertain a therapeutically effective amount of the compounds of the invention.

Compounds of the invention are administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. Typical manner of administration is generally oral using a convenient daily dosage regimen which can be adjusted according to the degree of affliction. However, in some instances, e.g., for treatment of a cancer or rheumatoid arthritis, compounds of the invention can be injected directly at the site of cancer cells or rheumatoid arthritis.

A compound or compounds of the invention, together with one or more conventional adjuvants, carriers, or diluents, can be placed into the form of pharmaceutical compositions and unit dosages. The pharmaceutical compositions and unit dosage forms can be comprised of conventional ingredients in conventional proportions, with or without additional active compounds or principles, and the unit dosage forms can contain any suitable effective amount of the active ingredient commensurate with the intended daily dosage range to be employed. The pharmaceutical compositions can be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention can be formulated in a wide variety of oral administration dosage forms. The pharmaceutical compositions and dosage forms can comprise a compound or compounds of the invention or pharmaceutically acceptable salts thereof as the active component. The pharmaceutically acceptable carriers can be either solid or liquid. Solid form preparations include powders, tablets, pills, capsules, cachets, suppositories, and dispersible granules. A solid carrier can be one or more substances which can also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges can be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions can be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well-known suspending agents. Solid form preparations include solutions, suspensions, and emulsions, and can contain, in addition to the active component, colorants, flavors, stabilizers, buffers, artificial and natural sweeteners, dispersants, thickeners, solubilizing agents, and the like.

The compounds of the invention can also be formulated for parenteral administration (e.g., by injection, for example bolus injection or continuous infusion or direct injection at the site of treatment) and can be presented in unit dose form in ampoules, pre-filled syringes, small volume infusion or in multi-dose containers with an added preservative. The compositions can take such forms as suspensions, solutions, or emulsions in oily or aqueous vehicles, for example solutions in aqueous polyethylene glycol. Examples of oily or non-aqueous carriers, diluents, solvents or vehicles include propylene glycol, polyethylene glycol, vegetable oils (e.g., olive oil), and injectable organic esters (e.g., ethyl oleate), and can contain formulatory agents such as preserving, wetting, emulsifying or suspending, stabilizing and/or dispersing agents. Alternatively, the active ingredient can be in powder form, obtained by aseptic isolation of sterile solid or by lyophilization from solution for constitution before use with a suitable vehicle, e.g., sterile, pyrogen-free water.

The compounds of the invention can be formulated for topical administration to the epidermis as ointments, creams or lotions, or as a transdermal patch. Ointments and creams can, for example, be formulated with an aqueous or oily base with the addition of suitable thickening and/or gelling agents. Lotions can be formulated with an aqueous or oily base and will in general also contain one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the invention can be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention can also be formulated for vaginal administration. Pessaries, tampons, creams, gels, pastes, foams or sprays containing in addition to the active ingredient such carriers as are known in the art to be appropriate.

The compounds of the invention can be formulated for nasal administration. The solutions or suspensions are applied directly to the nasal cavity by conventional means, for example, with a dropper, pipette or spray. The formulations can be provided in a single or multidose form. In the latter case of a dropper or pipette, this can be achieved by the patient administering an appropriate, predetermined volume of the solution or suspension. In the case of a spray, this can be achieved for example by means of a metering atomizing spray pump.

The compounds of the invention can be formulated for aerosol administration, particularly to the respiratory tract and including intranasal administration. The compound will generally have a small particle size for example of the order of five (5) microns or less. Such a particle size can be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol can conveniently also contain a surfactant such as lecithin. The dose of drug can be controlled by a metered valve. Alternatively the active ingredients can be provided in a form of a dry powder, for example, a powder mix of the compound in a suitable powder base such as lactose, starch, starch derivatives such as hydroxypropylmethyl cellulose and polyvinylpyrrolidine (PVP). The powder carrier typically forms a gel in the nasal cavity. The powder composition can be presented in unit dose form, for example, in capsules or cartridges of e.g., gelatine or blister packs from which the powder can be administered by means of an inhaler.

When desired, formulations can be prepared with enteric coatings adapted for sustained or controlled release administration of the active ingredient. For example, the compounds of the invention can be formulated in transdermal or subcutaneous drug delivery devices. These delivery systems are advantageous when sustained release of the compound is necessary or desired and when patient compliance with a treatment regimen is crucial. Compounds in transdermal delivery systems are frequently attached to a skin-adhesive solid support. The compound of interest can also be combined with a penetration enhancer, e.g., Azone (1-dodecylazacycloheptan-2-one). Sustained release delivery systems can be inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are typically in unit dosage forms. In such form, the preparation is often subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington: *The Science and Practice of Pharmacy* 1995, edited by E. W. Martin, Mack Publishing Company, 19th edition, Easton, Pa.

When it is possible that, for use in therapy, therapeutically effective amounts of a compound of Formula I, as well as pharmaceutically acceptable salts thereof, can be administered as the raw chemical, it is possible to present the active ingredient as a pharmaceutical composition. Accordingly, the disclosure further provides pharmaceutical compositions, which include therapeutically effective mounts of compounds of Formula (I) or pharmaceutically acceptable salts thereof, and one or more pharmaceutically acceptable carriers, diluents, or excipients. When applied to a combination, the term refers to combined amounts of the active ingredients that result in the therapeutic effect, whether administered in combination, serially, or simultaneously. The compounds of Formula I and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the disclosure there is also provided a process for the preparation of a pharmaceutical formulation including admixing a compound of Formula (I), or a pharmaceutically acceptable salt thereof or a prodrug thereof, with one or more pharmaceutically acceptable carriers, diluents, or excipients.

When the compositions of this disclosure comprise a combination of a compound of the present disclosure and one or more additional therapeutic or prophylactic agent, both the compound and the additional agent are usually present at dosage levels of between about 10 to 150%, and more typically between about 10 and 80% of the dosage normally administered in a monotherapy regimen.

Utility: Compounds of the invention can be used for treatment of a variety of clinical conditions including, but not limited to, treatment of rheumatoid arthritis, pulmonary fibrosis, HIV infection, and cancer. Exemplary cancers that can be treated using compounds of the invention include, but are not limited to, breast cancer, pancreatic cancer, melanoma, prostate cancer, kidney cancer, neuroblastoma, non-Hodgkin's lymphoma, lung cancer, ovarian cancer, colorectal cancer, multiple myeloma, glioblastoma multiforme, and chronic lymphocytic leukemia.

Methods of the invention include treating any disorders associated with CXCR4/SDF-1 interaction or CXCR4 receptor activity. Curative treatment refers to processes involving a slowing, interrupting, arresting, controlling, or stopping of disease progression, but does not necessarily involve a total elimination of all disease-related symptoms, conditions, or disorders.

The compounds of the present invention can be administered by a variety of routes. Typically, compounds of the invention are formulated for parenteral administration.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

The following abbreviations are used: Ac: acetyl; Boc: tert-butyloxycarbonyl; BOP: (benzotriazol-1-yloxy)-tris(dimethylamino)phosphoniumhexafluorophosphate; Bz: benzoyl; Bzl: benzyl; Dab: 1,4-diaminobutyric acid; Dap: 1,3-diaminopropionic acid; DCC: dicyclohexyl-carbodiimide; DCM: dichloromethane; DIC: diisopropyl carbodiimide; DIEA: diisopropyl-ethylamine; DMF: N,N-dimethyl formamide; DMSO: dimethyl-sulfoxide; EDT: 1,2-ethane-dithiol; Et: ethyl; Fmoc: 9-fluor-enylmethoxy carbonyl; HATU: N-[(dimethylamino)-1H-1,2,3-triazolo[4,5-b]pyridin-1-yl-methylene]-N-methylmethanaminium hexafluorophosphate N-oxide; HBTU: O-benzo-triazolyl-N,N,N',N'-tetramethyl-uronium hexafluorophosphate; HCTU: 1H-benzotriazo-lium 1-[bis(dimethylamino)methylene]-5-chloro-3-oxide hexafluorophosphate; HOBt: hydroxybenzotriazole; hCys: homocysteine; iPr: isopropyl; IPA: isopropyl alcohol; Me: methyl; Mpa: 3-mercaptopropionic acid; 2Nal: 2-naphthylalanine; 1Nal: 1-naphthylalanine; NMM: N-methylmorpholine; NMP: N-methyl-pyrrolidone; Orn: ornithine; Pbf: 2,2,4,6,7-pentamethyl-dihydrobenzofurane-5-sulfonyl; PBS: phosphate buffered saline; PyBOP: (benzotriazol-1-yloxy)-tris(pyrrolidino)-phosphonium hexafluoro-phosphate; PyBrOP: bromotris(pyrrolidino)phosphonium hexafluorophosphate; tBu: tert-butyl; TFA: trifluoroacetic acid; TFE: trifluroethanol; THF: tetrahydrofuran; TIS: triisopropyl silane; Trt: trityl; all common amino acids are expressed as three letter symbols or otherwise specified.

Preparation of compounds of the present invention as described in the following examples is meant to be illustrative rather than limiting. In each of these examples, the observed molecular weight is reported as a de-convoluted value. The de-convoluted value is derived from the formula MW (observed)=n(m/z)−n, where m/z represents the charged ion (positive mode) and n is the number of charges of the specific species. When multiple charged species are present in the mass spectrum, the observed molecular weight is reported as an average.

General Method of Peptide Synthesis, Cyclic Structure Formation, and Salt Exchange: Peptides were synthesized using solid phase peptide synthesis chemistry known in the art. The cyclic structure of those peptides was established, for a disulfide, by using iodine oxidation in the presence of acidic acid, or for a bisthioether ring, by nucleophilic substitution using a bis(halomethyl) aryl compound, typically using 1.3 equivalents of a bis(bromomethyl) aryl compound, in the presence of a base, such as 15 mM ammonium bicarbonate solution.

Final products were purified by reverse phased HPLC and further characterized by analytical HPLC and mass spectroscopy. Peptides purified from reverse phased HPLC were usually in trifluoroacetic acid (TFA) form. This salt was typically converted to a more pharmaceutically friendly salt form, such as acetic acid or hydrochloric acid salt form. Converting a peptide in TFA salt to a hydrochloric acid salt can be achieved by repeated lyophilization of the peptide in TFA salt in a dilute hydrochloric acid solution. For conversion of a peptide in TFA salt to an acetate salt, typically the following process was used.

Strong anion exchange resin (chloride form, substitution 3 mmole/g, water content 50%, using 2 grams of resin per gram of peptide) was first washed three times with milli Q water, then three times with 1 N NaOH solution three times, 5 min/time, and then five times with milli Q water, 5 min/time. The resin was further washed with 75% ethanol water until the pH reaches about 7.4. This resin was treated with 10% acetic acid solution three times, five minutes each time. The resin was then washed with 1% acetic acid solution three times, five minutes each time. The resin was ready for the salt conversion of the purified peptide.

The purified, lyophilized peptide was dissolved in 1% acetic acid solution and added to the prepared resin described above. The mixture was agitated or magnetically stirred at room temperature for 1 h. The supernatant was separated. The resin was washed three times with 1% acetic acid solution. The supernatant and the washing solution were combined, filtered through a 0.22 µm membrane and lyophilized, to afford a peptide in acetate salt.

Example 1: cyclo[Mpa-Tyr-Arg-(D-Arg)-2Nal-Gly-Cys]-Arg-Gly-(D-Phe)-Gly-NH$_2$ (SEQ ID NO:12): The sequence Mpa(Trt)-Tyr(tBu)-Arg(Pbf)-(D-Arg(Pbf))-2Nal-Gly-Cys (Trt)-Arg(Pbf)-Gly-(D-Phe)-Gly (SEQ ID NO:13) was assembled by standard Fmoc chemistry using Rink AM resin. Briefly, 3.6 grams of Rink AM resin was swollen in DCM for 14 h and then washed four times with DMF. Removal of Fmoc was carried out in 20% piperidine in DMF for 20 min at room temperature and was washed several times with DMF. Ninhydrin test was negative. Stepwise chain assembly started from the C-terminal end of the linear peptide and was accomplished in 11 major steps.

In step 1, three equivalents of protected amino acid Fmoc-Gly were activated with DCC/HOBt in DMF, and coupled to the Fmoc-removed Rink AM resin above for 2 h at room temperature followed by Fmoc removal using 20% piperidine in DMF for 20 min. In step 2, three equivalents of Fmoc-(D-Phe) were activated with DCC/HOBt in DMF and coupled to the deprotected resin from step 1 for 2 h at room temperature. Appropriate steps were then continued using Fmoc-protected amino acids, respectively, until step 11, the coupling of 3-(tritylthio) propionic acid (Mpa(Trt)).

The finished peptide was simultaneously deprotected and cleaved from the resin using 36 mL of a cleavage cocktail of TFA/EDT/TIS/H$_2$O/thioanisole/phenol (per 100 mL of solution contains 81.5 mL TFA, 2.5 mL EDT, 1.0 mL TIS, 5.0 mL H2O, 5.0 mL thioanisole, and 5.0 grams phenol) for 70 min at room temperature. To this cleavage mixture was added eight volumes of methyl t-butyl ether. The crude peptide precipitates were separated by centrifugation at 3000 rpm for 3 min. The crude peptide precipitates were washed three times with methyl t-butyl ether. The crude peptide was then dissolved in aqueous acetonitrile and lyophilized.

The crude lyophilized product was used directly in the cyclization reaction. The lyophilized crude peptide was dissolved in water at 0.5 mg/mL (500 mg of crude peptide in one liter) and the pH of the solution was adjusted to pH 6.5 using 1 M of ammonium carbonate solution with magnetic stirring. Under stirring, hydrogen peroxide solution was added to the crude peptide solution to a final concentration of 0.03% to promote disulfide bond formation. Cyclization was complete within 1 h as monitored by mass spectroscopy. The cyclized final product was purified using a reverse-phased preparative column Daisogel (50×250 mm, 8 m); mobile phases—Solvent A: 0.1% TFA water; Solvent B: 0.1% TFA acetonitrile. Fractions containing the target product were combined and lyophilized (a TFA salt).

Exchange of salt form: Strong anion exchange resin (chloride form, substitution 3 mmole/g, water content 50%, using 2 grams of resin per gram of peptide) was first washed three times with milli Q water, then three times with 1 N NaOH solution three times, 5 min/time, and then five times with milli Q water, 5 min/time. The resin was further washed with 75% ethanol water until the pH reaches about 7.4. This resin was treated with 10% acetic acid solution three times, five minutes each time. The resin was then washed with 1% acetic acid solution three times, five minutes each time. The resin was ready for the salt conversion of the purified peptide.

The purified, lyophilized peptide was dissolved in 1% acetic acid solution and added to the prepared resin described above. The mixture was agitated or magnetically stirred at room temperature for 1 h. The supernatant was separated. The resin was washed three times with 1% acetic acid solution. The supernatant and the washing solution were combined, filtered through a 0.22 m membrane and lyophilized, to afford a peptide in acetate salt. Analytical HPLC purity of the final peptide product 96.64%; MW cal.: 1353.49; MW obs.: 1353.45; peptide content 82.88%; acetic acid content 7.78%.

Example 2: cyclo[Mpa-Tyr-Lys(iPr)-(D-Arg)-2Nal-Gly-Cys]-Arg-Gly-(D-Phe)-Gly-NH$_2$ (SEQ ID NO:14): The sequence Mpa(Trt)-Tyr(tBu)-Lys(iPr)-(D-Arg(Pbf))-2Nal-Gly-Cys(Trt)-Arg(Pbf)-Gly-(D-Phe)-Gly (SEQ ID NO:15) was assembled by standard Fmoc chemistry using Rink AM resin. Briefly, 3.6 grams of Rink AM resin was swollen in DCM for 14 h and then washed four times with DMF. Removal of Fmoc was carried out in 20% piperidine in DMF for 20 min at room temperature and washed several times with DMF. Ninhydrin test was negative. Stepwise chain assembly started from the C-terminal end of the linear peptide and was accomplished in 11 major steps.

In step 1, three equivalents of protected amino acid Fmoc-Gly were activated with DCC/HOBt in DMF, and coupled to the Fmoc-removed Rink AM resin above for 2 h at room temperature followed by Fmoc removal using 20% piperidine in DMF for 20 min. In step 2, three equivalents of Fmoc-(D-Phe) were activated with DCC/HOBt in DMF and coupled to the deprotected resin from step 1 for 2 h at room temperature. Appropriate steps were then continued using corresponding Fmoc-protected amino acids, respectively, until step 11, the coupling of 3-(tritylthio) propionic acid (Mpa(Trt)).

The finished peptide was simultaneously deprotected and cleaved from the resin using 36 mL of a cleavage cocktail of TFA/EDT/TIS/H$_2$O/thioanisole/phenol (per 100 mL of solution contains 81.5 mL TFA, 2.5 mL EDT, 1.0 mL TIS, 5.0 mL H$_2$O, 5.0 mL thioanisole, and 5.0 grams phenol) cleavage cocktail of TFA/EDT/TIS/H$_2$O/thioanisole/phenol (per 100 mL of solution contains 81.5 mL TFA, 2.5 mL EDT, 1.0 mL TIS, 5.0 mL H$_2$O, 5.0 mL thioanisole, and 5.0 grams phenol) for 70 min at room temperature. To the cleavage mixture was added eight volumes of methyl t-butyl ether. The crude peptide precipitates were separated by centrifugation at 3000 rpm for 3 min. The crude peptide precipitates were washed three times with methyl t-butyl ether. The crude peptide was then dissolved in aqueous acetonitrile and lyophilized.

The crude lyophilized product was used directly in the cyclization reaction. The lyophilized crude peptide was dissolved in water at 0.5 mg/mL (500 mg of crude peptide in one liter) and the pH of the solution was adjusted to pH 6.5 using 1 M of ammonium carbonate solution with magnetic stirring. Under stirring, hydrogen peroxide solution was added to the crude peptide solution to a final concentration of 0.03% to promote disulfide bond formation. Cyclization was completed within 1 hour as monitored by mass spectroscopy. The cyclized final product was purified using a reverse-phased preparative column Daisogel (50×250 mm, 8 m); mobile phases—Solvent A: 0.1% TFA water; Solvent B: 0.1% TFA acetonitrile. Fractions containing the target product were combined and lyophilized (a TFA salt).

Exchange of salt form: Strong anion exchange resin (chloride form, substitution 3 mmole/g, water content 50%, using 2 grams of resin per gram of peptide) was first washed three times with milli Q water, then three times with 1 N NaOH solution three times, 5 min/time, and then five times with milli Q water, 5 min/time. The resin was further washed with 75% ethanol water until the pH reaches about 7.4. This resin was treated with 10% acetic acid solution three times, five minutes each time. The resin was then washed with 1% acetic acid solution three times, five minutes each time. The resin was ready for the salt conversion of the purified peptide.

The purified, lyophilized peptide was dissolved in 1% acetic acid solution and added to the prepared resin described above. The mixture was agitated or magnetically stirred at room temperature for 1 h. The supernatant was separated. The resin was washed three times with 1% acetic acid solution. The supernatant and the washing solution were combined, filtered through a 0.22 m membrane and lyophilized, to afford a peptide in acetate salt. Analytical HPLC purity of the final peptide product 98.78%; MW cal.: 1366.93; MW obs.: 1367.70; peptide content 83.55%; acetic acid content 7.75%.

Example 3: cyclo[Mpa-Tyr-Lys(iPr)-(D-Arg)-2Nal-Gly-Cys]-Lys(iPr)-Gly-(D-Phe)-Gly-NH$_2$ (SEQ ID NO:16): The sequence Mpa(Trt)-Tyr(tBu)-Lys(iPr)-(D-Arg(Pbf))-2Nal-Gly-Cys(Trt)-Lys(iPr)-Gly-(D-Phe)-Gly (SEQ ID NO:17) was assembled by standard Fmoc chemistry using Rink AM resin. Briefly, 3.6 grams of Rink AM resin was swollen in DCM for 14 h and then washed four times with DMF. Removal of Fmoc was carried out in 20% piperidine in DMF for 20 min at room temperature and washed several times with DMF. Ninhydrin test was negative. Stepwise chain assembly started from the C-terminal end of the linear peptide and was accomplished in 11 major steps.

In step 1, three equivalents of protected amino acid Fmoc-Gly were activated with DCC/HOBt in DMF, and coupled to the Fmoc-removed Rink AM resin above for 2 h at room temperature followed by Fmoc removal using 20% piperidine in DMF for 20 min. In step 2, three equivalents of Fmoc-(D-Phe) were activated with DCC/HOBt in DMF and coupled to the deprotected resin from step 1 for 2 h at room temperature. Appropriate steps were then continued using corresponding Fmoc-protected amino acids, respectively, until step 11, the coupling of 3-(tritylthio) propionic acid (Mpa(Trt)).

The finished peptide was simultaneously deprotected and cleaved from the resin using 36 mL of a cleavage cocktail of TFA/EDT/TIS/H$_2$O/thioanisole/phenol (per 100 mL of solution contains 81.5 mL TFA, 2.5 mL EDT, 1.0 mL TIS, 5.0 mL H2O, 5.0 mL thioanisole, and 5.0 grams phenol) for 70 min at room temperature. To the cleavage mixture was added eight volumes of methyl t-butyl ether. The crude peptide precipitates were separated by centrifugation at 3000 rpm for 3 min. The crude peptide precipitates were washed three times with methyl t-butyl ether. The crude peptide was then dissolved in aqueous acetonitrile and lyophilized.

The crude lyophilized product was used directly in the cyclization reaction. The lyophilized crude peptide was dissolved in water at 0.5 mg/mL (500 mg of crude peptide in one liter) and the pH of the solution was adjusted to pH 6.5 using 1 M of ammonium carbonate solution with magnetic stirring. Under stirring, hydrogen peroxide solution was added to the crude peptide solution to a final concentration of 0.03% to promote disulfide bond formation. Cyclization was completed within 1 h as monitored by mass spectroscopy. The cyclized final product was purified using a reverse-phased preparative column Daisogel (50×250 mm, 8 m); mobile phases—Solvent A: 0.1% TFA water; Solvent B: 0.1% TFA acetonitrile. Fractions containing the target product were combined and lyophilized (a TFA salt).

Exchange of salt form: Strong anion exchange resin (chloride form, substitution 3 mmole/g, water content 50%, using 2 grams of resin per gram of peptide) was first washed three times with milli Q water, then three times with 1 N NaOH solution three times, 5 min/time, and then five times with milli Q water, 5 min/time. The resin was further washed with 75% ethanol water until the pH reaches about 7.4. This resin was treated with 10% acetic acid solution three times, five minutes each time. The resin was then washed with 1% acetic acid solution three times, five minutes each time. The resin was ready for the salt conversion of the purified peptide.

The purified, lyophilized peptide was dissolved in 1% acetic acid solution and added to the prepared resin described above. The mixture was agitated or magnetically stirred at room temperature for 1 h. The supernatant was separated. The resin was washed three times with 1% acetic acid solution. The supernatant and the washing solution were combined, filtered through a 0.22 m membrane and lyophilized, to afford a peptide in acetate salt. Analytical HPLC purity of the final peptide product 98.14%; MW cal.: 1381.35; MW obs.: 1381.80; peptide content 85.26%; acetic acid content 6.77%.

Example 4: cyclo[Mpa-Tyr-Lys(iPr)-(D-Arg)-2Nal-Gly-Cys]-(D-Arg)-Gly-(D-Phe)-Gly-NH$_2$ (SEQ ID NO:18): The sequence Mpa(Trt)-Tyr(tBu)-Lys(iPr)-(D-Arg(Pbf))-2Nal-Gly-Cys(Trt)-(D-Arg(Pbf))-Gly-(D-Phe)-Gly (SEQ ID NO:19) was assembled by standard Fmoc chemistry using Rink AM resin. Briefly, 3.6 grams of Rink AM resin was swollen in DCM for 14 h and then washed four times with DMF. Removal of Fmoc was carried out in 20% piperidine in DMF for 20 min at room temperature and washed several times with DMF. Ninhydrin test was negative. Stepwise chain assembly started from the C-terminal end of the linear peptide and was accomplished in 11 major steps.

In step 1, three equivalents of protected amino acid Fmoc-Gly were activated with DCC/HOBt in DMF, and coupled to the Fmoc-removed Rink AM resin above for 2 h at room temperature followed by Fmoc removal using 20% piperidine in DMF for 20 min. In step 2, three equivalents of Fmoc-(D-Phe) were activated with DCC/HOBt in DMF and coupled to the deprotected resin from step 1 for 2 h at room temperature. Appropriate steps were then continued using corresponding Fmoc-protected amino acids, respectively, until step 11, the coupling of 3-(tritylthio) propionic acid (Mpa(Trt)).

The finished peptide was simultaneously deprotected and cleaved from the resin using 36 mL of a cleavage cocktail of TFA/EDT/TIS/H$_2$O/thioanisole/phenol (per 100 mL of solution contains 81.5 mL TFA, 2.5 mL EDT, 1.0 mL TIS, 5.0 mL H2O, 5.0 mL thioanisole, and 5.0 grams phenol) for 70 min at room temperature. To the cleavage mixture was added eight volumes of methyl t-butyl ether. The crude peptide precipitates were separated by centrifugation at 3000 rpm for 3 min. The crude peptide precipitates were washed three times with methyl t-butyl ether. The crude peptide was then dissolved in aqueous acetonitrile and lyophilized.

The crude lyophilized product was used directly in the cyclization reaction. The lyophilized crude peptide was dissolved in water at 0.5 mg/mL (500 mg of crude peptide in one liter) and the pH of the solution was adjusted to pH 6.5 using 1 M of ammonium carbonate solution with magnetic stirring. Under stirring, hydrogen peroxide solution was added to the crude peptide solution to a final concentration of 0.03% to promote disulfide bond formation. Cyclization was completed within 1 h as monitored by mass spectroscopy. The cyclized final product was purified using a reverse-phased preparative column Daisogel (50×250 mm, 8 m); mobile phases—Solvent A: 0.1% TFA water; Solvent B: 0.1% TFA acetonitrile. Fractions containing the target product were combined and lyophilized (a TFA salt).

Exchange of salt form: Strong anion exchange resin (chloride form, substitution 3 mmole/g, water content 50%, using 2 grams of resin per gram of peptide) was first washed three times with milli Q water, then three times with 1 N NaOH solution three times, 5 min/time, and then five times with milli Q water, 5 min/time. The resin was further washed with 75% ethanol water until the pH reaches about 7.4. This resin was treated with 10% acetic acid solution three times, five minutes each time. The resin was then washed with 1% acetic acid solution three times, five minutes each time. The resin was ready for the salt conversion of the purified peptide.

The purified, lyophilized peptide was dissolved in 1% acetic acid solution and added to the prepared resin described above. The mixture was agitated or magnetically stirred at room temperature for 1 h. The supernatant was separated. The resin was washed three times with 1% acetic acid solution. The supernatant and the washing solution were combined, filtered through a 0.22 m membrane and lyophilized, to afford a peptide in acetate salt. Analytical HPLC purity of the final peptide product 97.02%; MW cal.: 1366.83; MW obs.: 1367.25; peptide content 83.77%; acetic acid content 8.37%.

Example 5: cyclo[Mpa-Arg-Tyr-Arg-2Nal-Gly-Cys]-Arg-Gly-(D-Phe)-Gly-NH$_2$ (SEQ ID NO:20): The sequence Mpa(Trt)-Arg(Pbf)-Tyr(tBu)-Arg(Pbf)-2Nal-Gly-Cys(Trt)-Arg(Pbf)-Gly-(D-Phe)-Gly (SEQ ID NO:21) was assembled by standard Fmoc chemistry using Rink AM resin. Briefly, 3.6 grams of Rink AM resin was swollen in DCM for 14 h and then washed four times with DMF. Removal of Fmoc was carried out in 20% piperidine in DMF for 20 min at room temperature and washed several times with DMF. Ninhydrin test was negative. Stepwise chain assembly started from the C-terminal end of the linear peptide and was accomplished in 11 major steps.

In step 1, three equivalents of protected amino acid Fmoc-Gly were activated with DCC/HOBt in DMF, and coupled to the Fmoc-removed Rink AM resin above for 2 h at room temperature followed by Fmoc removal using 20% piperidine in DMF for 20 min. In step 2, three equivalents of Fmoc-2Nal were activated with DCC/HOBt in DMF and coupled to the deprotected resin from step 1 for 2 h at room temperature. Appropriate steps were then continued using corresponding Fmoc-protected amino acids, respectively, until step 11, the coupling of 3-(tritylthio) propionic acid (Mpa(Trt)).

The finished peptide was simultaneously deprotected and cleaved from the resin using 36 mL of a cleavage cocktail of TFA/EDT/TIS/$H_2O$/thioanisole/phenol (per 100 mL of solution contains 81.5 mL TFA, 2.5 mL EDT, 1.0 mL TIS, 5.0 mL H2O, 5.0 mL thioanisole, and 5.0 grams phenol) for 70 min at room temperature. To the cleavage mixture was added eight volumes of methyl t-butyl ether. The crude peptide precipitates were separated by centrifugation at 3000 rpm for 3 min. The crude peptide precipitates were washed three times with methyl t-butyl ether. The crude peptide was then dissolved in aqueous acetonitrile and lyophilized.

The crude lyophilized product was used directly in the cyclization reaction. The lyophilized crude peptide was dissolved in water at 0.5 mg/mL (500 mg of crude peptide in one liter) and the pH of the solution was adjusted to pH 6.5 using 1 M of ammonium carbonate solution with magnetic stirring. Under stirring, hydrogen peroxide solution was added to the crude peptide solution to a final concentration of 0.03% to promote disulfide bond formation. Cyclization was completed within 1 h as monitored by mass spectroscopy. The cyclized final product was purified using a reverse-phased preparative column Daisogel (50×250 mm, 8 m); mobile phases—Solvent A: 0.1% TFA water; Solvent B: 0.1% TFA acetonitrile. Fractions containing the target product were combined and lyophilized (a TFA salt).

Exchange of salt form: Strong anion exchange resin (chloride form, substitution 3 mmole/g, water content 50%, using 2 grams of resin per gram of peptide) was first washed three times with milli Q water, then three times with 1 N NaOH solution three times, 5 min/time, and then five times with milli Q water, 5 min/time. The resin was further washed with 75% ethanol water until the pH reaches about 7.4. This resin was treated with 10% acetic acid solution three times, five minutes each time. The resin was then washed with 1% acetic acid solution three times, five minutes each time. The resin was ready for the salt conversion of the purified peptide.

The purified, lyophilized peptide was dissolved in 1% acetic acid solution and added to the prepared resin described above. The mixture was agitated or magnetically stirred at room temperature for 1 h. The supernatant was separated. The resin was washed three times with 1% acetic acid solution. The supernatant and the washing solution were combined, filtered through a 0.22 m membrane and lyophilized, to afford a peptide in acetate salt. Analytical HPLC purity of the final peptide product 96.05%; MW cal.: 1353.49; MW obs.: 1353.00; peptide content 83.51%; acetic acid content 5.51%.

Example 6: cyclo[Mpa-Tyr-Lys(iPr)-(D-Arg)-2Nal-Gly-Cys]-Lys(iPr)-Gly-(D-Phe)-Gly-NH(Et) (SEQ ID NO:22): The sequence Mpa(Trt)-Tyr(tBu)-Lys(iPr, Boc)-(D-Arg(Pbf))-2Nal-Gly-Cys(Trt)-Lys(iPr, Boc)-Gly-(D-Phe)-Gly (SEQ ID NO:23) was assembled by standard Fmoc chemistry using 2-chlorotrityl chloride resin. Briefly, 4.0 grams of the resin was swollen in DCM for 2 h, washed four times with DMF and then once with DCM. Based on a substitution of 0.4 mmole/gram, the loading of the first residue Fmoc-Gly was carried out in DCM using four equivalents of amino acid activated with DIEA. The coupling at room temperature for 1.5 h was followed by capping of the unreacted substitution sites with methanol/DIEA (1:1, v/v, 24 mL) for 30 min. Removal of Fmoc protection was carried out in 20% piperidine in DMF for 20 min at room temperature and washed several times with DMF. Ninhydrin test was negative. Stepwise chain assembly of the linear peptide was continued and accomplished in a total of 11 major steps.

After the coupling of Fmoc-Gly, in step 2 three equivalents of Fmoc-(D-Phe) were activated with DCC/HOBt in DMF and coupled to the deprotected resin from step 1 for 2 h at room temperature. Appropriate steps were then continued using corresponding Fmoc-protected amino acids, respectively, until step 11, the coupling of 3-(tritylthio) propionic acid (Mpa(Trt)).

The finished linear peptide acid was cleaved from the resin in a fully protected form by using 20% TFE in DCM (30 mL per gram of resin) for 90 min at room temperature. The cleavage solution was separated by filtration and a second cleavage was carried out using the same 20% TFE in DCM for 60 min. Resin was again removed by filtration and the two cleavage solutions are then combined. The solvents were removed by rotovap and the residue was dried under vacuum to afford the crude, fully protected linear peptide acid, Mpa(Trt)-Tyr(tBu)-Lys(iPr, Boc)-(D-Arg(Pbf))-2Nal-Gly-Cys(Trt)-Lys(iPr, Boc)-Gly-(D-Phe)-Gly-OH.

Ethyl amination: The crude linear peptide acid was dissolved in dry DMF at 15 mg/mL. To the peptide acid solution was added three molar equivalents of HATU, 2,4,6-trimethylpyridine, and ethylamine, respectively. The ethyl amination reaction was accomplished within one hour as monitored by mass spectroscopy. The solvents were evaporated and the residues were dried under vacuum.

Deprotection: The side chain protections of the lyophilized crude linear peptide was removed using 10 mL of a cleavage cocktail of TFA/EDT/TIS/$H_2O$/thioanisole/phenol per gram of crude peptide material (per 100 mL of solution contains 81.5 mL TFA, 2.5 mL EDT, 1.0 mL TIS, 5.0 mL H2O, 5.0 mL thioanisole, and 5.0 grams phenol) for 70 min at room temperature. Then to the cleavage mixture was added eight volumes of methyl t-butyl ether. The crude peptide precipitates were separated by centrifugation at 3000 rpm for 3 min. The crude peptide precipitates were washed three times with methyl t-butyl ether. The crude peptide was then dissolved in aqueous acetonitrile and lyophilized.

Cyclization: The crude lyophilized product was used directly in the cyclization reaction. The lyophilized crude peptide was dissolved in 20% acetic acid at 0.5 mg/mL. Under stirring, add 0.03% mole/L iodine solution until the peptide solution turned light yellow. The solution was protected from visible light during the cyclization. Cyclization was completed within 0.5 h as monitored by mass spectroscopy. The cyclized final product was purified using a reverse-phased preparative column Daisogel (50×250 mm, 8 m) with mobile phases—A: 0.1% TFA water; B: 0.1% TFA acetonitrile. Fractions containing the target product were combined and lyophilized (a TFA salt).

Exchange of salt form: Strong anion exchange resin (chloride form, substitution 3 mmole/g, water content 50%, using 2 grams of resin per gram of peptide) was first washed three times with milli Q water, then three times with 1 N NaOH solution three times, 5 min/time, and then five times with milli Q water, 5 min/time. The resin was further washed with 75% ethanol water until the pH reaches about 7.4. This resin was treated with 10% acetic acid solution three times, five minutes each time. The resin was then washed with 1% acetic acid solution three times, five minutes each time. The resin was ready for the salt conversion of the purified peptide.

The purified, lyophilized peptide was dissolved in 1% acetic acid solution and added to the prepared resin described above. The mixture was agitated or magnetically stirred at room temperature for 1 h. The supernatant was separated. The resin was washed three times with 1% acetic acid solution. The supernatant and the washing solution were combined, filtered through a 0.22 m membrane and lyophilized, to afford a peptide in acetate salt. Analytical HPLC purity of the final peptide product 96.54%; MW cal.: 1408.69; MW obs.: 1409.10; peptide content 84.46%; acetic acid content 6.64%.

Example 7: cyclo[Mpa-Tyr-Lys(iPr)-(D-Arg)-2Nal-Gly-Cys]-Lys(iPr)-Gly-NH(Et) (SEQ ID NO:24): The sequence Mpa(Trt)-Tyr(tBu)-Lys(iPr, Boc)-(D-Arg(Pbf))-2Nal-Gly-Cys(Trt)-Lys(iPr, Boc)-Gly (SEQ ID NO:25) was assembled by standard Fmoc chemistry using 2-chlorotrityl chloride resin. Briefly, 4.0 grams of the resin was swollen in DCM for 2 h, washed four times with DMF and then once with DCM. Based on a substitution of 0.4 mmole/gram, the loading of the first residue Fmoc-Gly was carried out in DCM using four equivalents of amino acid activated with DIEA. The coupling at room temperature for 1.5 h was followed by capping of the unreacted substitution sites with methanol/DIEA (1:1, v/v, 24 mL) for 30 min. Removal of Fmoc protection was carried out in 20% piperidine in DMF for 20 min at room temperature and washed several times with DMF. Ninhydrin test was negative. Stepwise chain assembly of the linear peptide was continued and accomplished in a total of 9 major steps.

After the coupling of Fmoc-Gly, in step 2 three equivalents of Fmoc-Lys(iPr, Boc) were activated with DCC/HOBt in DMF and coupled to the deprotected resin from step 1 for 2 h at room temperature. Appropriate steps were then continued using corresponding Fmoc-protected amino acids, respectively, until step 9, the coupling of 3-(tritylthio) propionic acid (Mpa(Trt)).

The finished linear peptide acid was cleaved from the resin in a fully protected form by using 20% TFE in DCM (30 mL per gram of resin) for 90 min at room temperature. The cleavage solution was separated by filtration and a second cleavage is carried out using the same 20% TFE in DCM for 60 min. Resin was again removed by filtration and the two cleavage solutions were combined. The solvents were then removed by rotovap and the residue was dried under vacuum to afford the crude, fully protected linear peptide acid, Mpa(Trt)-Tyr(tBu)-Lys(iPr, Boc)-(D-Arg (Pbf))-2Nal-Gly-Cys(Trt)-Lys(iPr, Boc)-Gly-OH.

Ethyl amination: The crude linear peptide acid was dissolved in dry DMF at 15 mg/mL. To the peptide acid solution was added three molar equivalents of HATU, 2,4, 6-trimethylpyridine, and ethylamine. The ethyl amination reaction was accomplished within one hour as monitored by mass spectroscopy. The solvents were evaporated and the residues were dried under vacuum.

The side chain protections of the lyophilized crude linear peptide was removed using 10 mL of a cleavage cocktail of TFA/EDT/TIS/$H_2O$/thioanisole/phenol per gram of crude peptide material (per 100 mL of solution contains 81.5 mL TFA, 2.5 mL EDT, 1.0 mL TIS, 5.0 mL $H_2O$, 5.0 mL thioanisole, and 5.0 grams phenol) for 70 min at room temperature. To the cleavage mixture was added eight volumes of methyl t-butyl ether. The crude peptide precipitates were separated by centrifugation at 3000 rpm for 3 min. The crude peptide precipitates were washed three times with methyl t-butyl ether. The crude peptide was then dissolved in aqueous acetonitrile and lyophilized.

Cyclization: The crude lyophilized product was used directly in the cyclization reaction. The lyophilized crude peptide was dissolved in 20% acetic acid at 0.5 mg/mL. Under stirring, added 0.03% mole/L iodine solution to the linear peptide solution until the peptide solution turned light yellow. The solution was protected from visible light during the cyclization. Cyclization was complete within 0.5 h as monitored by mass spectroscopy. The cyclized final product was purified using a reverse-phased preparative column Daisogel (50×250 mm, 8 m) with mobile phases—A: 0.1% TFA water; B: 0.1% TFA acetonitrile. Fractions containing the target product were combined and lyophilized (a TFA salt).

Exchange of salt form: Strong anion exchange resin (chloride form, substitution 3 mmole/g, water content 50%, using 2 grams of resin per gram of peptide) was first washed three times with milli Q water, then three times with 1 N NaOH solution three times, 5 min/time, and then five times with milli Q water, 5 min/time. The resin was further washed with 75% ethanol water until the pH reaches about 7.4. This resin was treated with 10% acetic acid solution three times, five minutes each time. The resin was then washed with 1% acetic acid solution three times, five minutes each time. The resin was ready for the salt conversion of the purified peptide.

The purified, lyophilized peptide was dissolved in 1% acetic acid solution and added to the prepared resin described above. The mixture was agitated or magnetically stirred at room temperature for 1 h. The supernatant was separated. The resin was washed three times with 1% acetic acid solution. The supernatant and the washing solution were combined, filtered through a 0.22 μm membrane and lyophilized, to afford a peptide in acetate salt. Analytical HPLC purity of the final peptide product 95.71%; MW cal.: 1204.51; MW obs.: 1205.25; peptide content 81.60%; acetic acid content 11.26%.

Example 8: cyclo[Mpa-Tyr-Lys(iPr)-(D-Arg)-2Nal-Gly-Cys]-Lys(iPr)-Gly-2Nal-Gly-$NH_2$ (SEQ ID NO:26): The sequence Mpa(Trt)-Tyr(tBu)-Lys(iPr)-(D-Arg(Pbf))-2Nal-Gly-Cys(Trt)-Lys(iPr)-Gly-2Nal-Gly (SEQ ID NO:27) was assembled by standard Fmoc chemistry using Rink AM resin. Briefly, 3.6 grams of Rink AM resin was swollen in DCM for 14 h and then washed four times with DMF. Removal of Fmoc was carried out in 20% piperidine in DMF for 20 min at room temperature and washed several times with DMF. Ninhydrin test was negative. Stepwise chain assembly started from the C-terminal end of the linear peptide and was accomplished in 11 major steps.

In step 1, three equivalents of protected amino acid Fmoc-Gly were activated with DCC/HOBt in DMF, and coupled to the Fmoc-removed Rink AM resin above for 2 h at room temperature followed by Fmoc removal using 20% piperidine in DMF for 20 min. In step 2, three equivalents of Fmoc-2Nal were activated with DCC/HOBt in DMF and coupled to the deprotected resin from step 1 for 2 h at room temperature. Appropriate steps were then continued using corresponding Fmoc-protected amino acids, respectively, until step 11, the coupling of 3-(tritylthio) propionic acid (Mpa(Trt)).

The finished peptide was simultaneously deprotected and cleaved from the resin using 36 mL of a cleavage cocktail of TFA/EDT/TIS/H$_2$O/thioanisole/phenol (per 100 mL of solution contains 81.5 mL TFA, 2.5 mL EDT, 1.0 mL TIS, 5.0 mL H2O, 5.0 mL thioanisole, and 5.0 grams phenol) for 70 min at room temperature. To the cleavage mixture was added eight volumes of methyl t-butyl ether. The crude peptide precipitates were separated by centrifugation at 3000 rpm for 3 min. The crude peptide precipitates were washed three times with methyl t-butyl ether. The crude peptide was then dissolved in aqueous acetonitrile and lyophilized.

The crude lyophilized product was used directly in the cyclization reaction. The lyophilized crude peptide was dissolved in water at 0.5 mg/mL (500 mg of crude peptide in one liter) and the pH of the solution was adjusted to pH 6.5 using 1 M of ammonium carbonate solution with magnetic stirring. Under stirring, hydrogen peroxide solution was added to the crude peptide solution to a final concentration of 0.03% to promote disulfide bond formation. Cyclization is complete within 1 h monitored by mass spectroscopy. The cyclized final product was purified using a reverse-phased preparative column Daisogel (50×250 mm, 8 m); mobile phases—Solvent A: 0.1% TFA water; Solvent B: 0.1% TFA acetonitrile. Fractions containing the target product were combined and lyophilized (a TFA salt).

Exchange of salt form: Strong anion exchange resin (chloride form, substitution 3 mmole/g, water content 50%, using 2 grams of resin per gram of peptide) was first washed three times with milli Q water, then three times with 1 N NaOH solution three times, 5 min/time, and then five times with milli Q water, 5 min/time. The resin was further washed with 75% ethanol water until the pH reaches about pH 7.4. This resin was treated with 10% acetic acid solution three times, five minutes each time. The resin was then washed with 1% acetic acid solution three times, five minutes each time. The resin was ready for the salt conversion of the purified peptide.

The purified, lyophilized peptide was dissolved in 1% acetic acid solution and added to the prepared resin described above. The mixture was agitated or magnetically stirred at room temperature for 1 h. The supernatant was separated. The resin was washed three times with 1% acetic acid solution. The supernatant and the washing solution were combined, filtered through a 0.22 m membrane and lyophilized, to afford a peptide in acetate salt. Analytical HPLC purity of the final peptide product 96.44%; MW cal.: 1430.43; MW obs.: 1431.00; peptide content 84.33%; acetic acid content 7.07%.

Example 9: Ac-cyclo[hCys-Tyr-Lys(iPr)-(D-Arg)-2Nal-Gly-Cys]-Lys(iPr)-Gly-(D-Phe)-Gly-NH$_2$ (SEQ ID NO:28): The sequence hCys(Trt)-Tyr(tBu)-Lys(iPr)-(D-Arg(Pbf))-2Nal-Gly-Cys(Trt)-Lys(iPr)-Gly-(D-Phe)-Gly (SEQ ID NO:29) was assembled manually by standard Fmoc chemistry using Rink AM resin. Briefly, 3.6 grams of Rink AM resin was swollen in DCM for 14 h and then washed four times with DMF. Removal of Fmoc was carried out in 20% piperidine in DMF for 20 min at room temperature and washed several times with DMF. Ninhydrin test was negative. Stepwise chain assembly started from the C-terminal end of the linear peptide and was accomplished in 11 major steps.

In step 1, three equivalents of protected amino acid Fmoc-Gly were activated with DIC/HOBt in DMF, and coupled to the Fmoc-removed Rink AM resin above for 2 h at room temperature followed by Fmoc removal using 20% piperidine in DMF for 20 min. In step 2, three equivalents of Fmoc-(D-Phe) were activated with DCC/HOBt in DMF and coupled to the deprotected resin from step 1. Appropriate steps were continued using corresponding Fmoc-protected amino acids, respectively, until step 11, the coupling of Fmoc-hCys(Trt). For step 11, Fmoc at the N-terminal end is removed using 20% piperidine in DMF and acetylation of the α-amino group was carried out with 22 mL of a mixture of acetic anhydride/DIEA/DMF (1:1:4, v/v) for 30 min at room temperature. The finished peptide was simultaneously deprotected and cleaved from the resin using 36 mL of a cleavage cocktail of TFA/EDT/TIS/H$_2$O/thioanisole/phenol (per 100 mL of solution contains 81.5 mL TFA, 2.5 mL EDT, 1.0 mL TIS, 5.0 mL H$_2$O, 5.0 mL thioanisole, and 5.0 grams phenol) for 70 min at room temperature. To the cleavage mixture was added eight volumes of methyl t-butyl ether. The crude peptide precipitates were separated by centrifugation at 3000 rpm for 3 min. The crude peptide precipitates were washed three times with methyl t-butyl ether. The crude peptide was then dissolved in aqueous acetonitrile and lyophilized.

The crude lyophilized product was used directly in the cyclization reaction. The lyophilized crude peptide was dissolved in water at 0.5 mg/mL (500 mg of crude peptide in one liter) and the pH of the solution was adjusted to pH 6.5 using 1 M of ammonium carbonate solution with magnetic stirring. Under stirring, hydrogen peroxide solution was added to the crude peptide solution to a final concentration of 0.03% to promote disulfide bond formation. Cyclization was completed within 1 h as monitored by mass spectroscopy. The cyclized final product was purified using a reverse-phased preparative column Daisogel (50×250 mm, 8 m); mobile phases—Solvent A: 0.1% TFA water; Solvent B: 0.1% TFA acetonitrile. Fractions containing the target product are combined and lyophilized (a TFA salt).

Exchange of salt form: Strong anion exchange resin (chloride form, substitution 3 mmole/g, water content 50%, using 2 grams of resin per gram of peptide) was first washed three times with milli Q water, then three times with 1 N NaOH solution three times, 5 min/time, and then five times with milli Q water, 5 min/time. The resin was further washed with 75% ethanol water until the pH reached about pH 7.4. This resin was treated with 10% acetic acid solution three times, five minutes each time. The resin was then washed with 1% acetic acid solution three times, five minutes each time. The resin was ready for the salt conversion of the purified peptide.

The purified, lyophilized peptide was dissolved in 1% acetic acid solution and added to the prepared resin described above. The mixture was agitated or magnetically stirred at room temperature for 1 h. The supernatant was separated. The resin was washed three times with 1% acetic acid solution. The supernatant and the washing solution were combined, filtered through a 0.22 m membrane and lyophilized, to afford a peptide in acetate salt. Analytical HPLC purity of the final peptide product 96.38%; MW cal.: 1451.84; MW obs.: 1452.60; peptide content 83.88%; acetic acid content 7.82%.

Example 10: Ac-cyclo[hCys-Tyr-Lys(iPr)-(D-Arg)-2Nal-Gly-Cys]-Lys(iPr)-Gly-NH$_2$ (SEQ ID NO: 30): The sequence hCys(Trt)-Tyr(tBu)-Lys(iPr)-(D-Arg(Pbf))-2Nal-Gly-Cys(Trt)-Lys(iPr)-Gly (SEQ ID NO:31) was assembled manually by standard Fmoc chemistry using Rink AM resin.

Briefly, 3.6 grams of Rink AM resin was swollen in DCM for 14 h and then washed four times with DMF. Removal of Fmoc was carried out in 20% piperidine in DMF for 20 min at room temperature and washed several times with DMF. Ninhydrin test was negative. Stepwise chain assembly started from the C-terminal end of the linear peptide and was accomplished in nine major steps. In step 1, three equivalents of protected amino acid Fmoc-Gly were activated with DIC/HOBt in DMF, and coupled to the Fmoc-removed Rink AM resin above for 2 h at room temperature followed by Fmoc removal using 20% piperidine in DMF for 20 min. In step 2, three equivalents of Fmoc-Lys(iPr) were activated with DCC/HOBt in DMF and coupled to the deprotected resin from step 1. Appropriate steps were continued using Fmoc-protected amino acids, respectively, until step 9, the coupling of Fmoc-hCys(Trt). For step 9, Fmoc at the N-terminal end was removed using 20% piperidine in DMF and acetylation of the α-amino group was carried out with 22 mL of a mixture of acetic anhydride/DIEA/DMF (1:1:4, v/v/v) for 30 min at room temperature. The finished peptide was simultaneously deprotected and cleaved from the resin using 36 mL of a cleavage cocktail of TFA/EDT/TIS/H$_2$O/thioanisole/phenol (per 100 mL of solution containing 81.5 mL TFA, 2.5 mL EDT, 1.0 mL TIS, 5.0 mL H2O, 5.0 mL thioanisole, and 5.0 grams phenol) for 70 min at room temperature. Then to the cleavage mixture was added eight volumes of methyl t-butyl ether. The crude peptide precipitates were separated by centrifugation at 3000 rpm for 3 min. The crude peptide precipitates were washed three times with methyl t-butyl ether. The crude peptide was then dissolved in aqueous acetonitrile and lyophilized.

The crude lyophilized product was used directly in the cyclization reaction. The lyophilized crude peptide was dissolved in water at 0.5 mg/mL (500 mg of crude peptide in one liter) and the pH of the solution was adjusted to pH 6.5 using 1 M of ammonium carbonate solution with magnetic stirring. Under stirring, hydrogen peroxide solution was added to the crude peptide solution to a final concentration of 0.03% to promote disulfide bond formation. Cyclization was completed within 1 h as monitored by mass spectroscopy. The cyclized final product was purified using a reverse-phased preparative column Daisogel (50×250 mm, 8 m); mobile phases—Solvent A: 0.1% TFA water; Solvent B: 0.1% TFA acetonitrile. Fractions containing the target product are combined and lyophilized (a TFA salt).

Exchange of salt form: Strong anion exchange resin (chloride form, substitution 3 mmole/g, water content 50%, using 2 grams of resin per gram of peptide) was first washed three times with milli Q water, then three times with 1 N NaOH solution three times, 5 min/time, and then five times with milli Q water, 5 min/time. The resin was further washed with 75% ethanol water until the pH reached about pH 7.4. This resin was treated with 10% acetic acid solution three times, five minutes each time. The resin was then washed with 1% acetic acid solution three times, five minutes each time.

The purified, lyophilized peptide was dissolved in 1% acetic acid solution and added to the prepared resin described above. The mixture was agitated or magnetically stirred at room temperature for 1 h. The supernatant was separated, and the resin was washed three times with 1% acetic acid solution. The supernatant and the washing solution were combined, filtered through a 0.22 m membrane and lyophilized, to afford a peptide as an acetate salt form. Analytical HPLC purity of the final peptide product 96.13%; MW cal.: 1247.61; MW obs.: 1248.00; peptide content 81.02%; acetic acid content 10.09%.

Example 11: Benzoyl-cyclo[hCys-Tyr-Lys(iPr)-(D-Arg)-2Nal-Gly-Cys]-Lys(iPr)-Gly-NH$_2$ (MLB-021) (SEQ ID NO: 32): The sequence hCys(Trt)-Tyr(tBu)-Lys(iPr,Boc)-(D-Arg(Pbf))-2Nal-Gly-Cys(Trt)-Lys(iPr,Boc)-Gly (SEQ ID NO:33) was assembled manually by standard Fmoc chemistry using Rink AM resin. Briefly, 3.6 grams of Rink AM resin was swollen in DCM for 14 h and then washed four times with DMF. Removal of Fmoc was carried out in 20% piperidine in DMF for 20 min at room temperature and washed several times with DMF. Ninhydrin test was negative. Stepwise chain assembly starts from the C-terminal end of the linear peptide and was accomplished in nine major steps. In step 1, three equivalents of protected amino acid Fmoc-Gly were activated with DIC/HOBt in DMF, and coupled to the Fmoc-removed Rink AM resin above for 2 h at room temperature followed by Fmoc removal using 20% piperidine in DMF for 20 min. In step 2, three equivalents of Fmoc-Lys(iPr,Boc) were activated with DCC/HOBt in DMF and coupled to the deprotected resin from step 1. Appropriate steps were continued using Fmoc-protected amino acids, respectively, until step 10, the coupling of benzoic acid, which was carried out just like an amino acid as previous steps. For step 10, no Fmoc removal was carried out.

The resulting peptide was deprotected and cleaved from the resin using 36 mL of a cleavage cocktail of TFA/EDT/TIS/H$_2$O/thioanisole/phenol (per 100 mL of solution contains 81.5 mL TFA, 2.5 mL EDT, 1.0 mL TIS, 5.0 mL H$_2$O, 5.0 mL thioanisole, and 5.0 grams phenol) for 70 min at room temperature. To the cleavage mixture was added eight volumes of methyl t-butyl ether. The crude peptide precipitates were separated by centrifugation at 3000 rpm for 3 min. The crude peptide precipitates were washed three times with methyl t-butyl ether. The crude peptide was then dissolved in aqueous acetonitrile and lyophilized.

The lyophilized crude peptide was dissolved in water containing 20% acetic acid at 0.5 mg/mL (500 mg of crude peptide in one liter). Under stirring, 0.03% mole/L iodine solution was added to the peptide solution until the solution became pale yellow. Cyclization was completed within 0.5 h in dark as monitored by mass spectroscopy. The cyclized final product was purified using a reverse-phased preparative column Daisogel (50×250 mm, 8 μm); mobile phases—Solvent A: 0.1% TFA water; Solvent B: 0.1% TFA acetonitrile. Fractions containing the target product were combined and lyophilized (a TFA salt).

Salt exchange afforded a peptide in acetate salt. Analytical HPLC purity of the final peptide product 95.98%; MW cal.: 1310.64; MW obs.: 1310.70; peptide content 78.48%.

Example 12: Benzoyl-cyclo[Cys-Tyr-Lys(iPr)-(D-Arg)-2Nal-Gly-hCys]-Lys(iPr)-Gly-NH$_2$ (MLB-022) (SEQ ID NO: 34): The sequence Cys(Trt)-Tyr(tBu)-Lys(iPr,Boc)-(D-Arg(Pbf))-2Nal-Gly-hCys(Trt)-Lys(iPr,Boc)-Gly (SEQ ID NO:35) was assembled manually by standard Fmoc chemistry using Rink AM resin. Briefly, 3.6 grams of Rink AM resin was swollen in DCM for 14 h and then washed four times with DMF. Removal of Fmoc was carried out in 20% piperidine in DMF for 20 min at room temperature and washed several times with DMF. Ninhydrin test was negative. Stepwise chain assembly started from the C-terminal end of the linear peptide and was accomplished in nine major steps. In step 1, three equivalents of protected amino acid Fmoc-Gly were activated with DIC/HOBt in DMF, and coupled to the Fmoc-removed Rink AM resin above for 2 h at room temperature followed by Fmoc removal using 20% piperidine in DMF for 20 min. In step 2, three equivalents of Fmoc-Lys(iPr,Boc) were activated with DCC/HOBt in DMF and coupled to the deprotected resin from step 1. Appropriate steps were continued using Fmoc-protected amino acids, respectively, until step 10, the coupling of benzoic acid, which was carried out just like an amino acid as previous steps. For step 10, no Fmoc removal was carried out.

The finished peptide was deprotected and cleaved from the resin using 36 mL of a cleavage cocktail of TFA/EDT/TIS/H$_2$O/thioanisole/phenol (per 100 mL of solution contains 81.5 mL TFA, 2.5 mL EDT, 1.0 mL TIS, 5.0 mL H$_2$O, 5.0 mL thioanisole, and 5.0 grams phenol) for 70 min at room temperature. To the cleavage mixture was added eight volumes of methyl t-butyl ether. The crude peptide precipitates were separated by centrifugation at 3000 rpm for 3 min. The crude peptide precipitates were washed three times with methyl t-butyl ether. The crude peptide was then dissolved in aqueous acetonitrile and lyophilized.

The lyophilized crude peptide was dissolved in water containing 20% acetic acid at 0.5 mg/mL (500 mg of crude peptide in one liter). Under stirring, 0.03% mole/L iodine solution was added to the peptide solution until the solution became pale yellow. Cyclization was complete within 0.5 h in dark as monitored by mass spectroscopy. The cyclized final product was purified using a reverse-phased preparative column Daisogel (50×250 mm, 8 μm); mobile phases—Solvent A: 0.1% TFA water; Solvent B: 0.1% TFA acetonitrile. Fractions containing the target product were combined and lyophilized (a TFA salt).

Salt exchange afforded a peptide in acetate salt. Analytical HPLC purity of the final peptide product 95.64%; MW cal.: 1310.64; MW obs.: 1310.55; peptide content 69.25%.

Example 13: Benzoyl-cyclo[Cys-Tyr-Lys(iPr)-(D-Arg)-2Nal-Gly-Cys]-Lys(iPr)-Gly-NH$_2$ (MLB-023) (SEQ ID NO: 36): The sequence Cys(Trt)-Tyr(tBu)-Lys(iPr,Boc)-(D-Arg(Pbf))-2Nal-Gly-Cys(Trt)-Lys(iPr,Boc)-Gly (SEQ ID NO:37) was assembled manually by standard Fmoc chemistry using Rink AM resin. Briefly, 3.6 grams of Rink AM resin was swollen in DCM for 14 h and then washed four times with DMF. Removal of Fmoc was carried out in 20% piperidine in DMF for 20 min at room temperature and washed several times with DMF. Ninhydrin test was negative. Stepwise chain assembly started from the C-terminal end of the linear peptide and was accomplished in nine major steps. In step 1, three equivalents of protected amino acid Fmoc-Gly were activated with DIC/HOBt in DMF, and coupled to the Fmoc-removed Rink AM resin above for 2 h at room temperature followed by Fmoc removal using 20% piperidine in DMF for 20 min. In step 2, three equivalents of Fmoc-Lys(iPr,Boc) were activated with DCC/HOBt in DMF and coupled to the deprotected resin from step 1. Appropriate steps were continued using Fmoc-protected amino acids, respectively, until step 10, the coupling of benzoic acid, which was carried out as in previous steps. For step 10, no Fmoc removal was carried out.

The finished peptide was deprotected and cleaved from the resin using 36 mL of a cleavage cocktail of TFA/EDT/TIS/H$_2$O/thioanisole/phenol (per 100 mL of solution contains 81.5 mL TFA, 2.5 mL EDT, 1.0 mL TIS, 5.0 mL H$_2$O, 5.0 mL thioanisole, and 5.0 grams phenol) for 70 min at room temperature. To the cleavage mixture was added eight volumes of methyl t-butyl ether. The crude peptide precipitates were separated by centrifugation at 3000 rpm for 3 min. The crude peptide precipitates were washed three times with methyl t-butyl ether. The crude peptide was then dissolved in aqueous acetonitrile and lyophilized.

The crude lyophilized product was used directly in the cyclization reaction. The lyophilized crude peptide was dissolved in water containing 20% acetic acid at 0.5 mg/mL (500 mg of crude peptide in one liter). Under stirring, 0.03% mole/L iodine solution was added to the peptide solution until the solution became pale yellow. Cyclization was complete within 0.5 h in dark as monitored by mass spectroscopy. The cyclized final product was purified using a reverse-phased preparative column Daisogel (50×250 mm, 8 μm); mobile phases—Solvent A: 0.1% TFA water; Solvent B: 0.1% TFA acetonitrile. Fractions containing the target product were combined and lyophilized (a TFA salt).

Salt exchange as it is described above afforded a peptide in acetate salt. Analytical HPLC purity of the final peptide product 97.04%; MW cal.: 1296.61; MW obs.: 1296.75; peptide content 78.15%.

Example 14: Benzoyl-cyclo[hCys-Tyr-Lys(iPr)-(D-Arg)-2Nal-Gly-Cys]-Lys(iPr)-Gly-NH(Et) (MLB-024) (SEQ ID NO: 38): The sequence hCys(Trt)-Tyr(tBu)-Lys(iPr,Boc)-(D-Arg(Pbf))-2Nal-Gly-Cys(Trt)-Lys(iPr,Boc)-Gly (SEQ ID NO:39) was assembled manually by standard Fmoc chemistry using 2-Chloro-trityl chloride resin. Briefly, 4.0 grams of the resin was swollen in DCM for 2 h, washed four times with DMF and then once with DCM. Based on a substitution of 0.4 mmole/gram, the loading of the first residue Fmoc-Gly was carried out in DCM using four equivalents of amino acid activated with five equivalents of DIEA. The coupling at room temperature for 1.5 h was followed by capping of the unreacted substitution sites with methanol/DIEA (1:1, v/v, 24 mL) for 30 min. Removal of Fmoc protection was carried out in 20% piperidine in DMF for 20 min at room temperature and washed several times with DMF. Ninhydrin test was negative. Stepwise chain assembly of the linear peptide was continued and accomplished in a total of 9 major steps.

After the coupling of Fmoc-Gly, in step 2 three equivalents of Fmoc-Lys(iPr, Boc) were activated with DCC/HOBt in DMF and coupled to the deprotected resin from step 1 for 2 h at room temperature. Appropriate steps were then continued using corresponding Fmoc-protected amino acids, respectively, until step 10, the coupling of benzoic acid, which was carried out just like an amino acid as previous steps. For step 10, no Fmoc removal was carried out.

The finished linear peptide acid was cleaved from the resin in a fully protected form by using 20% TFE in DCM (30 mL per gram of resin) for 90 min at room temperature. The cleavage solution was separated by filtration and a second cleavage was carried out using the same 20% TFE in DCM for 60 min. Resin was again removed by filtration and the two cleavage solutions were combined. The solvents were then removed and the residue was dried under vacuum to afford the crude, fully protected linear peptide acid, sequence Benzoyl-hCys(Trt)-Tyr(tBu)-Lys(iPr, Boc)-(D-Arg(Pbf))-2Nal-Gly-Cys(Trt)-Lys(iPr, Boc)-Gly-OH C-terminal ethyl amination and side chain protection removal: The crude linear peptide acid was dissolved in dry DMF at 15 mg/mL. To the peptide acid solution was added three molar equivalents of HATU, 2,4,6-trimethylpyridine, and ethylamine, respectively (3:3:3, molar ratio). The ethyl amination reaction was accomplished within one hour as monitored by mass spectroscopy. The solvents were evaporated and the residues were dried under vacuum.

The side chain protections of the lyophilized crude linear peptide was removed using 10 mL of a cleavage cocktail of TFA/EDT/TIS/H$_2$O/thioanisole/phenol per gram of crude peptide material (per 100 mL of solution contains 81.5 mL TFA, 2.5 mL EDT, 1.0 mL TIS, 5.0 mL H$_2$O, 5.0 mL thioanisole, and 5.0 grams phenol) for 70 min at room temperature. To the cleavage mixture was added eight volumes of methyl t-butyl ether. The crude peptide precipitates were separated by centrifugation at 3000 rpm for 3 min. The crude peptide precipitates were washed three times with methyl t-butyl ether. The crude peptide was then dissolved in aqueous acetonitrile and lyophilized.

Cyclization: The crude lyophilized product was used directly in the cyclization reaction. The lyophilized crude peptide was dissolved in 20% acetic acid at 0.5 mg/mL. Under stirring, add 0.03% mole/L iodine solution to the linear peptide solution until the peptide solution turns light yellow. The solution was protected from visible light during the cyclization. Cyclization was complete within 0.5 h as monitored by mass spectroscopy. The cyclized final product was purified using a reverse-phased preparative column Daisogel (50×250 mm, 8 µm) with mobile phases—A: 0.1% TFA water; B: 0.1% TFA acetonitrile. Fractions containing the target product were combined and lyophilized (a TFA salt).

Salt exchange as it is described above afforded a peptide in acetate salt. Analytical HPLC purity of the final peptide product 97.59%; MW cal.: 1338.69; MW obs.: 1338.90.

Example 15: Phenylacetyl-cyclo[hCys-Tyr-Lys(iPr)-(D-Arg)-2Nal-Gly-Cys]-Lys(iPr)-Gly-NH$_2$ (MLB-025) (SEQ ID NO: 40): The sequence hCys(Trt)-Tyr(tBu)-Lys(iPr, Boc)-(D-Arg(Pbf))-2Nal-Gly-Cys(Trt)-Lys(iPr,Boc)-Gly (SEQ ID NO:41) was assembled manually by standard Fmoc chemistry using Rink AM resin. Briefly, 3.6 grams of Rink AM resin was swollen in DCM for 14 h and then washed four times with DMF. Removal of Fmoc was carried out in 20% piperidine in DMF for 20 min at room temperature and washed several times with DMF. Ninhydrin test was negative. Stepwise chain assembly started from the C-terminal end of the linear peptide and was accomplished in nine major steps. In step 1, three equivalents of protected amino acid Fmoc-Gly were activated with DIC/HOBt in DMF, and coupled to the Fmoc-removed Rink AM resin above for 2 h at room temperature followed by Fmoc removal using 20% piperidine in DMF for 20 min. In step 2, three equivalents of Fmoc-Lys(iPr,Boc) were activated with DCC/HOBt in DMF and coupled to the deprotected resin from step 1. Appropriate steps were continued using Fmoc-protected amino acids, respectively, until step 10, the addition of phenylacetyl. Phenylacetylation was carried out using three equivalents of phenylacetyl chloride in 20% DIEA/DMF for 50 min. No Fmoc removal was needed afterward.

The finished peptide was simultaneously deprotected and cleaved from the resin using 36 mL of a cleavage cocktail of TFA/EDT/TIS/H$_2$O/thioanisole/phenol (per 100 mL of solution contains 81.5 mL TFA, 2.5 mL EDT, 1.0 mL TIS, 5.0 mL H$_2$O, 5.0 mL thioanisole, and 5.0 grams phenol) for 70 min at room temperature. To the cleavage mixture was added eight volumes of methyl t-butyl ether. The crude peptide precipitates were separated by centrifugation at 3000 rpm for 3 min. The crude peptide precipitates were washed three times with methyl t-butyl ether. The crude peptide was then dissolved in aqueous acetonitrile and lyophilized.

The lyophilized crude peptide was dissolved in water containing 20% acetic acid at 0.5 mg/mL (500 mg of crude peptide in one liter). Under stirring, adding 0.03% mole/L iodine solution to the peptide solution until the solution becomes pale yellow. Cyclization was complete within 0.5 h in dark as monitored by mass spectroscopy. The cyclized final product was purified using a reverse-phased preparative column Daisogel (50×250 mm, 8 µm); mobile phases—Solvent A: 0.1% TFA water; Solvent B: 0.1% TFA acetonitrile. Fractions containing the target product were combined and lyophilized (a TFA salt).

Salt exchange as described above afforded a peptide in acetate salt. Analytical HPLC purity of the final peptide product 95.67%; MW cal.: 1324.67; MW obs.: 1324.65.

Example 16: Ac-cyclo[hCys-Tyr-Lys(iPr)-(D-Arg)-2Nal-Gly-Cys]-Lys(iPr)-Gly-NH(Et) (MLB-026) (SEQ ID NO: 42): The sequence hCys(Trt)-Tyr(tBu)-Lys(iPr,Boc)-(D-Arg(Pbf))-2Nal-Gly-Cys(Trt)-Lys(iPr,Boc)-Gly (SEQ ID NO:43) was assembled by standard Fmoc chemistry using 2-Chloro-trityl chloride resin. Briefly, 4.0 grams of the resin was swollen in DCM for 2 h, washed four times with DMF and then once with DCM. Based on a substitution of 0.4 mmole/gram, the loading of the first residue Fmoc-Gly was carried out in DCM using four equivalents of amino acid activated with five equivalents of DIEA. The coupling at room temperature for 1.5 h was followed by capping of the unreacted substitution sites with methanol/DIEA (1:1, v/v, 24 mL) for 30 min. Removal of Fmoc protection was carried out in 20% piperidine in DMF for 20 min at room temperature and washed several times with DMF. Ninhydrin test was negative. Stepwise chain assembly of the linear peptide was continued and accomplished in a total of 9 major steps.

After the coupling of Fmoc-Gly, in step 2 three equivalents of Fmoc-Lys(iPr, Boc) were activated with DCC/HOBt in DMF and coupled to the deprotected resin from step 1 for 2 h at room temperature. Appropriate steps were then continued using corresponding Fmoc-protected amino acids, respectively, until step 9, the coupling of Fmoc-hCys(Trt). For step 9, Fmoc at the N-terminal end was removed using 20% piperidine in DMF and acetylation of the α-amino group was carried out with 22 mL of a mixture of acetic anhydride/DIEA/DMF (1:1:4, v/v) for 30 min at room temperature.

The finished linear peptide acid was cleaved from the resin in a fully protected form by using 20% TFE in DCM (30 mL per gram of resin) for 90 min at room temperature. The cleavage solution was separated by filtration and a second cleavage was carried out using the same 20% TFE in DCM for 60 min. Resin was again removed by filtration and the two cleavage solutions were combined. The solvents were then removed and the residue was dried under vacuum to afford the crude, fully protected linear peptide acid, sequence Ac-hCys(Trt)-Tyr(tBu)-Lys(iPr, Boc)-(D-Arg(Pbf))-2Nal-Gly-Cys(Trt)-Lys(iPr, Boc)-Gly-OH C-terminal ethyl amination and side chain protection removal: The crude linear peptide acid was dissolved in dry DMF at 15 mg/mL. To the peptide acid solution was added three molar equivalents of HATU, 2,4,6-trimethylpyridine, and ethylamine, respectively (3:3:3, molar ratio). The ethyl amination reaction was accomplished within one hour as monitored by mass spectroscopy. The solvents were evaporated and the residue was dried under vacuum.

The side chain protections of the lyophilized crude linear peptide was removed using 10 mL of a cleavage cocktail of TFA/EDT/TIS/H$_2$O/thioanisole/phenol per gram of crude peptide material (per 100 mL of solution contains 81.5 mL TFA, 2.5 mL EDT, 1.0 mL TIS, 5.0 mL H$_2$O, 5.0 mL thioanisole, and 5.0 grams phenol) for 70 min at room temperature. To the cleavage mixture was added eight volumes of methyl t-butyl ether. The crude peptide precipitates were separated by centrifugation at 3000 rpm for 3 min. The crude peptide precipitates were washed three times with methyl t-butyl ether. The crude peptide was then dissolved in aqueous acetonitrile and lyophilized.

Cyclization: The lyophilized crude peptide was dissolved in 20% acetic acid at 0.5 mg/mL. Under stirring, add 0.03% mole/L iodine solution to the linear peptide solution until the peptide solution turns light yellow. The solution was protected from visible light during the cyclization. Cyclization was complete within 0.5 h as monitored by mass spectroscopy. The cyclized final product was purified using a reverse-phased preparative column Daisogel (50×250 mm, 8 μm) with mobile phases—A: 0.1% TFA water; B: 0.1% TFA acetonitrile. Fractions containing the target product were combined and lyophilized (a TFA salt).

Salt exchange as described above afforded a peptide in acetate salt. Analytical HPLC purity of the final peptide product 95.03%; MW cal.: 1276.62; MW obs.: 1276.65.

Example 17: cyclo[Mpa-Tyr-Lys(iPr)-(D-Arg)-2Nal-Gly-Cys]-Lys(iPr)-Lys(Ac)-NH(Et) (MLB-027) (SEQ ID NO: 44): The sequence Mpa(Trt)-Tyr(tBu)-Lys(iPr, Boc)-(D-Arg(Pbf))-2Nal-Gly-Cys(Trt)-Lys(iPr, Boc)-Lys(Ac) (SEQ ID NO:45) was assembled by standard Fmoc chemistry using 2-chlorotrityl chloride resin. Briefly, 4.0 grams of the resin was swollen in DCM for 2 h, washed four times with DMF and then once with DCM. Based on a substitution of 0.4 mmole/gram, the loading of the first residue Fmoc-Lys(Ac) was carried out in DCM using three equivalents of amino acid activated with DIEA. The coupling at room temperature for 1.5 h was followed by capping of the unreacted substitution sites with methanol/DIEA (1:1, v/v, 24 mL) for 30 min. Removal of Fmoc protection was carried out in 20% piperidine in DMF for 20 min at room temperature and washed several times with DMF. Ninhydrin test was negative. Stepwise chain assembly of the linear peptide was continued and accomplished in a total of 9 major steps.

After the coupling of Fmoc-Lys(Ac), in step 2 three equivalents of Fmoc-Lys(iPr, Boc) were activated with DCC/HOBt in DMF and coupled to the deprotected resin from step 1 for 2 h at room temperature. Appropriate steps were then continued using corresponding Fmoc-protected amino acids, respectively, until step 9, the coupling of 3-(tritylthio) propionic acid (Mpa(Trt)).

The finished linear peptide acid was cleaved from the resin in a fully protected form by using 20% TFE in DCM (30 mL per gram of resin) for 90 min at room temperature. The cleavage solution was separated by filtration and a second cleavage was carried out using the same 20% TFE in DCM for 60 min. Resin was again removed by filtration and the two cleavage solutions were combined. The solvents were then removed and the residue was dried under vacuum to afford the crude, fully protected linear peptide acid.

C-terminal ethyl amination and removal of side chain protections. The crude linear peptide acid was dissolved in dry DMF at 15 mg/mL. To the peptide acid solution was added three molar equivalents of HATU, 2,4,6-trimethylpyridine, and ethylamine, respectively. The ethyl amination reaction was accomplished within one hour as monitored by mass spectroscopy. The solvents were evaporated and the residues were dried under vacuum.

The side chain protections of the lyophilized crude linear peptide was removed using 10 mL of a cleavage cocktail of TFA/EDT/TIS/H$_2$O/thioanisole/phenol per gram of crude peptide material (per 100 mL of solution contains 81.5 mL TFA, 2.5 mL EDT, 1.0 mL TIS, 5.0 mL H$_2$O, 5.0 mL thioanisole, and 5.0 grams phenol) for 70 min at room temperature. To the cleavage mixture was added eight volumes of methyl t-butyl ether. The crude peptide precipitates were separated by centrifugation at 3000 rpm for 3 min. The crude peptide precipitates were washed three times with methyl t-butyl ether. The crude peptide was dissolved in aqueous acetonitrile and lyophilized.

Cyclization: The lyophilized crude peptide was dissolved in 20% acetic acid at 0.5 mg/mL. Under stirring, 0.03% mole/L iodine solution was added to the linear peptide solution until the peptide solution turned light yellow. The solution was protected from visible light during the cyclization. Cyclization was completed within 0.5 h as monitored by mass spectroscopy. The cyclized final product was purified using a reverse-phased preparative column Daisogel (50×250 mm, 8 μm) with mobile phases—A: 0.1% TFA water; B: 0.1% TFA acetonitrile. Fractions containing the target product were combined and lyophilized (a TFA salt).

Salt exchange as described above afforded a peptide in acetate salt. Analytical HPLC purity of the final peptide product 95.50%; MW cal.: 1318.70; MW obs.: 1318.80; peptide content 77.53%.

Example 18: cyclo[Mpa-Tyr-Lys(iPr)-(D-Arg)-2Nal-Gly-Cys]-Lys(iPr)-Lys(lauroyl)-NH(Et) (MLB-028) (SEQ ID NO: 46): The sequence Mpa(Trt)-Tyr(tBu)-Lys(iPr, Boc)-(D-Arg(Pbf))-2Nal-Gly-Cys(Trt)-Lys(iPr, Boc)-Lys(dde) (SEQ ID NO:47) was assembled by standard Fmoc chemistry using 2-chlorotrityl chloride resin. Briefly, 4.0 grams of the resin was swollen in DCM for 2 h, washed four times with DMF and then once with DCM. Based on a substitution of 0.4 mmole/gram, the loading of the first residue Fmoc-Lys(Dde) (Dde: 1-(4,4-Dimethyl-2,6-Dioxocyclohexylidene) Ethyl) was carried out in DCM using three equivalents of amino acid activated with DIEA. The coupling at room temperature for 1.5 h was followed by capping of the unreacted substitution sites with methanol/DIEA (1:1, v/v, 24 mL) for 30 min. Removal of Fmoc protection was carried out in 20% piperidine in DMF for 20 min at room temperature and washed several times with DMF. Ninhydrin test was negative. Stepwise chain assembly of the linear peptide was continued and accomplished in a total of 9 major steps.

After the coupling of 3-(tritylthio) propionic acid (Mpa (Trt)), Dde protection of the ε-amino of lysine side was removed with 5% hydrazine, 5 min at room temperature. Then the resin was washed three times with DMF. The hydrazine deprotection was repeated three times. After the last deprotection, the resin was washed five times with DMF, then to the deprotected resin was added 3 equivalents of lauric acid, activated with HOBt/DIC in DMF. The coupling was allowed to proceed for 60 min. The resin was then washed three times with DMF, and twice with DCM. The resin was dried under vacuum before cleavage.

The finished linear peptide acid was cleaved from the resin in a fully protected form by using 20% TFE in DCM (30 mL per gram of resin) for 90 min at room temperature. The cleavage solution was separated by filtration and a second cleavage was carried out using the same 20% TFE in DCM for 60 min. Resin was again removed by filtration and the two cleavage solutions were combined. The solvents were then removed and the residue was dried under vacuum to afford the crude, fully protected linear peptide acid.

C-terminal ethyl amination and removal of side chain protections. The crude linear peptide acid was dissolved in dry DMF at 15 mg/mL. To the peptide acid solution was added three molar equivalents of HATU, 2,4,6-trimethylpyridine, and ethylamine, respectively. The ethyl amination reaction was accomplished within one hour as monitored by mass spectroscopy. The solvents were evaporated and the residues were dried under vacuum.

The side chain protections of the lyophilized crude linear peptide was removed using 10 mL of a cleavage cocktail of TFA/EDT/TIS/H$_2$O/thioanisole/phenol per gram of crude peptide material (per 100 mL of solution contains 81.5 mL TFA, 2.5 mL EDT, 1.0 mL TIS, 5.0 mL H$_2$O, 5.0 mL thioanisole, and 5.0 grams phenol) for 70 min at room temperature. To the cleavage mixture was added eight volumes of methyl t-butyl ether. The crude peptide precipitates were separated by centrifugation at 3000 rpm for 3 min. The crude peptide precipitates were washed three times with methyl t-butyl ether. The crude peptide was then dissolved in aqueous acetonitrile and lyophilized.

Cyclization: The lyophilized crude peptide was dissolved in 20% acetic acid at 0.5 mg/mL. Under stirring, 0.03% mole/L iodine solution was added to the linear peptide solution until the peptide solution turned light yellow. The solution was protected from visible light during the cyclization. Cyclization was completed within 0.5 h as monitored by mass spectroscopy. The cyclized final product was purified using a reverse-phased preparative column Daisogel (50×250 mm, 8 μm) with mobile phases—A: 0.1% TFA water; B: 0.1% TFA acetonitrile. Fractions containing the target product were combined and lyophilized (a TFA salt).

Salt exchange as described above afforded a peptide in acetate salt. Analytical HPLC purity of the final peptide product 95.42%; MW cal.: 1458.97; MW obs.: 1458.75; peptide content 78.19%.

Example 19: cyclo[Mpa-Tyr-Lys(iPr)-(D-Arg)-2Nal-Gly-Cys]-Lys(iPr)-Lys(palmitoyl)-NH(Et) (MLB-029) (SEQ ID NO: 48): The sequence Mpa(Trt)-Tyr(tBu)-Lys(iPr, Boc)-(D-Arg(Pbf))-2Nal-Gly-Cys(Trt)-Lys(iPr, Boc)-Lys(dde) (SEQ ID NO:49) was assembled by standard Fmoc chemistry using 2-chlorotrityl chloride resin. Briefly, 4.0 grams of the resin was swollen in DCM for 2 h, washed four times with DMF and then once with DCM. Based on a substitution of 0.4 mmole/gram, the loading of the first residue Fmoc-Lys(Dde) (Dde: 1-(4,4-Dimethyl-2,6-Dioxocyclohexylidene) Ethyl) was carried out in DCM using three equivalents of amino acid activated with DIEA. The coupling at room temperature for 1.5 h was followed by capping of the unreacted substitution sites with methanol/DIEA (1:1, v/v, 24 mL) for 30 min. Removal of Fmoc protection was carried out in 20% piperidine in DMF for 20 min at room temperature and washed several times with DMF. Ninhydrin test was negative. Stepwise chain assembly of the linear peptide was continued and accomplished in a total of 9 major steps.

After the coupling of 3-(tritylthio) propionic acid (Mpa (Trt)), Dde protection of the ε-amino of lysine side was removed with 5% hydrazine, 5 min at room temperature. Then the resin was washed three times with DMF. This hydrazine deprotection was repeated three times. After the last deprotection, the resin was washed five times with DMF. To the deprotected resin was added 3 equivalents of palmitic acid, and was activated with HOBt/DIC in DMF. The coupling was allowed to proceed for 60 min. The resin was then washed three times with DMF, and twice with DCM. The resin was dried under vacuum before cleavage.

The finished linear peptide acid was cleaved from the resin in a fully protected form by using 20% TFE in DCM (30 mL per gram of resin) for 90 min at room temperature. The cleavage solution was separated by filtration and a second cleavage was carried out using the same 20% TFE in DCM for 60 min. Resin was again removed by filtration and the two cleavage solutions were combined. The solvents were then removed and the residue was dried under vacuum to afford the crude, fully protected linear peptide acid.

C-terminal ethyl amination and removal of side chain protections. The crude linear peptide acid was dissolved in dry DMF at 15 mg/mL. To the peptide acid solution was added three molar equivalents of HATU, 2,4,6-trimethylpyridine, and ethylamine, respectively. The ethyl amination reaction was accomplished within one hour as monitored by mass spectroscopy. The solvents were evaporated and the residues were dried under vacuum.

The side chain protections of the lyophilized crude linear peptide was removed using 10 mL of a cleavage cocktail of TFA/EDT/TIS/H$_2$O/thioanisole/phenol per gram of crude peptide material (per 100 mL of solution contains 81.5 mL TFA, 2.5 mL EDT, 1.0 mL TIS, 5.0 mL H$_2$O, 5.0 mL thioanisole, and 5.0 grams phenol) for 70 min at room temperature. To the cleavage mixture was added eight volumes of methyl t-butyl ether. The crude peptide precipitates were separated by centrifugation at 3000 rpm for 3 min. The crude peptide precipitates were washed three times with methyl t-butyl ether. The crude peptide was then dissolved in aqueous acetonitrile and lyophilized.

Cyclization: The lyophilized crude peptide was dissolved in 20% acetic acid at 0.5 mg/mL. Under stirring, 0.03% mole/L iodine solution was added to the linear peptide solution until the peptide solution turns light yellow. The solution was protected from visible light during the cyclization. Cyclization was completed within 0.5 h as monitored by mass spectroscopy. The cyclized final product was purified using a reverse-phased preparative column Daisogel (50×250 mm, 8 μm) with mobile phases—A: 0.1% TFA water; B: 0.1% TFA acetonitrile. Fractions containing the target product were combined and lyophilized (a TFA salt).

Salt exchange as described above afforded a peptide in acetate salt. Analytical HPLC purity of the final peptide product 95.31%; MW cal.: 1515.08; MW obs.: 1515.00.

Example 20:

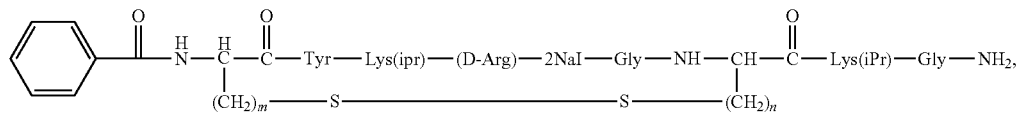

where m and n are 1 (MLB-030) (SEQ ID NO:50): The sequence Cys(Trt)-Tyr(tBu)-Lys(iPr,Boc)-(D-Arg(Pbf))-2Nal-Gly-Cys(Trt)-Lys(iPr,Boc)-Gly (SEQ ID NO:51) was assembled by standard Fmoc chemistry using Rink AM resin. Briefly, 3.6 grams of Rink AM resin was swollen in DCM for 14 h and then washed four times with DMF. Removal of Fmoc was carried out in 20% piperidine in DMF for 20 min at room temperature and washed several times with DMF. Ninhydrin test was negative. Stepwise chain assembly started from the C-terminal end of the linear peptide and was accomplished in nine major steps. In step 1, three equivalents of protected amino acid Fmoc-Gly were activated with DIC/HOBt in DMF, and coupled to the Fmoc-removed Rink AM resin above for 2 h at room temperature. The coupling was followed by capping of the unreacted substitution sites with methanol/DIEA (1:1, v/v, 24 mL) for 30 min. Removal of Fmoc protection was carried out in 20% piperidine in DMF for 20 min at room temperature and washed several times with DMF. Ninhydrin test was negative. This was followed by Fmoc removal using 20% piperidine in DMF for 20 min. In step 2, three equivalents of Fmoc-Lys(iPr, Boc) were activated with DCC/HOBt in DMF and coupled to the deprotected resin from step 1.

Appropriate steps were continued using Fmoc-protected amino acids, respectively, until step 10, the coupling of benzoic acid, which was carried out just like an amino acid as previous steps. For step 10, no Fmoc removal was carried out. The finished peptide was simultaneously deprotected and cleaved from the resin using 36 mL of a cleavage cocktail of TFA/EDT/TIS/H$_2$O/thioanisole/phenol (per 100 mL of solution contains 81.5 mL TFA, 2.5 mL EDT, 1.0 mL TIS, 5.0 mL H$_2$O, 5.0 mL thioanisole, and 5.0 grams phenol) for 70 min at room temperature. To the cleavage mixture was added eight volumes of methyl t-butyl ether. The crude peptide precipitates were separated by centrifugation at 3000 rpm for 3 min. The crude peptide precipitates were washed three times with methyl t-butyl ether. The crude peptide was then dissolved in aqueous acetonitrile and lyophilized.

The crude lyophilized linear peptide was used directly in the following cyclization reaction. One equivalent lyophilized crude peptide was added to a solution pre-prepared as following: 1.3 equivalents of 1,2-bisbromomethyl benzene was dissolved in acetonitrile at 5 mg/mL. Sonication can be used to speed up dissolution. The solution of 1,2-bisbromomethyl benzene was mixed with an equal volume of 15 mM of ammonium bicarbonate aqueous solution before adding the crude linear peptide to a final concentration of 1.5 mg/mL. The reaction was allowed to proceed with stirring for an hour. MS monitoring confirmed cyclization was complete.

The cyclized final product was purified using a reverse-phased preparative column Daisogel (50×250 mm, 8 μm); mobile phases—Solvent A: 0.1% TFA water; Solvent B: 0.1% TFA acetonitrile. Fractions containing the target product were combined and lyophilized (a TFA salt).

Salt exchange as described above afforded a peptide in acetate salt. Analytical HPLC purity of the final peptide product 97.04%; MW cal.: 1296.61; MW obs.: 1296.75; peptide content 78.15%.

Example 21:

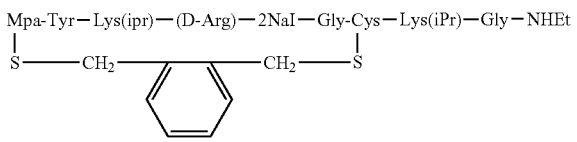

(MLB-031) (SEQ ID NO:52): The sequence Mpa(Trt)-Tyr (tBu)-Lys(iPr,Boc)-(D-Arg(Pbf))-2Nal-Gly-Cys(Trt)-Lys (iPr,Boc)-Gly (SEQ ID NO:53) was assembled by standard Fmoc chemistry using 2-Chloro-trityl chloride resin. Briefly, 4.0 grams of the resin was swollen in DCM for 2 h, washed four times with DMF and then once with DCM. Based on a substitution of 0.4 mmole/gram, the loading of the first residue Fmoc-Gly was carried out in DCM using four equivalents of amino acid activated with five equivalents of DIEA. The coupling at room temperature for 1.5 h was followed by capping of the unreacted substitution sites with methanol/DIEA (1:1, v/v, 24 mL) for 30 min. Removal of Fmoc protection was carried out in 20% piperidine in DMF for 20 min at room temperature and washed several times with DMF. Ninhydrin test was negative. Stepwise chain assembly of the linear peptide was continued and accomplished in a total of 9 major steps.

After the coupling of Fmoc-Gly, in step 2 three equivalents of Fmoc-Lys(iPr, Boc) were activated with DCC/HOBt in DMF and coupled to the deprotected resin from step 1 for 2 h at room temperature. Appropriate steps were then continued using corresponding Fmoc-protected amino acids, respectively, until step 9, the coupling of Mpa(Trt). No Fmoc removal was carried out after the coupling at this step.

The finished linear peptide acid was cleaved from the resin in a fully protected form by using 20% TFE in DCM (30 mL per gram of resin) for 90 min at room temperature. The cleavage solution was separated by filtration and a second cleavage was carried out using the same 20% TFE in DCM for 60 min. Resin was again removed by filtration and the two cleavage solutions were combined. The solvents were then removed and the residue was dried under vacuum to afford the crude, fully protected linear peptide acid, sequence Mpa(Trt)-Tyr(tBu)-Lys(iPr, Boc)-(D-Arg(Pbf))-2Nal-Gly-Cys(Trt)-Lys(iPr, Boc)-Gly-OH C-terminal ethyl amination and side chain protection removal: The crude linear peptide acid was dissolved in dry DMF at 15 mg/mL. To the peptide acid solution was added three molar equivalents of HATU, 2,4,6-trimethylpyridine, and ethylamine, respectively (3:3:3, molar ratio). The ethyl amination reaction was accomplished within one hour as monitored by mass spectroscopy. The solvents were evaporated and the residues were dried under vacuum.

The side chain protections of the lyophilized crude linear peptide was removed using 10 mL of a cleavage cocktail of TFA/EDT/TIS/H$_2$O/thioanisole/phenol per gram of crude peptide material (per 100 mL of solution contains 81.5 mL TFA, 2.5 mL EDT, 1.0 mL TIS, 5.0 mL H$_2$O, 5.0 mL thioanisole, and 5.0 grams phenol) for 70 min at room temperature. To the cleavage mixture was added eight volumes of methyl t-butyl ether. The crude peptide precipitates were separated by centrifugation at 3000 rpm for 3 min. The crude peptide precipitates were washed three times with methyl t-butyl ether. The crude linear peptide was then dissolved in aqueous acetonitrile and lyophilized.

Cyclization: One equivalent lyophilized crude peptide was added to a solution pre-prepared as following: 1.3 equivalents of 1,2-bisbromomethyl benzene was dissolved in acetonitrile at 5 mg/mL. Sonication can be used to speed up dissolution. The solution of 1,2-bisbromomethyl benzene was mixed with an equal volume of 15 mM of ammonium bicarbonate aqueous solution before adding the crude linear peptide to a final concentration of 1.5 mg/mL. The reaction was allowed to proceed with stirring for an hour. MS monitoring confirmed cyclization was complete.

The cyclized final product was purified using a reverse-phased preparative column Daisogel (50×250 mm, 8 μm); mobile phases—Solvent A: 0.1% TFA water; Solvent B: 0.1% TFA acetonitrile. Fractions containing the target product were combined and lyophilized (a TFA salt).

Salt exchange as described above afforded a peptide in acetate salt. Analytical HPLC purity of the final peptide product 97.59%; MW cal.: 1309.69; MW obs.: 1309.20.

Example 22:

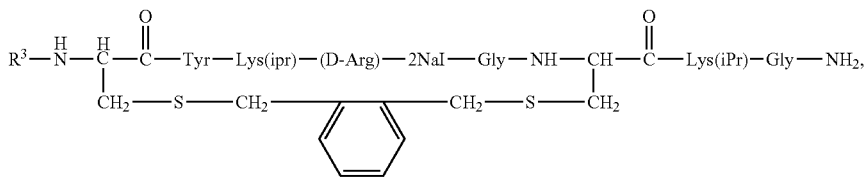

where R³ is Acyl (MLB-032) (SEQ ID NO:54): The sequence Cys(Trt)-Tyr(tBu)-Lys(iPr,Boc)-(D-Arg(Pbf))-2Nal-Gly-Cys(Trt)-Lys(iPr,Boc)-Gly (SEQ ID NO:55) was assembled by standard Fmoc chemistry using Rink AM resin. Briefly, 3.6 grams of Rink AM resin was swollen in DCM for 14 h and then washed four times with DMF. Removal of Fmoc was carried out in 20% piperidine in DMF for 20 min at room temperature and washed several times with DMF. Ninhydrin test was negative. Stepwise chain assembly started from the C-terminal end of the linear peptide and was accomplished in nine major steps. In step 1, three equivalents of protected amino acid Fmoc-Gly were activated with DIC/HOBt in DMF, and coupled to the Fmoc-removed Rink AM resin above for 2 h at room temperature. Ninhydrin test was negative. This was followed by Fmoc removal using 20% piperidine in DMF for 20 min. In step 2, three equivalents of Fmoc-Lys(iPr, Boc) were activated with DCC/HOBt in DMF and coupled to the deprotected resin from step 1. Appropriate steps were continued using Fmoc-protected amino acids, respectively. After the coupling of last residue Fmoc-Cys(Trt), Fmoc was removed using 20% piperidine in DMF for 20 min. N-terminal acetylation was carried out with 22 mL of a mixture of acetic anhydride/DIEA/DMF (1:1:4, v/v/v) for 30 min at room temperature. The resin was then washed with DMF three time and then with DCM twice, dried under vacuum.

The finished peptide was deprotected and cleaved from the dry resin using 36 mL of a cleavage cocktail of TFA/EDT/TIS/H₂O/thioanisole/phenol (per 100 mL of solution contains 81.5 mL TFA, 2.5 mL EDT, 1.0 mL TIS, 5.0 mL H₂O, 5.0 mL thioanisole, and 5.0 grams phenol) for 70 min at room temperature. To the cleavage mixture was added eight volumes of methyl t-butyl ether. The crude peptide precipitates were separated by centrifugation at 3000 rpm for 3 min. The crude peptide precipitates were washed three times with methyl t-butyl ether. The crude peptide was then dissolved in aqueous acetonitrile and lyophilized.

One equivalent lyophilized crude peptide was added to a solution pre-prepared as following: 1.3 equivalents of 1,2-bisbromomethyl benzene was dissolved in acetonitrile at 5 mg/mL. Sonication can be used to speed up dissolution. The solution of 1,2-bisbromomethyl benzene was mixed with an equal volume of 15 mM of ammonium bicarbonate aqueous solution before adding the crude linear peptide to a final concentration of 1.5 mg/mL. The reaction was allowed to proceed with stirring for an hour. MS monitoring confirmed cyclization was complete.

The cyclized final product was purified using a reverse-phased preparative column Daisogel (50×250 mm, 8 μm); mobile phases—Solvent A: 0.1% TFA water; Solvent B: 0.1% TFA acetonitrile. Fractions containing the target product were combined and lyophilized (a TFA salt).

Salt exchange as described above afforded a peptide in acetate salt. Analytical HPLC purity of the final peptide product 97.59%; MW cal.: 1338.70; MW obs.: 1338.60; peptide content 82.22%.

Example 23:

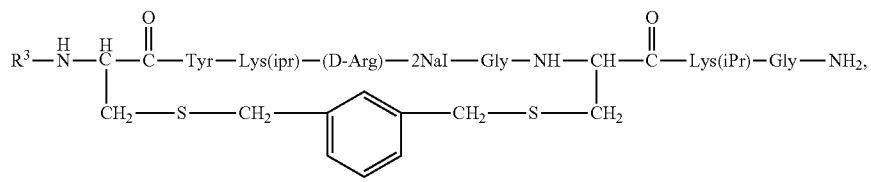

where R³ is acyl (MLB-033) (SEQ ID NO:56): The sequence Cys(Trt)-Tyr(tBu)-Lys(iPr,Boc)-(D-Arg(Pbf))-2Nal-Gly-Cys(Trt)-Lys(iPr,Boc)-Gly (SEQ ID NO:57) was assembled by standard Fmoc chemistry using Rink AM resin. Briefly, 3.6 grams of Rink AM resin was swollen in DCM for 14 h and then washed four times with DMF. Removal of Fmoc was carried out in 20% piperidine in DMF for 20 min at room temperature and washed several times with DMF. Ninhydrin test was negative. Stepwise chain assembly started from the C-terminal end of the linear peptide and was accomplished in nine major steps. In step 1, three equivalents of protected amino acid Fmoc-Gly were activated with DIC/HOBt in DMF, and coupled to the Fmoc-removed Rink AM resin above for 2 h at room temperature. Ninhydrin test was negative. This was followed by Fmoc removal using 20% piperidine in DMF for 20 min. In step 2, three equivalents of Fmoc-Lys(iPr, Boc) were activated with DCC/HOBt in DMF and coupled to the deprotected resin from step 1. Appropriate steps were continued using Fmoc-protected amino acids, respectively. After the coupling of last residue Fmoc-Cys(Trt), Fmoc was removed using 20% piperidine in DMF for 20 min. N-terminal acetylation was carried out with 22 mL of a mixture of acetic anhydride/DIEA/DMF (1:1:4, v/v/v) for 30 min at room temperature. The resin was then washed with DMF three time and then with DCM twice, dried under vacuum.

The finished peptide was deprotected and cleaved from the dry resin using 36 mL of a cleavage cocktail of TFA/EDT/TIS/H$_2$O/thioanisole/phenol (per 100 mL of solution contains 81.5 mL TFA, 2.5 mL EDT, 1.0 mL TIS, 5.0 mL H$_2$O, 5.0 mL thioanisole, and 5.0 grams phenol) for 70 min at room temperature. To the cleavage mixture was added eight volumes of methyl t-butyl ether. The crude peptide precipitates were separated by centrifugation at 3000 rpm for 3 min. The crude peptide precipitates were washed three times with methyl t-butyl ether. The crude peptide was then dissolved in aqueous acetonitrile and lyophilized.

One equivalent lyophilized crude peptide was added to a solution pre-prepared as following: 1.3 equivalents of 1,3-bisbromomethyl benzene was dissolved in acetonitrile at 5 mg/mL. Sonication can be used to speed up dissolution. The solution of 1,3-bisbromomethyl benzene was mixed with an equal volume of 15 mM of ammonium bicarbonate aqueous solution before adding the crude linear peptide to a final concentration of 1.5 mg/mL. The reaction was allowed to proceed with stirring for an hour. MS confirmed cyclization was complete.

The cyclized final product was purified using a reverse-phased preparative column Daisogel (50×250 mm, 8 mm); mobile phases—Solvent A: 0.1% TFA water; Solvent B: 0.1% TFA acetonitrile. Fractions containing the target product were combined and lyophilized (a TFA salt).

Salt exchange as described above afforded a peptide in acetate salt. Analytical HPLC purity of the final peptide product 95.23%; MW cal.: 1338.82; MW obs.: 1338.45.

Human CXCR4/[125I]-SDF-1α Binding Inhibition Assay: Human chemokine receptor CXCR4 expressed in Chem-1 cells were used in modified HEPES buffer pH 7.4. A 0.5 µg (Membrane protein may change from lot to lot, the concentration used were adjusted as necessary), aliquot was incubated with 0.03 nM [125I]SDF-1α for 90 minutes at 25° C. Non-specific binding was estimated in the presence of 30 nM SDF-1α. Membranes were filtered and washed, filters were then counted to determine [125I]SDF-1α specifically bound. Compounds were screened starting at 10 µM with 11-point dilutions (Valenzuela-Fernandez A, et al. *J Biol Chem.* 277(18):15677, 2002). The CXCR4 binding data together with their physical characterizations are shown in the table below.

TABLE 1

Characterization and Binding Activities of the Exemplified Peptides

| *Ex. No. | MLB | Cal. MW (Da) | Obs. MW (Da) | HPLC purity(%) | Peptide cont.(%) | Binding IC$_{50}$(nM) | Binding K$_b$(nM) |
|---|---|---|---|---|---|---|---|
| 1 | MLB-001 | 1353.49 | 1353.45 | 96.64 | 82.88 | 24.0 | 7.3 |
| 2 | MLB-002 | 1366.93 | 1367.70 | 98.78 | 83.55 | 0.92 | 0.28 |
| 3 | MLB-003 | 1381.35 | 1381.80 | 98.14 | 85.26 | 0.98 | 0.30 |
| 4 | MLB-004 | 1366.83 | 1367.25 | 97.02 | 83.77 | 0.70 | 0.21 |
| 5 | MLB-011 | 1353.49 | 1353.00 | 96.05 | 83.51 | >>1000 | >>1000 |
| 6 | MLB-012 | 1408.69 | 1409.10 | 96.54 | 84.46 | 1.50 | 0.45 |
| 7 | MLB-014 | 1204.51 | 1205.25 | 95.71 | 81.60 | 0.64 | 0.19 |
| 8 | MLB-008 | 1430.43 | 1431.00 | 96.44 | 84.33 | 0.95 | 0.29 |
| 9 | MLB-009 | 1451.84 | 1452.60 | 96.38 | 83.88 | 0.61 | 0.18 |
| 10 | MLB-010 | 1247.61 | 1248.00 | 96.13 | 81.02 | 0.56 | 0.17 |
| 11 | MLB-021 | 1310.64 | 1310.70 | 95.98 | 78.48 | 0.42 | 0.13 |
| 12 | MLB-022 | 1310.64 | 1310.55 | 95.64 | 69.25 | 0.71 | 0.21 |
| 13 | MLB-023 | 1296.61 | 1296.75 | 97.04 | 78.15 | 3.40 | 1.00 |
| 14 | MLB-024 | 1338.69 | 1338.90 | 97.59 | n/a | 1.30 | 0.39 |
| 15 | MLB-025 | 1324.67 | 1324.65 | 95.67 | n/a | 0.84 | 0.25 |
| 16 | MLB-026 | 1276.62 | 1276.65 | 95.03 | n/a | 0.89 | 0.27 |
| 17 | MLB-027 | 1318.70 | 1318.80 | 95.50 | 77.53 | 0.48 | 0.15 |
| 18 | MLB-028 | 1458.97 | 1458.75 | 96.42 | 78.19 | 8.20 | 2.50 |
| 19 | MLB-029 | 1515.08 | 1515.00 | 95.31 | n/a | 11.00 | 3.20 |
| 20 | MLB-030 | 1400.76 | 1400.85 | 95.60 | 73.80 | 1.30 | 0.39 |
| 21 | MLB-031 | 1309.69 | 1309.20 | 96.54 | n/a | n/a | n/a |
| 22 | MLB-032 | 1338.70 | 1338.60 | 97.59 | 82.22 | 0.40 | 0.12 |
| 23 | MLB-033 | 1338.82 | 1338.45 | 95.23 | n/a | 3.3 | 0.99 |

*Ex. Nos. 1-23 corresponds to the number of each Example in the specification.

Tumor Cell Migration and Invasion Assays: Cell migration is a multistep process that is a fundamental component of many biological and pathological processes such as embryonic development, tissue re-organization, angiogenesis, immune cell trafficking, chronic inflammation, wound healing and tumor metastasis.

Cell invasion is one of the hallmarks of cancer. It is related to cell migration and plays a key role in metastasis. Metastasis is the leading reason for the resultant mortality of patients with cancer. The ability of tumor cells to form a metastatic tumor is primarily determined by the cell's ability to change and reorganize its cellular morphology, and to degrade the extracellular matrix (ECM).

Increased cell migration and invasion indicate an enhanced metastatic potential of the human cancer cells. Thus, the purpose of this experiment was to determine the ability of compounds of the invention to inhibit the migration and invasion of triple negative breast cancer (TNBC) and non-small cell lung cancer (NSCLC) cells. Such inhibition indicates therapeutic activity against tumor metastasis of TNBC and NSCLC.

Migration assay via an IncuCyte system: The IncuCyte® ZOOM System (Essen BioScience, Inc., Ann Arbor, Mich.) was used to kinetically monitor cell migration and invasion.

This automated system is an integrated live-cell imaging and analysis platform that enables real-time quantification of cell behavior (proliferation, motility, migration, invasion, and etc.) within the stable environment of cell culture incubator, eliminating the limitations of typical end point analysis. The experimental procedure is outlined below:
1. Cells were grown in DME/F12 or RPMI1640 medium supplement with 10% FBS.
2. Cells were seeded onto a 96-well tissue culture plate at such a density that after 24 hrs, the growing cells reached ~80-90% confluence as a monolayer. (MDA-MB-231: 50000/well; HCC1806:40000/well; A549: 50000/well)
3. Cells were starved (cultured with Serum free Medium (SFM)) for 2 hrs. A scratch was made in each well using a wound maker provided by Essen BioScience, Inc. The plate was then washed twice with PBS.
4. The cells were pretreated with DMSO (Control) or a peptide CXCR4-antagonist (200 nmol/L) in 100 µl Serum free Medium (SFM) for 2 hrs.
5. The culture medium was next replaced with fresh SFM (100 µl) with or without the ligand SDF-1α (100 ng/ml) combined with DMSO or the peptide CXCR4-antagonist (200 nmol/L).
6. The plates were then placed into an IncuCyte system and incubated at a regular cell culture incubator for 1-2 days. Data obtained through the IncuCyte scanning every 4 hrs were analyzed by the IncuCyte software, and the wound healing curves were generated.

Figure 3:
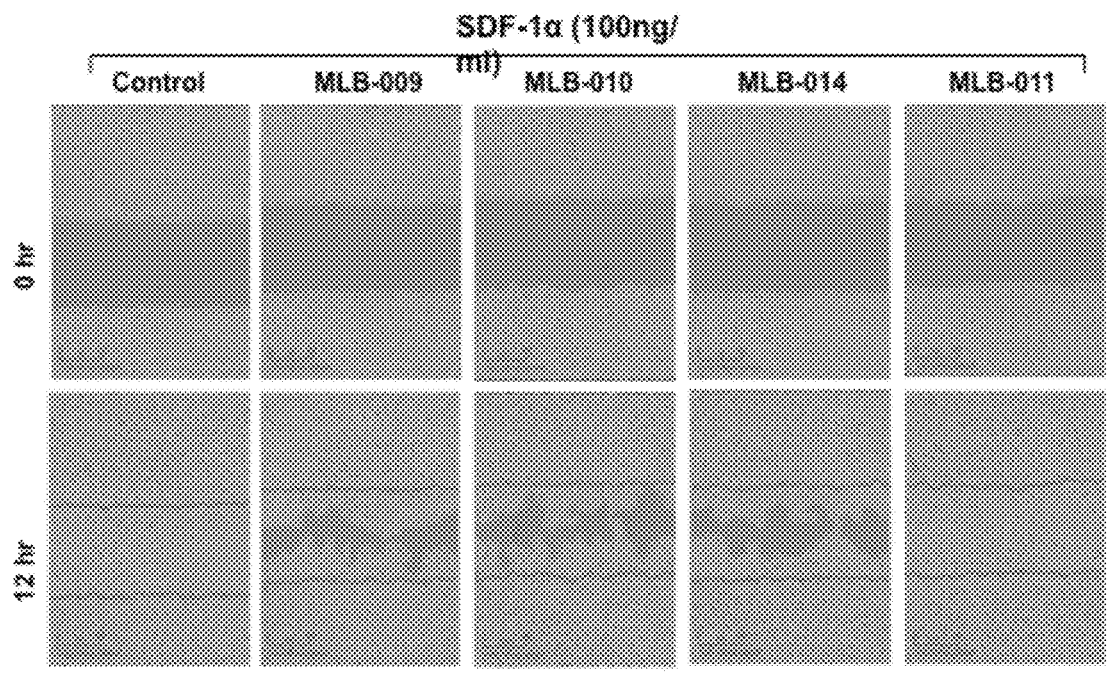
Figure 2:
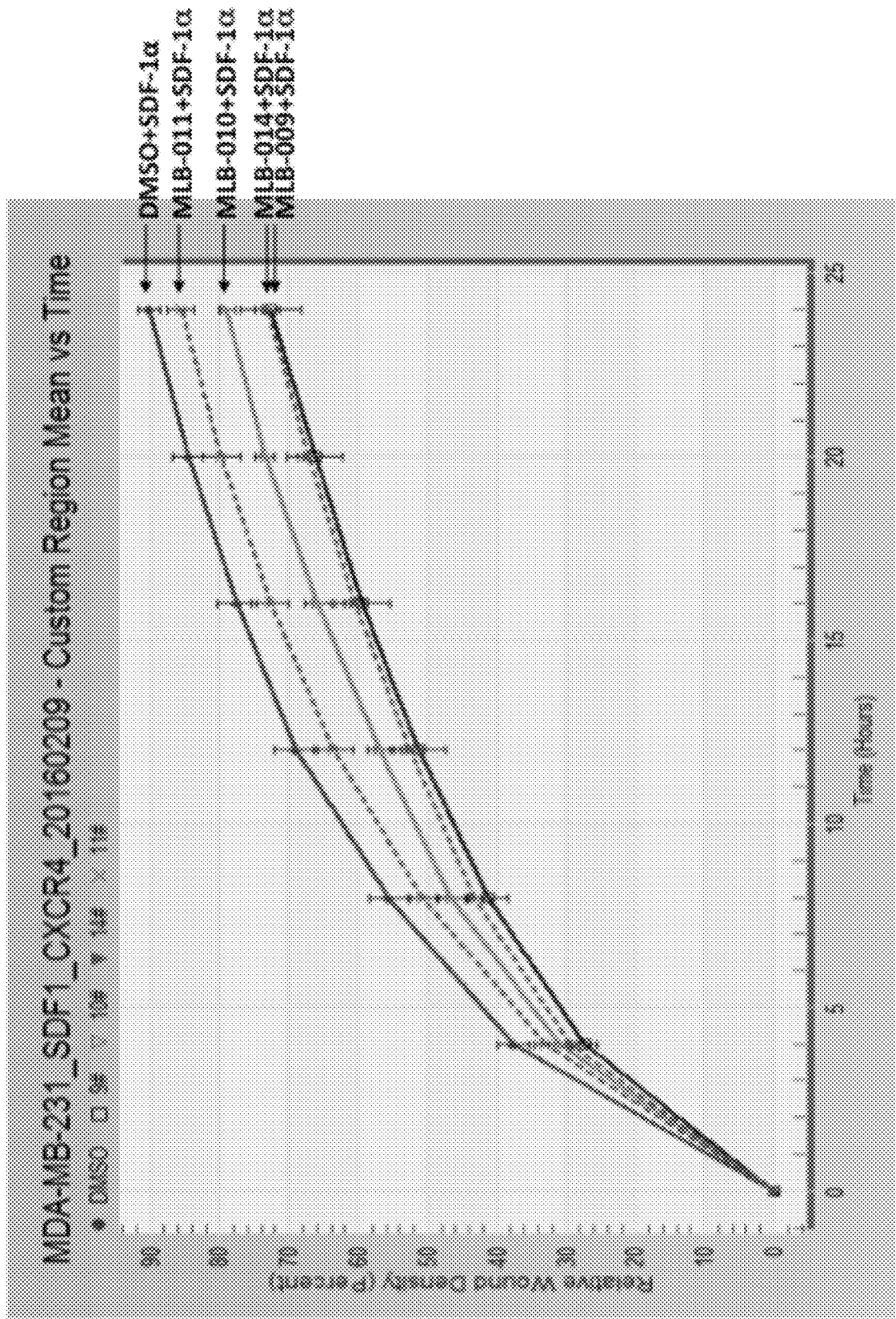
FIG. 2 is a graph showing quantification of the cell migration assays for MDA-MB-231 cells.
Figure 4:
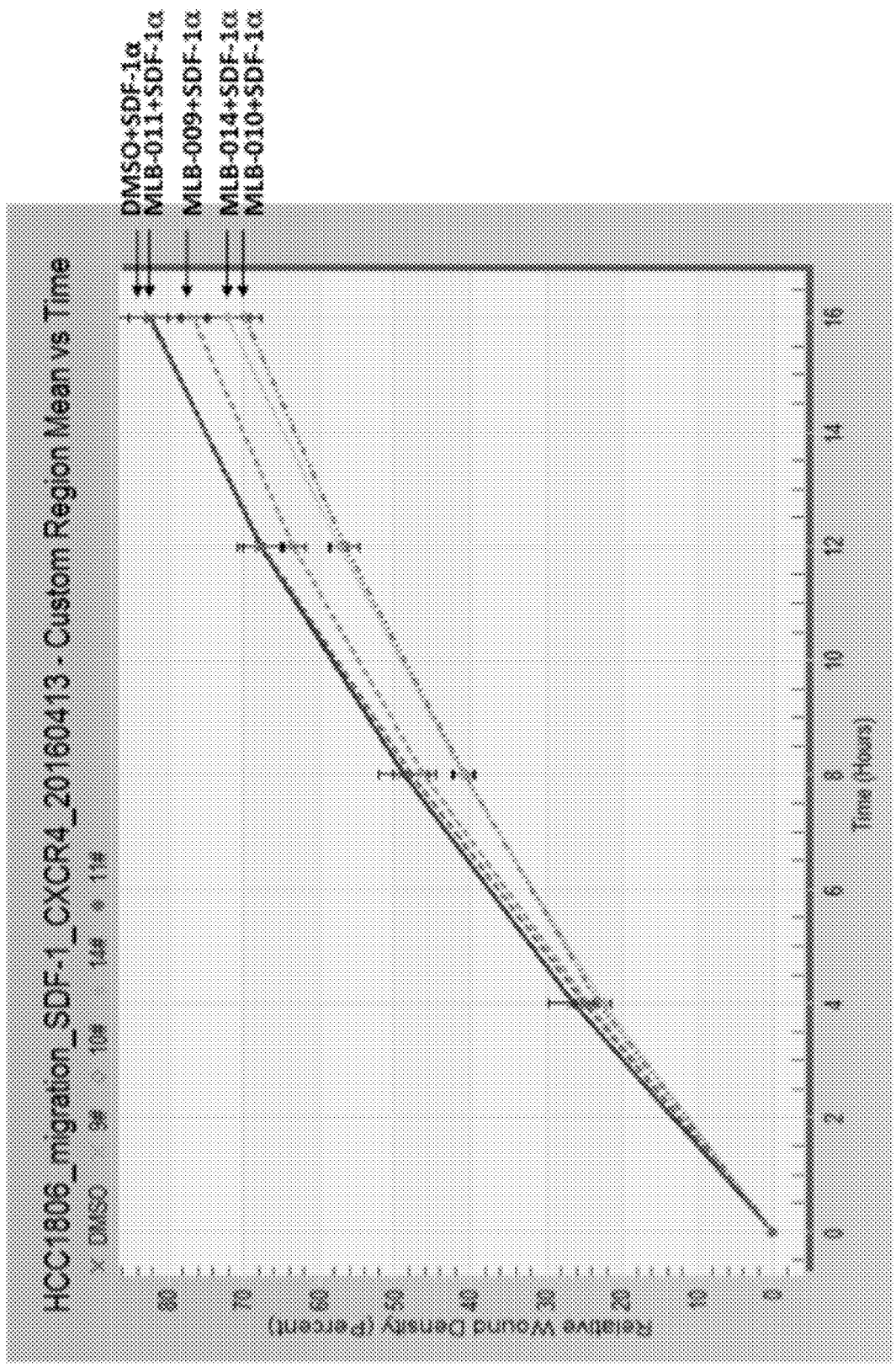
FIG. 4 is a graph showing the quantification of HCC1806 cell migration assays.

The assay data are reported in FIGS. 1-4. FIG. 1 shows that compounds of the invention were able to inhibit the ligand (SDF-1α)-induced cell migration in the TNBC MDA-MB-231 cells. MDA-MB-231 cells were analyzed by the cell migration assays described above. SDF-1α at 200 ng/ml was used. Concentration of the compounds of the invention (e.g., MLB-009, MLB-010, MLB-014, and MLB-011) used was 200 nmol/L. The green colors at 0 hr indicate the initial scratch area; at 12 or 16 hr, green colors indicate the remaining areas without cell migration. FIG. 2 is the quantification of the cell migration assays for MDA-MB-231 cells as described in FIG. 1. FIG. 3 shows that compounds of the invention also inhibit SDF-1α-induced HCC1806 cell migration. Another TNBC HCC1806 cell line was analyzed using the cell migration assay. SDF-1α was used at 100 ng/mL. Concentration of the compounds (MLB-009, MLB-010, MLB-014, and MLB-011) used was 200 nmol/L. The green colors at 0 hr indicate the initial scratch area; at 12 hr, green colors indicate the remaining areas without cell migration. FIG. 4 is the quantification of HCC1806 cell migration assays as described in FIG. 3.

Invasion assay via an IncuCyte system: The IncuCyte® ZOOM System (Essen BioScience, Inc., Ann Arbor, Mich.) was also used to kinetically monitor cancer cell invasion. Experimental procedure for this assay is provided below:
1. The matrigel diluted with SFM in 1:100 was added onto a 96-well tissue culture plate (50 µl/well). The plate was placed into a regular cell culture incubator overnight.
2. Cells grown in DME/F12 or RPMI1640 medium supplement with 10% FBS were seeded onto the 96-well plate described above. (MDA-MB-231:50000/well; HCC1806:40000/well; A549:50000/well)
3. On next day, cells were starved (cultured with SFM) for 2 hrs. A scratch was made in each well using a wound maker through the IncuCyte machine. The plate was then washed twice with PBS.
4. The cells were pretreated with DMSO (Control) or a compound of the invention (200 nmol/L) in 100 µl SFM for 2 hrs.
5. The cell culture medium was then replaced with Matrigel diluted with SFM in 1:20 ratio (50 µl/well). The plate was placed into the incubator for 1 hr.
6. Fresh SFM (100 µl) containing with or without SDF-1α (100 ng/ml) plus DMSO or the compound of the invention (200 nmol/L) was added into each well of the 96-well plate.
7. The plates were then placed into an IncuCyte system and incubated at a regular cell culture incubator for 1-2 days. Data obtained through the IncuCyte scanning every 4 hrs were analyzed by the IncuCyte software, and the cell invasion curves were generated.

Figure 5:
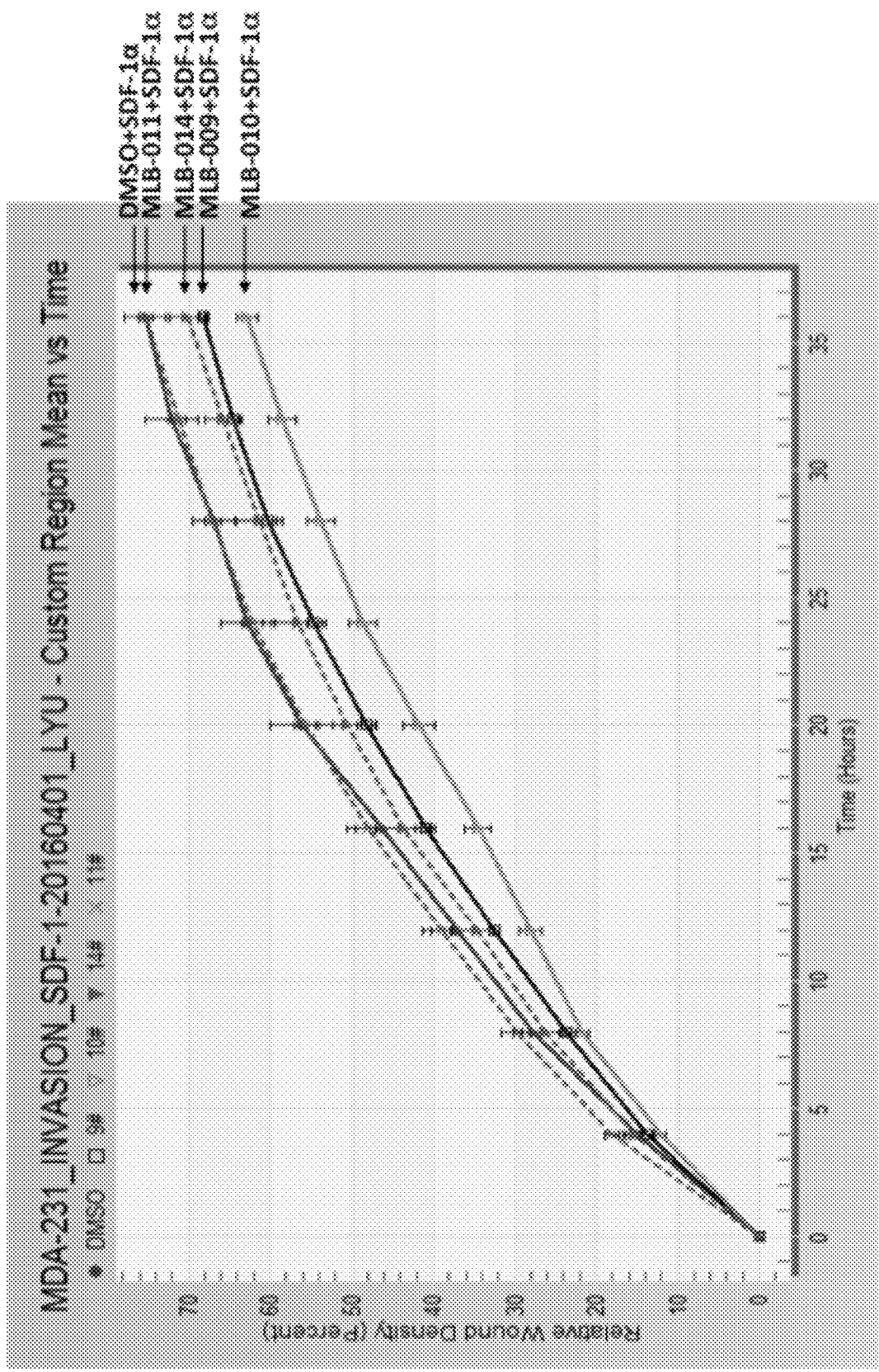
FIG. 5 is a graph showing the quantification of the cell invasion assays for MDA-MB-231 cells.
Figure 6:
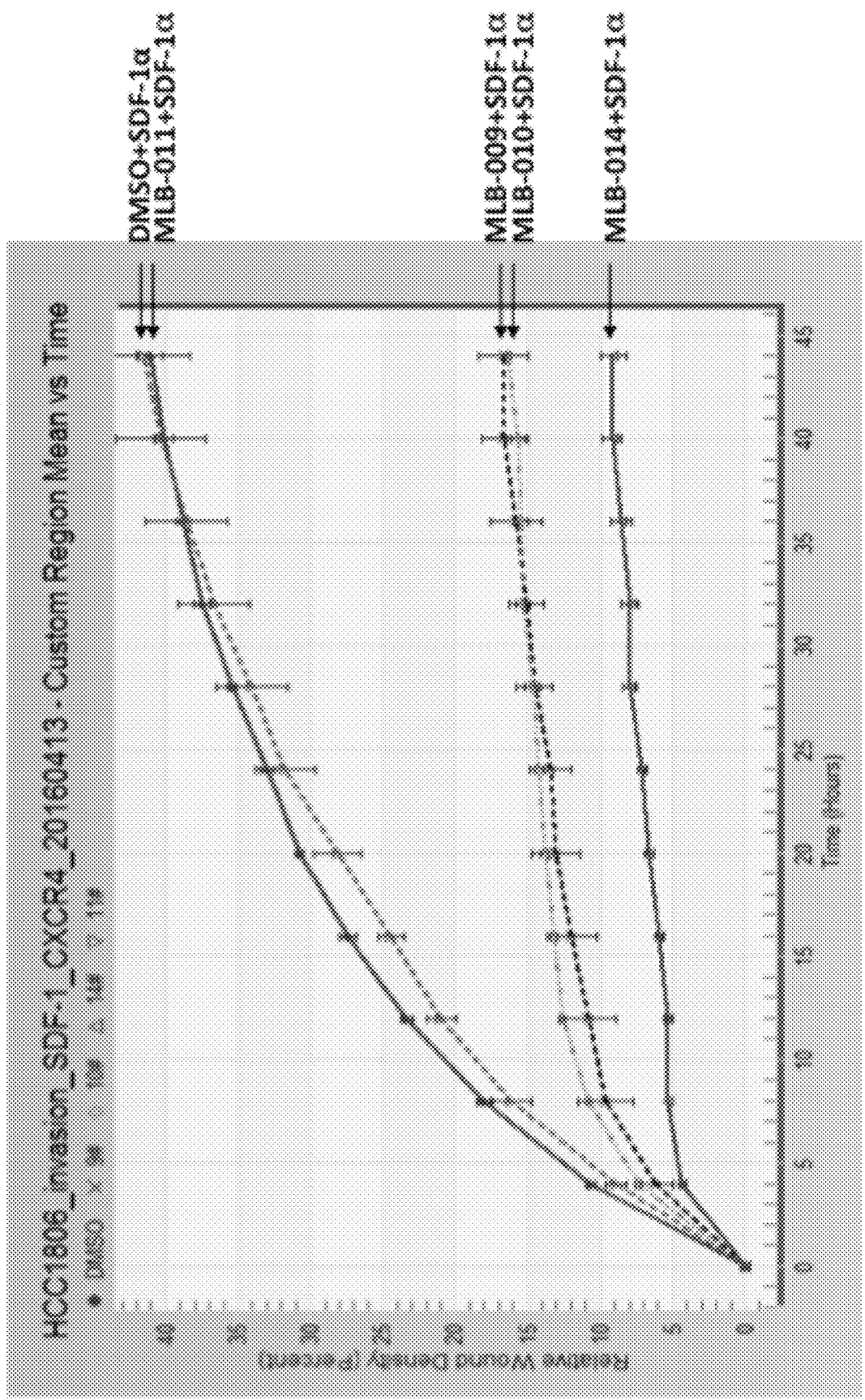
FIG. 6 is a graph showing the quantification of the cell invasion assays for HCC1806 cells.
Figure 7:
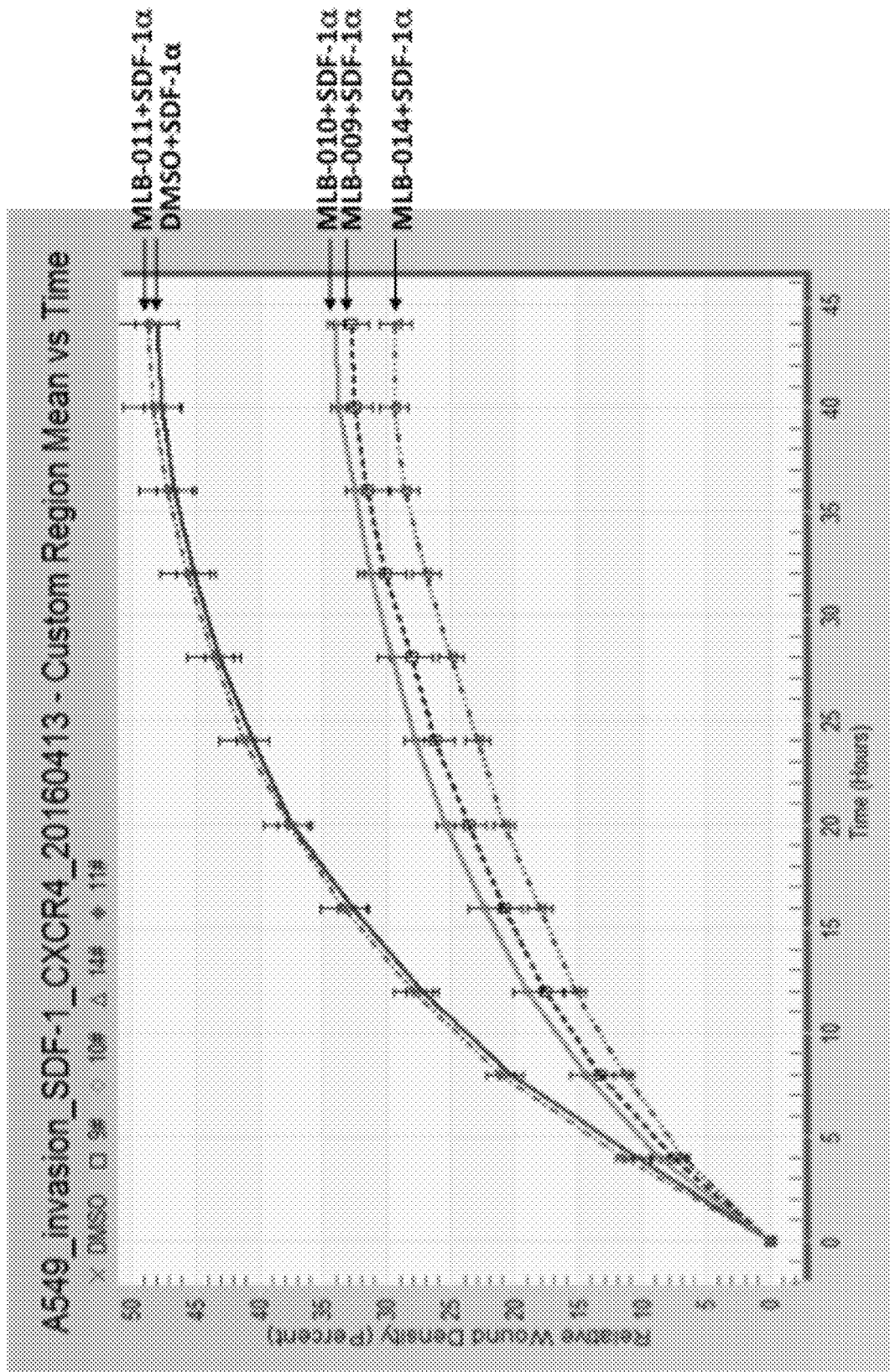
FIG. 7 is a graph showing the quantification of the cell invasion assays for the NSCLC A549 cells.

The data are reported in FIGS. 5-7. FIG. 5 is the quantification of the cell invasion assays for MDA-MB-231 cells. FIG. 6 is the quantification of the cell invasion assays for HCC1806 cells. FIG. 7 is the quantification of the cell invasion assays for the NSCLC A549 cells.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

SEQUENCE LISTING

```
<160> NUMBER OF SEQ ID NOS: 57

<210> SEQ ID NO 1
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: along with the sulfur atom that is attached
```

```
        thereto is 3-mercaptopropionic acid, optionally substituted
        cysteine, or optionally substituted homocysteine
<220> FEATURE:
<221> NAME/KEY: MISC_FEATURE
<222> LOCATION: (1)..(7)
<223> OTHER INFORMATION: Forms cyclic structure via sulfur atoms and a
        linker -(CH2-Ar1-CH2)a-, where Ar1 is an optionally substituted
        aryl and a is 0 or 1
<220> FEATURE:
<221> NAME/KEY: MISC_FEATURE
<222> LOCATION: (3)..(3)
<223> OTHER INFORMATION: Arg, Dap, Dab, Orn, Lys, Dap(iPr), Dab(iPr),
        Orn(iPr), or Lys(iPr)
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (7)..(7)
<223> OTHER INFORMATION: along with the sulfur atom that is attached
        thereto is cysteine or homocysteine
<220> FEATURE:
<221> NAME/KEY: MISC_FEATURE
<222> LOCATION: (8)..(8)
<223> OTHER INFORMATION: Arg, Dap, Dab, Orn, Lys, Dap(iPr), Dab(iPr),
        Orn(iPr), Lys(iPr), D-Arg, D-Dap, D-Dab, D-Orn, D-Lys, D-Dap(iPr),
        D-Dab(iPr), D-Orn(iPr), D-Lys(iPr), or absent
<220> FEATURE:
<221> NAME/KEY: MISC_FEATURE
<222> LOCATION: (9)..(9)
<223> OTHER INFORMATION: Lys, Gly or absent, preferably X3 is Gly or
        absent
<220> FEATURE:
<221> NAME/KEY: MISC_FEATURE
<222> LOCATION: (10)..(10)
<223> OTHER INFORMATION: Lys, Phe, 2Nal, 1Nal, a D-isomer thereof, Gly
        or absent, preferably X4 is Phe, 2Nal, 1Nal, a D-isomer thereof,
        or absent
<220> FEATURE:
<221> NAME/KEY: MISC_FEATURE
<222> LOCATION: (11)..(11)
<223> OTHER INFORMATION: Lys, Gly or absent, preferably X5 is Gly or
        absent
<220> FEATURE:
<221> NAME/KEY: MISC_FEATURE
<222> LOCATION: (11)..(11)
<223> OTHER INFORMATION: terminated with -OR4 or -NHR5, where R4 is H or
        alkyl; and R5 is H, alkyl, optionally substituted aryl, optionally
        substituted aralkyl.

<400> SEQUENCE: 1

Asn Tyr Asn Arg Asn Gly Asn Asn Asn Asn Asn
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: along with the sulfur atom that is attached
        thereto is 3-mercaptopropionic acid, optionally substituted
        cysteine, or optionally substituted homocysteine
<220> FEATURE:
<221> NAME/KEY: MISC_FEATURE
<222> LOCATION: (1)..(1)
<223> OTHER INFORMATION: R1 is H or NHR3, R3 is H, C2-18 alkyl, C2-18
        acyl, optionally substituted C6-24 aryl, or a moiety of the
        formula -[C(=O)]a-[R1a]b-Ar1a, a and b is either 0 or 1, provided
```

```
        at least one of a or b is 1, R1a is alkylene and Ar1a is
        optionally
<220> FEATURE:
<221> NAME/KEY: MISC_FEATURE
<222> LOCATION: (1)..(7)
<223> OTHER INFORMATION: Forms cyclic structure via sulfur atoms and a
        linker -(CH2-Ar1-CH2)a-, where Ar1 is an optionally substituted
        aryl and a is 0 or 1
<220> FEATURE:
<221> NAME/KEY: MISC_FEATURE
<222> LOCATION: (3)..(3)
<223> OTHER INFORMATION: Arg, Dap, Dab, Orn, Lys, Dap(iPr), Dab(iPr),
        Orn(iPr), or Lys(iPr)
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (7)..(7)
<223> OTHER INFORMATION: along with the sulfur atom that is attached
        thereto is cysteine or homocysteine
<220> FEATURE:
<221> NAME/KEY: MISC_FEATURE
<222> LOCATION: (8)..(8)
<223> OTHER INFORMATION: Arg, Dap, Dab, Orn, Lys, Dap(iPr), Dab(iPr),
        Orn(iPr), Lys(iPr), D-Arg, D-Dap, D-Dab, D-Orn, D-Lys, D-Dap(iPr),
        D-Dab(iPr), D-Orn(iPr), D-Lys(iPr), or absent
<220> FEATURE:
<221> NAME/KEY: MISC_FEATURE
<222> LOCATION: (9)..(9)
<223> OTHER INFORMATION: Gly, Lys, Lys(acyl), or absent
<220> FEATURE:
<221> NAME/KEY: MISC_FEATURE
<222> LOCATION: (10)..(10)
<223> OTHER INFORMATION: Phe, 2Nal, 1Nal, or a (D)-isomer thereof, or
        absent
<220> FEATURE:
<221> NAME/KEY: MISC_FEATURE
<222> LOCATION: (11)..(11)
<223> OTHER INFORMATION: Gly or absent
<220> FEATURE:
<221> NAME/KEY: MISC_FEATURE
<222> LOCATION: (11)..(11)
<223> OTHER INFORMATION: terminated with OH or NHR4, wherein R4 is H,
        C1-18 alkyl, optionally substituted C6-24 aryl or optionally
        substituted aralkyl

<400> SEQUENCE: 2

Asn Tyr Asn Arg Asn Gly Asn Asn Asn Asn Asn
1               5                   10

<210> SEQ ID NO 3
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: 3-mercaptopropionic acid
<220> FEATURE:
<221> NAME/KEY: MISC_FEATURE
<222> LOCATION: (1)..(7)
<223> OTHER INFORMATION: cyclic structure is formed by a disulfide
        linkage between 3-mercaptopropionic acid and cysteine
<220> FEATURE:
<221> NAME/KEY: MISC_FEATURE
<222> LOCATION: (3)..(3)
<223> OTHER INFORMATION: side-chain functional group is protected with
        iPr
<220> FEATURE:
```

-continued

```
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (8)..(8)
<223> OTHER INFORMATION: side-chain functional group is protected with
      iPr
<220> FEATURE:
<221> NAME/KEY: MISC_FEATURE
<222> LOCATION: (9)..(9)
<223> OTHER INFORMATION: terminal amide group is substituted with ethyl
      group.

<400> SEQUENCE: 3

Asn Tyr Lys Arg Asn Gly Cys Lys Gly
1               5

<210> SEQ ID NO 4
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: 3-mercaptopropionic acid
<220> FEATURE:
<221> NAME/KEY: MISC_FEATURE
<222> LOCATION: (1)..(7)
<223> OTHER INFORMATION: cyclic structure is formed by a disulfide
      linkage between 3-mercaptopropionic acid and cysteine
<220> FEATURE:
<221> NAME/KEY: MISC_FEATURE
<222> LOCATION: (3)..(3)
<223> OTHER INFORMATION: side-chain functional group is protected with
      iPr
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (8)..(8)
<223> OTHER INFORMATION: side-chain functional group is substituted with
      iPr

<400> SEQUENCE: 4

Asn Tyr Lys Arg Asn Gly Cys Lys Gly
1               5

<210> SEQ ID NO 5
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: homocysteine
<220> FEATURE:
<221> NAME/KEY: MISC_FEATURE
<222> LOCATION: (1)..(1)
<223> OTHER INFORMATION: alpha-amino group substituted with acyl group
<220> FEATURE:
```

```
<221> NAME/KEY: MISC_FEATURE
<222> LOCATION: (1)..(7)
<223> OTHER INFORMATION: cyclic structure is formed by a disulfide
      linkage between homocysteine and cysteine
<220> FEATURE:
<221> NAME/KEY: MISC_FEATURE
<222> LOCATION: (3)..(3)
<223> OTHER INFORMATION: side-chain functional group is substituted with
      iPr
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (8)..(8)
<223> OTHER INFORMATION: side-chain functional group is substituted with
      iPr

<400> SEQUENCE: 5

Asn Tyr Lys Arg Asn Gly Cys Lys Gly
1               5

<210> SEQ ID NO 6
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: side-chain functional group is substituted with
      acyl group
<220> FEATURE:
<221> NAME/KEY: MISC_FEATURE
<222> LOCATION: (1)..(1)
<223> OTHER INFORMATION: homocysteine
<220> FEATURE:
<221> NAME/KEY: MISC_FEATURE
<222> LOCATION: (1)..(7)
<223> OTHER INFORMATION: cyclic structure is formed by a disulfide
      linkage between homocysteine and cysteine
<220> FEATURE:
<221> NAME/KEY: MISC_FEATURE
<222> LOCATION: (3)..(3)
<223> OTHER INFORMATION: side-chain functional group is substituted with
      iPr
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (8)..(8)
<223> OTHER INFORMATION: side-chain functional group is substituted with
      iPr
<220> FEATURE:
<221> NAME/KEY: MISC_FEATURE
<222> LOCATION: (9)..(9)
<223> OTHER INFORMATION: terminal amide group is substituted with ethyl
      group

<400> SEQUENCE: 6

Asn Tyr Lys Arg Asn Gly Cys Lys Gly
1               5
```

```
<210> SEQ ID NO 7
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: side-chain functional group is substituted with
      acy or benzoyl
<220> FEATURE:
<221> NAME/KEY: MISC_FEATURE
<222> LOCATION: (1)..(7)
<223> OTHER INFORMATION: Forms cyclic structure via sulfur atoms of
      cysteine groups and a linker -(CH2-Phe-CH2)-
<220> FEATURE:
<221> NAME/KEY: MISC_FEATURE
<222> LOCATION: (3)..(3)
<223> OTHER INFORMATION: side-chain functional group is substituted with
      iPr
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (8)..(8)
<223> OTHER INFORMATION: side-chain functional group is substituted with
      iPr

<400> SEQUENCE: 7

Asn Tyr Lys Arg Asn Gly Cys Lys Gly
1               5

<210> SEQ ID NO 8
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: cysteine or homocysteine
<220> FEATURE:
<221> NAME/KEY: MISC_FEATURE
<222> LOCATION: (1)..(1)
<223> OTHER INFORMATION: side-chain functional group is substituted with
      benzoyl
<220> FEATURE:
<221> NAME/KEY: MISC_FEATURE
<222> LOCATION: (1)..(7)
<223> OTHER INFORMATION: cyclic structure is formed by a disulfide
      linkage
<220> FEATURE:
<221> NAME/KEY: MISC_FEATURE
<222> LOCATION: (3)..(3)
<223> OTHER INFORMATION: side-chain functional group is substituted with
      iPr
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (7)..(7)
<223> OTHER INFORMATION: cysteine or homocysteine
<220> FEATURE:
```

```
<221> NAME/KEY: MISC_FEATURE
<222> LOCATION: (8)..(8)
<223> OTHER INFORMATION: alpha-amino group is substituted with iPr
<220> FEATURE:
<221> NAME/KEY: MISC_FEATURE
<222> LOCATION: (8)..(8)
<223> OTHER INFORMATION: side-chain functional group is substituted with
      iPr

<400> SEQUENCE: 8

Asn Tyr Lys Arg Asn Gly Asn Lys Gly
1               5

<210> SEQ ID NO 9
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: side-chain functional group is substituted with
      acyl
<220> FEATURE:
<221> NAME/KEY: MISC_FEATURE
<222> LOCATION: (1)..(1)
<223> OTHER INFORMATION: homocysteine
<220> FEATURE:
<221> NAME/KEY: MISC_FEATURE
<222> LOCATION: (1)..(7)
<223> OTHER INFORMATION: cyclic structure is formed by a disulfide
      linkage between homocysteine and cysteine
<220> FEATURE:
<221> NAME/KEY: MISC_FEATURE
<222> LOCATION: (3)..(3)
<223> OTHER INFORMATION: side-chain functional group is substituted with
      iPr
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (8)..(8)
<223> OTHER INFORMATION: side-chain functional group is substituted with
      iPr
<220> FEATURE:
<221> NAME/KEY: MISC_FEATURE
<222> LOCATION: (9)..(9)
<223> OTHER INFORMATION: terminal amide group is substituted with ethyl
      group.

<400> SEQUENCE: 9

Asn Tyr Lys Arg Asn Gly Cys Lys Gly
1               5

<210> SEQ ID NO 10
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: 3-mercaptopropionic acid
<220> FEATURE:
<221> NAME/KEY: MISC_FEATURE
<222> LOCATION: (1)..(7)
<223> OTHER INFORMATION: cyclic structure is formed by a disulfide
```

```
    linkage between 3-mercaptopropionic acid and cysteine
<220> FEATURE:
<221> NAME/KEY: MISC_FEATURE
<222> LOCATION: (3)..(3)
<223> OTHER INFORMATION: side-chain functional group is substituted with
      iPr
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (8)..(8)
<223> OTHER INFORMATION: side-chain functional group is substituted with
      iPr
<220> FEATURE:
<221> NAME/KEY: MISC_FEATURE
<222> LOCATION: (9)..(9)
<223> OTHER INFORMATION: side-chain functional group is substituted with
      acyl group
<220> FEATURE:
<221> NAME/KEY: MISC_FEATURE
<222> LOCATION: (9)..(9)
<223> OTHER INFORMATION: terminal amide group is substituted with ethyl
      group.

<400> SEQUENCE: 10

Asn Tyr Lys Arg Asn Gly Cys Lys Lys
1               5

<210> SEQ ID NO 11
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: side-chain functional group is substituted with
      benzoyl
<220> FEATURE:
<221> NAME/KEY: MISC_FEATURE
<222> LOCATION: (1)..(1)
<223> OTHER INFORMATION: homocysteine
<220> FEATURE:
<221> NAME/KEY: MISC_FEATURE
<222> LOCATION: (1)..(7)
<223> OTHER INFORMATION: cyclic structure is formed by a disulfide
      linkage between homocysteine and cysteine
<220> FEATURE:
<221> NAME/KEY: MISC_FEATURE
<222> LOCATION: (3)..(3)
<223> OTHER INFORMATION: side-chain functional group is substituted with
      iPr
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (8)..(8)
<223> OTHER INFORMATION: side-chain functional group is substituted with
      iPr

<400> SEQUENCE: 11

Asn Tyr Lys Arg Asn Gly Cys Lys Gly
1               5
```

```
<210> SEQ ID NO 12
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: 3-mercaptopropionic acid
<220> FEATURE:
<221> NAME/KEY: MISC_FEATURE
<222> LOCATION: (1)..(7)
<223> OTHER INFORMATION: cyclic structure is formed by a disulfide
      linkage between 3-mercaptopropionic acid and cysteine
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (10)..(10)
<223> OTHER INFORMATION: D-isomer

<400> SEQUENCE: 12

Asn Tyr Arg Arg Asn Gly Cys Arg Gly Phe Gly
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: 3-mercaptopropionic acid
<220> FEATURE:
<221> NAME/KEY: MISC_FEATURE
<222> LOCATION: (1)..(1)
<223> OTHER INFORMATION: side-chain functional group is substituted with
      Trt group
<220> FEATURE:
<221> NAME/KEY: MISC_FEATURE
<222> LOCATION: (2)..(2)
<223> OTHER INFORMATION: side-chain functional group is substituted with
      tBu group
<220> FEATURE:
<221> NAME/KEY: MISC_FEATURE
<222> LOCATION: (3)..(3)
<223> OTHER INFORMATION: side-chain functional group is substituted with
      Pbf group
<220> FEATURE:
<221> NAME/KEY: MISC_FEATURE
<222> LOCATION: (4)..(4)
<223> OTHER INFORMATION: side-chain functional group is substituted with
      Pbf group
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (7)..(7)
<223> OTHER INFORMATION: side-chain functional group is substituted with
      Trt group
```

```
<220> FEATURE:
<221> NAME/KEY: MISC_FEATURE
<222> LOCATION: (8)..(8)
<223> OTHER INFORMATION: side-chain functional group is substituted with
      Pbf group
<220> FEATURE:
<221> NAME/KEY: MISC_FEATURE
<222> LOCATION: (10)..(10)
<223> OTHER INFORMATION: D-isomer

<400> SEQUENCE: 13

Asn Thr Arg Arg Asn Gly Cys Arg Gly Phe Gly
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: 3-mercaptopropionic acid
<220> FEATURE:
<221> NAME/KEY: MISC_FEATURE
<222> LOCATION: (1)..(7)
<223> OTHER INFORMATION: cyclic structure is formed by a disulfide
      linkage between 3-mercaptopropionic acid and cysteine
<220> FEATURE:
<221> NAME/KEY: MISC_FEATURE
<222> LOCATION: (3)..(3)
<223> OTHER INFORMATION: alpha-amino group is substituted with iPr
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (10)..(10)
<223> OTHER INFORMATION: D-isomer

<400> SEQUENCE: 14

Asn Tyr Lys Arg Asn Gly Cys Arg Gly Phe Gly
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: 3-mercaptopropionic acid
<220> FEATURE:
<221> NAME/KEY: MISC_FEATURE
<222> LOCATION: (1)..(1)
<223> OTHER INFORMATION: side-chain functional group is substituted with
      Trt group
<220> FEATURE:
<221> NAME/KEY: MISC_FEATURE
<222> LOCATION: (2)..(2)
<223> OTHER INFORMATION: side-chain functional group is substituted with
      tBu group
<220> FEATURE:
<221> NAME/KEY: MISC_FEATURE
<222> LOCATION: (3)..(3)
<223> OTHER INFORMATION: side-chain functional group is substituted with
      iPr group
```

```
<220> FEATURE:
<221> NAME/KEY: MISC_FEATURE
<222> LOCATION: (4)..(4)
<223> OTHER INFORMATION: side-chain functional group is substituted with
      Pfb group
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (7)..(7)
<223> OTHER INFORMATION: side-chain functional group is substituted with
      Trt group
<220> FEATURE:
<221> NAME/KEY: MISC_FEATURE
<222> LOCATION: (8)..(8)
<223> OTHER INFORMATION: side-chain functional group is substituted with
      Pbf group
<220> FEATURE:
<221> NAME/KEY: MISC_FEATURE
<222> LOCATION: (10)..(10)
<223> OTHER INFORMATION: D-isomer

<400> SEQUENCE: 15

Asn Tyr Lys Arg Asn Gly Cys Arg Gly Phe Gly
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: 3-mercaptopropionic acid
<220> FEATURE:
<221> NAME/KEY: MISC_FEATURE
<222> LOCATION: (1)..(7)
<223> OTHER INFORMATION: cyclic structure is formed by a disulfide
      linkage between 3-mercaptopropionic acid and cysteine
<220> FEATURE:
<221> NAME/KEY: MISC_FEATURE
<222> LOCATION: (3)..(3)
<223> OTHER INFORMATION: side-chain functional group is substituted with
      iPr
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (8)..(8)
<223> OTHER INFORMATION: side-chain functional group is substituted with
      iPr
<220> FEATURE:
<221> NAME/KEY: MISC_FEATURE
<222> LOCATION: (10)..(10)
<223> OTHER INFORMATION: D-isomer

<400> SEQUENCE: 16

Asn Tyr Lys Arg Asn Gly Cys Lys Gly Phe Gly
1               5                   10

<210> SEQ ID NO 17
```

```
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: 3-mercaptopropionic acid
<220> FEATURE:
<221> NAME/KEY: MISC_FEATURE
<222> LOCATION: (1)..(1)
<223> OTHER INFORMATION: Thiol group protected with Trt group.
<220> FEATURE:
<221> NAME/KEY: MISC_FEATURE
<222> LOCATION: (2)..(2)
<223> OTHER INFORMATION: side-chain functional group is substituted with
     tBu group
<220> FEATURE:
<221> NAME/KEY: MISC_FEATURE
<222> LOCATION: (3)..(3)
<223> OTHER INFORMATION: side-chain functional group is substituted with
     iPr group
<220> FEATURE:
<221> NAME/KEY: MISC_FEATURE
<222> LOCATION: (4)..(4)
<223> OTHER INFORMATION: side-chain functional group is substituted with
     Pbf group
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (7)..(7)
<223> OTHER INFORMATION: side-chain functional group is substituted with
     Trt group
<220> FEATURE:
<221> NAME/KEY: MISC_FEATURE
<222> LOCATION: (8)..(8)
<223> OTHER INFORMATION: side-chain functional group is substituted with
     iPr group
<220> FEATURE:
<221> NAME/KEY: MISC_FEATURE
<222> LOCATION: (10)..(10)
<223> OTHER INFORMATION: D-isomer

<400> SEQUENCE: 17

Asn Tyr Lys Arg Asn Gly Cys Lys Gly Phe Gly
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: 3-mercaptopropionic acid
<220> FEATURE:
<221> NAME/KEY: MISC_FEATURE
<222> LOCATION: (1)..(7)
<223> OTHER INFORMATION: cyclic structure is formed by a disulfide
     linkage between 3-mercaptopropionic acid and cysteine
<220> FEATURE:
<221> NAME/KEY: MISC_FEATURE
<222> LOCATION: (3)..(3)
<223> OTHER INFORMATION: side-chain functional group is substituted with
     iPr group
<220> FEATURE:
<221> NAME/KEY: MISC_FEATURE
```

```
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (8)..(8)
<223> OTHER INFORMATION: D-isomer
<220> FEATURE:
<221> NAME/KEY: MISC_FEATURE
<222> LOCATION: (10)..(10)
<223> OTHER INFORMATION: D-isomer

<400> SEQUENCE: 18

Asn Tyr Lys Arg Asn Gly Cys Arg Gly Phe Gly
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: 3-mercaptopropionic acid
<220> FEATURE:
<221> NAME/KEY: MISC_FEATURE
<222> LOCATION: (1)..(1)
<223> OTHER INFORMATION: Thiol group protected by Trt group
<220> FEATURE:
<221> NAME/KEY: MISC_FEATURE
<222> LOCATION: (2)..(2)
<223> OTHER INFORMATION: side-chain functional group is substituted with
      tBu
<220> FEATURE:
<221> NAME/KEY: MISC_FEATURE
<222> LOCATION: (3)..(3)
<223> OTHER INFORMATION: side-chain functional group is substituted with
      iPr
<220> FEATURE:
<221> NAME/KEY: MISC_FEATURE
<222> LOCATION: (4)..(4)
<223> OTHER INFORMATION: side-chain functional group is substituted with
      Pbf
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (7)..(7)
<223> OTHER INFORMATION: side-chain functional group is substituted with
      Trt
<220> FEATURE:
<221> NAME/KEY: MISC_FEATURE
<222> LOCATION: (8)..(8)
<223> OTHER INFORMATION: side-chain functional group is substituted with
      Pbf
<220> FEATURE:
<221> NAME/KEY: MISC_FEATURE
<222> LOCATION: (8)..(8)
<223> OTHER INFORMATION: D-isomer
<220> FEATURE:
<221> NAME/KEY: MISC_FEATURE
<222> LOCATION: (10)..(10)
<223> OTHER INFORMATION: D-isomer

<400> SEQUENCE: 19
```

```
Asn Tyr Lys Arg Asn Gly Cys Arg Gly Phe Gly
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: 3-mercaptopropionic acid
<220> FEATURE:
<221> NAME/KEY: MISC_FEATURE
<222> LOCATION: (1)..(7)
<223> OTHER INFORMATION: cyclic structure is formed by a disulfide
      linkage between 3-mercaptopropionic acid and cysteine
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (10)..(10)
<223> OTHER INFORMATION: D-isomer

<400> SEQUENCE: 20

Asn Arg Tyr Arg Asn Gly Cys Arg Gly Phe Gly
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: 3-mercaptopropionic acid
<220> FEATURE:
<221> NAME/KEY: MISC_FEATURE
<222> LOCATION: (1)..(1)
<223> OTHER INFORMATION: Thiol group is substituted with Trt
<220> FEATURE:
<221> NAME/KEY: MISC_FEATURE
<222> LOCATION: (2)..(2)
<223> OTHER INFORMATION: side-chain functional group is substituted with
      Pbf
<220> FEATURE:
<221> NAME/KEY: MISC_FEATURE
<222> LOCATION: (3)..(3)
<223> OTHER INFORMATION: side-chain functional group is substituted with
      tBu
<220> FEATURE:
<221> NAME/KEY: MISC_FEATURE
<222> LOCATION: (4)..(4)
<223> OTHER INFORMATION: side-chain functional group is substituted with
      Pbf
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (7)..(7)
<223> OTHER INFORMATION: side-chain functional group is substituted with
      Trt
<220> FEATURE:
<221> NAME/KEY: MISC_FEATURE
<222> LOCATION: (8)..(8)
<223> OTHER INFORMATION: side-chain functional group is substituted with
      Pbf
<220> FEATURE:
<221> NAME/KEY: MISC_FEATURE
```

<222> LOCATION: (10)..(10)
<223> OTHER INFORMATION: D-isomer

<400> SEQUENCE: 21

Asn Arg Tyr Arg Asn Gly Cys Arg Gly Phe Gly
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: 3-mercaptopropionic acid
<220> FEATURE:
<221> NAME/KEY: MISC_FEATURE
<222> LOCATION: (1)..(1)
<223> OTHER INFORMATION: Thiol group is substituted with Trt
<220> FEATURE:
<221> NAME/KEY: MISC_FEATURE
<222> LOCATION: (2)..(2)
<223> OTHER INFORMATION: side-chain functional group is substituted with
     tBu
<220> FEATURE:
<221> NAME/KEY: MISC_FEATURE
<222> LOCATION: (3)..(3)
<223> OTHER INFORMATION: side-chain functional group is substituted with
     iPr and Boc
<220> FEATURE:
<221> NAME/KEY: MISC_FEATURE
<222> LOCATION: (4)..(4)
<223> OTHER INFORMATION: side-chain functional group is substituted with
     Pbf
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (7)..(7)
<223> OTHER INFORMATION: side-chain functional group is substituted with
     Trt
<220> FEATURE:
<221> NAME/KEY: MISC_FEATURE
<222> LOCATION: (8)..(8)
<223> OTHER INFORMATION: side-chain functional group is substituted with
     iPr and Boc
<220> FEATURE:
<221> NAME/KEY: MISC_FEATURE
<222> LOCATION: (10)..(10)
<223> OTHER INFORMATION: D-isomer

<400> SEQUENCE: 22

Asn Tyr Lys Arg Asn Gly Cys Lys Gly Phe Gly
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: side-chain functional group is protected with
     Trt
<220> FEATURE:

```
<221> NAME/KEY: MISC_FEATURE
<222> LOCATION: (2)..(2)
<223> OTHER INFORMATION: side-chain functional group is protected with
      tBu
<220> FEATURE:
<221> NAME/KEY: MISC_FEATURE
<222> LOCATION: (3)..(3)
<223> OTHER INFORMATION: side-chain functional group is substiuted with
      iPr and Boc
<220> FEATURE:
<221> NAME/KEY: MISC_FEATURE
<222> LOCATION: (4)..(4)
<223> OTHER INFORMATION: side-chain functional group is substiuted with
      Pbf
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (7)..(7)
<223> OTHER INFORMATION: side-chain functional group is protected with
      Trt
<220> FEATURE:
<221> NAME/KEY: MISC_FEATURE
<222> LOCATION: (8)..(8)
<223> OTHER INFORMATION: side-chain functional group is substituted with
      iPr and Boc
<220> FEATURE:
<221> NAME/KEY: MISC_FEATURE
<222> LOCATION: (10)..(10)
<223> OTHER INFORMATION: D-isomer

<400> SEQUENCE: 23

Asn Tyr Lys Arg Asn Gly Cys Lys Gly Phe Gly
1               5                   10

<210> SEQ ID NO 24
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: 3-mercaptopropionic acid
<220> FEATURE:
<221> NAME/KEY: MISC_FEATURE
<222> LOCATION: (1)..(7)
<223> OTHER INFORMATION: cyclic structure is formed by a disulfide
      linkage between 3-mercaptopropionic acid and cysteine
<220> FEATURE:
<221> NAME/KEY: MISC_FEATURE
<222> LOCATION: (3)..(3)
<223> OTHER INFORMATION: side-chain functional group is substituted with
      iPr
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (8)..(8)
<223> OTHER INFORMATION: side-chain functional group is substituted with
      iPr
<220> FEATURE:
<221> NAME/KEY: MISC_FEATURE
<222> LOCATION: (9)..(9)
```

```
<223> OTHER INFORMATION: terminal amide group is substituted with ethyl
      group.

<400> SEQUENCE: 24

Asn Tyr Lys Arg Asn Gly Cys Lys Gly
1               5

<210> SEQ ID NO 25
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: 3-mercaptopropionic acid
<220> FEATURE:
<221> NAME/KEY: MISC_FEATURE
<222> LOCATION: (1)..(1)
<223> OTHER INFORMATION: Thiol group is substituted with Trt
<220> FEATURE:
<221> NAME/KEY: MISC_FEATURE
<222> LOCATION: (2)..(2)
<223> OTHER INFORMATION: side-chain functional group is substituted with
      tBu
<220> FEATURE:
<221> NAME/KEY: MISC_FEATURE
<222> LOCATION: (3)..(3)
<223> OTHER INFORMATION: side-chain functional group is substituted with
      iPr and Boc
<220> FEATURE:
<221> NAME/KEY: MISC_FEATURE
<222> LOCATION: (4)..(4)
<223> OTHER INFORMATION: side-chain functional group is substituted with
      Pbf
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (7)..(7)
<223> OTHER INFORMATION: side-chain functional group is substituted with
      Trt
<220> FEATURE:
<221> NAME/KEY: MISC_FEATURE
<222> LOCATION: (8)..(8)
<223> OTHER INFORMATION: side-chain functional group is substituted with
      iPr and Boc

<400> SEQUENCE: 25

Asn Tyr Lys Arg Asn Gly Cys Lys Gly
1               5

<210> SEQ ID NO 26
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: 3-mercaptopropionic acid
<220> FEATURE:
<221> NAME/KEY: MISC_FEATURE
<222> LOCATION: (1)..(7)
<223> OTHER INFORMATION: cyclic structure is formed by a disulfide
      linkage between 3-mercaptopropionic acid and cysteine
<220> FEATURE:
```

```
<221> NAME/KEY: MISC_FEATURE
<222> LOCATION: (3)..(3)
<223> OTHER INFORMATION: alpha-amino group is substituted with iPr
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (8)..(8)
<223> OTHER INFORMATION: alpha-amino group is substituted with iPr
<220> FEATURE:
<221> NAME/KEY: MISC_FEATURE
<222> LOCATION: (10)..(10)
<223> OTHER INFORMATION: 2NaI

<400> SEQUENCE: 26

Asn Tyr Lys Arg Asn Gly Cys Lys Asx Asn Gly
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: 3-mercaptopropionic acid
<220> FEATURE:
<221> NAME/KEY: MISC_FEATURE
<222> LOCATION: (1)..(1)
<223> OTHER INFORMATION: Thiol group is substituted with Trt
<220> FEATURE:
<221> NAME/KEY: MISC_FEATURE
<222> LOCATION: (2)..(2)
<223> OTHER INFORMATION: side-chain functional group is substituted with
      tBu
<220> FEATURE:
<221> NAME/KEY: MISC_FEATURE
<222> LOCATION: (3)..(3)
<223> OTHER INFORMATION: side-chain functional group is substituted with
      iPr
<220> FEATURE:
<221> NAME/KEY: MISC_FEATURE
<222> LOCATION: (4)..(4)
<223> OTHER INFORMATION: side-chain functional group is substituted with
      Pbf
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (7)..(7)
<223> OTHER INFORMATION: side-chain functional group is substituted with
      Trt
<220> FEATURE:
<221> NAME/KEY: MISC_FEATURE
<222> LOCATION: (8)..(8)
<223> OTHER INFORMATION: side-chain functional group is substituted with
      iPr
<220> FEATURE:
<221> NAME/KEY: MISC_FEATURE
<222> LOCATION: (10)..(10)
<223> OTHER INFORMATION: 2NaI

<400> SEQUENCE: 27
```

Asn Tyr Lys Arg Asn Gly Cys Lys Gly Asn Gly
1               5                   10

```
<210> SEQ ID NO 28
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: homocysteine
<220> FEATURE:
<221> NAME/KEY: MISC_FEATURE
<222> LOCATION: (1)..(1)
<223> OTHER INFORMATION: side-chain functional group is substituted with
      acyl group
<220> FEATURE:
<221> NAME/KEY: MISC_FEATURE
<222> LOCATION: (1)..(7)
<223> OTHER INFORMATION: cyclic structure is formed by a disulfide
      linkage between homocysteine and cysteine
<220> FEATURE:
<221> NAME/KEY: MISC_FEATURE
<222> LOCATION: (3)..(3)
<223> OTHER INFORMATION: side-chain functional group is substituted with
      iPr
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (8)..(8)
<223> OTHER INFORMATION: side-chain functional group is substituted with
      iPr
<220> FEATURE:
<221> NAME/KEY: MISC_FEATURE
<222> LOCATION: (10)..(10)
<223> OTHER INFORMATION: D-isomer

<400> SEQUENCE: 28
```

Asn Tyr Lys Arg Asn Gly Cys Lys Gly Phe Gly
1               5                   10

```
<210> SEQ ID NO 29
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: homocysteine
<220> FEATURE:
<221> NAME/KEY: MISC_FEATURE
<222> LOCATION: (1)..(1)
<223> OTHER INFORMATION: Thiol group is substituted with Trt
<220> FEATURE:
<221> NAME/KEY: MISC_FEATURE
<222> LOCATION: (2)..(2)
<223> OTHER INFORMATION: side-chain functional group is substituted with
      tBu
<220> FEATURE:
<221> NAME/KEY: MISC_FEATURE
<222> LOCATION: (3)..(3)
<223> OTHER INFORMATION: side-chain functional group is substituted with
      iPr
<220> FEATURE:
```

<221> NAME/KEY: MISC_FEATURE
<222> LOCATION: (4)..(4)
<223> OTHER INFORMATION: side-chain functional group is substituted with
      Pbf
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (7)..(7)
<223> OTHER INFORMATION: Thiol group is substituted with Trt
<220> FEATURE:
<221> NAME/KEY: MISC_FEATURE
<222> LOCATION: (8)..(8)
<223> OTHER INFORMATION: side-chain functional group is substituted with
      iPr
<220> FEATURE:
<221> NAME/KEY: MISC_FEATURE
<222> LOCATION: (10)..(10)
<223> OTHER INFORMATION: D-isomer

<400> SEQUENCE: 29

Asn Tyr Lys Arg Asn Gly Cys Lys Gly Phe Gly
1               5                   10

<210> SEQ ID NO 30
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: homocysteine
<220> FEATURE:
<221> NAME/KEY: MISC_FEATURE
<222> LOCATION: (1)..(1)
<223> OTHER INFORMATION: side-chain functional group is substituted with
      acyl group
<220> FEATURE:
<221> NAME/KEY: MISC_FEATURE
<222> LOCATION: (1)..(7)
<223> OTHER INFORMATION: cyclic structure is formed by a disulfide
      linkage between homocysteine and cysteine
<220> FEATURE:
<221> NAME/KEY: MISC_FEATURE
<222> LOCATION: (3)..(3)
<223> OTHER INFORMATION: side-chain functional group is substituted with
      iPr
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (8)..(8)
<223> OTHER INFORMATION: side-chain functional group is substituted with
      iPr

<400> SEQUENCE: 30

Asn Tyr Lys Arg Asn Gly Cys Lys Gly
1               5

<210> SEQ ID NO 31
<211> LENGTH: 9

```
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: homocysteine
<220> FEATURE:
<221> NAME/KEY: MISC_FEATURE
<222> LOCATION: (1)..(1)
<223> OTHER INFORMATION: Thiol group is protected with Trt
<220> FEATURE:
<221> NAME/KEY: MISC_FEATURE
<222> LOCATION: (2)..(2)
<223> OTHER INFORMATION: side-chain functional group is substituted with
      tBu
<220> FEATURE:
<221> NAME/KEY: MISC_FEATURE
<222> LOCATION: (3)..(3)
<223> OTHER INFORMATION: side-chain functional group is substituted with
      iPr
<220> FEATURE:
<221> NAME/KEY: MISC_FEATURE
<222> LOCATION: (4)..(4)
<223> OTHER INFORMATION: side-chain functional group is substituted with
      Pbf
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (7)..(7)
<223> OTHER INFORMATION: Thiol group is protected with Trt
<220> FEATURE:
<221> NAME/KEY: MISC_FEATURE
<222> LOCATION: (8)..(8)
<223> OTHER INFORMATION: side-chain functional group is substituted with
      iPr

<400> SEQUENCE: 31

Asn Tyr Lys Arg Asn Gly Cys Lys Gly
1               5

<210> SEQ ID NO 32
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: homocysteine
<220> FEATURE:
<221> NAME/KEY: MISC_FEATURE
<222> LOCATION: (1)..(1)
<223> OTHER INFORMATION: side-chain functional group is substituted with
      benzoyl group
<220> FEATURE:
<221> NAME/KEY: MISC_FEATURE
<222> LOCATION: (1)..(7)
<223> OTHER INFORMATION: cyclic structure is formed by a disulfide
      linkage between homocysteine and cysteine
<220> FEATURE:
<221> NAME/KEY: MISC_FEATURE
<222> LOCATION: (3)..(3)
<223> OTHER INFORMATION: side-chain functional group is substituted with
      iPr
<220> FEATURE:
<221> NAME/KEY: MISC_FEATURE
<222> LOCATION: (4)..(4)
```

```
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (8)..(8)
<223> OTHER INFORMATION: side-chain functional group is substituted with
      iPr

<400> SEQUENCE: 32

Asn Tyr Lys Arg Asn Gly Cys Lys Gly
1               5

<210> SEQ ID NO 33
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: homocysteine
<220> FEATURE:
<221> NAME/KEY: MISC_FEATURE
<222> LOCATION: (1)..(1)
<223> OTHER INFORMATION: Thiol group is protected with Trt
<220> FEATURE:
<221> NAME/KEY: MISC_FEATURE
<222> LOCATION: (2)..(2)
<223> OTHER INFORMATION: side-chain functional group is protected with
      iPr
<220> FEATURE:
<221> NAME/KEY: MISC_FEATURE
<222> LOCATION: (3)..(3)
<223> OTHER INFORMATION: side-chain functional group is protected with
      iPr and Boc
<220> FEATURE:
<221> NAME/KEY: MISC_FEATURE
<222> LOCATION: (4)..(4)
<223> OTHER INFORMATION: side-chain functional group is protected with
      Pbf
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (7)..(7)
<223> OTHER INFORMATION: side-chain functional group is protected with
      Trt
<220> FEATURE:
<221> NAME/KEY: MISC_FEATURE
<222> LOCATION: (8)..(8)
<223> OTHER INFORMATION: side-chain functional group is substituted with
      iPr and Boc

<400> SEQUENCE: 33

Asn Tyr Lys Arg Asn Gly Cys Lys Gly
1               5

<210> SEQ ID NO 34
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
```

```
<222> LOCATION: (1)..(1)
<223> OTHER INFORMATION: amino-group is substituted with benzoyl
<220> FEATURE:
<221> NAME/KEY: MISC_FEATURE
<222> LOCATION: (1)..(7)
<223> OTHER INFORMATION: cyclic structure is formed by a disulfide
      linkage between cysteine and homocysteine
<220> FEATURE:
<221> NAME/KEY: MISC_FEATURE
<222> LOCATION: (3)..(3)
<223> OTHER INFORMATION: side-chain functional group is substituted with
      iPr
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (7)..(7)
<223> OTHER INFORMATION: homocysteine
<220> FEATURE:
<221> NAME/KEY: MISC_FEATURE
<222> LOCATION: (8)..(8)
<223> OTHER INFORMATION: side-chain functional group is substituted with
      iPr

<400> SEQUENCE: 34

Cys Tyr Lys Arg Asn Gly Asn Lys Gly
1               5

<210> SEQ ID NO 35
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: side-chain functional group is substituted with
      Trt
<220> FEATURE:
<221> NAME/KEY: MISC_FEATURE
<222> LOCATION: (2)..(2)
<223> OTHER INFORMATION: side-chain functional group is substituted with
      tBu
<220> FEATURE:
<221> NAME/KEY: MISC_FEATURE
<222> LOCATION: (3)..(3)
<223> OTHER INFORMATION: side-chain functional group is substituted with
      iPr and Boc
<220> FEATURE:
<221> NAME/KEY: MISC_FEATURE
<222> LOCATION: (4)..(4)
<223> OTHER INFORMATION: side-chain functional group is substituted with
      iPr and Pbf
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (7)..(7)
<223> OTHER INFORMATION: homocysteine
<220> FEATURE:
<221> NAME/KEY: MISC_FEATURE
<222> LOCATION: (7)..(7)
<223> OTHER INFORMATION: side-chain functional group is substituted with
      Trt
```

```
<220> FEATURE:
<221> NAME/KEY: MISC_FEATURE
<222> LOCATION: (8)..(8)
<223> OTHER INFORMATION: side-chain functional group is substituted with
      iPr and Boc

<400> SEQUENCE: 35

Cys Tyr Lys Arg Asn Gly Asn Lys Gly
1               5

<210> SEQ ID NO 36
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: side-chain functional group is substituted with
      benzoyl
<220> FEATURE:
<221> NAME/KEY: MISC_FEATURE
<222> LOCATION: (1)..(7)
<223> OTHER INFORMATION: cyclic structure is formed by a disulfide
      linkage between two cysteine groups
<220> FEATURE:
<221> NAME/KEY: MISC_FEATURE
<222> LOCATION: (3)..(3)
<223> OTHER INFORMATION: side-chain functional group is substituted with
      iPr
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (8)..(8)
<223> OTHER INFORMATION: side-chain functional group is substituted with
      iPr

<400> SEQUENCE: 36

Cys Tyr Lys Arg Asn Gly Cys Lys Gly
1               5

<210> SEQ ID NO 37
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: side-chain functional group is substituted with
      Trt
<220> FEATURE:
<221> NAME/KEY: MISC_FEATURE
<222> LOCATION: (2)..(2)
<223> OTHER INFORMATION: side-chain functional group is substituted with
      tBu
<220> FEATURE:
<221> NAME/KEY: MISC_FEATURE
<222> LOCATION: (3)..(3)
<223> OTHER INFORMATION: side-chain functional group is substituted with
      iPr and Boc
<220> FEATURE:
<221> NAME/KEY: MISC_FEATURE
<222> LOCATION: (4)..(4)
<223> OTHER INFORMATION: side-chain functional group is substituted with
      Pbf
```

```
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (7)..(7)
<223> OTHER INFORMATION: side-chain functional group is substituted with
     Trt
<220> FEATURE:
<221> NAME/KEY: MISC_FEATURE
<222> LOCATION: (8)..(8)
<223> OTHER INFORMATION: side-chain functional group is substituted with
     iPr and Boc

<400> SEQUENCE: 37

Cys Tyr Lys Arg Asn Gly Cys Lys Gly
1               5

<210> SEQ ID NO 38
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: homocysteine
<220> FEATURE:
<221> NAME/KEY: MISC_FEATURE
<222> LOCATION: (1)..(1)
<223> OTHER INFORMATION: side-chain functional group is substituted with
     benzoyl
<220> FEATURE:
<221> NAME/KEY: MISC_FEATURE
<222> LOCATION: (1)..(7)
<223> OTHER INFORMATION: cyclic structure is formed by a disulfide
     linkage between homocysteine and cysteine
<220> FEATURE:
<221> NAME/KEY: MISC_FEATURE
<222> LOCATION: (3)..(3)
<223> OTHER INFORMATION: side-chain functional group is substituted with
     iPr
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (8)..(8)
<223> OTHER INFORMATION: side-chain functional group is substituted with
     iPr

<400> SEQUENCE: 38

Asn Tyr Lys Arg Asn Gly Cys Lys Gly
1               5

<210> SEQ ID NO 39
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
```

```
<223> OTHER INFORMATION: homocysteine
<220> FEATURE:
<221> NAME/KEY: MISC_FEATURE
<222> LOCATION: (1)..(1)
<223> OTHER INFORMATION: side-chain functional group is substituted with
      Trt
<220> FEATURE:
<221> NAME/KEY: MISC_FEATURE
<222> LOCATION: (2)..(2)
<223> OTHER INFORMATION: side-chain functional group is substituted with
      tBu
<220> FEATURE:
<221> NAME/KEY: MISC_FEATURE
<222> LOCATION: (3)..(3)
<223> OTHER INFORMATION: side-chain functional group is substituted with
      iPr and Boc
<220> FEATURE:
<221> NAME/KEY: MISC_FEATURE
<222> LOCATION: (4)..(4)
<223> OTHER INFORMATION: side-chain functional group is substituted with
      Pbf
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (7)..(7)
<223> OTHER INFORMATION: side-chain functional group is substituted with
      Trt
<220> FEATURE:
<221> NAME/KEY: MISC_FEATURE
<222> LOCATION: (8)..(8)
<223> OTHER INFORMATION: side-chain functional group is substituted with
      iPr and Boc

<400> SEQUENCE: 39

Asn Tyr Lys Arg Asn Gly Cys Lys Gly
1               5

<210> SEQ ID NO 40
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: homocysteine
<220> FEATURE:
<221> NAME/KEY: MISC_FEATURE
<222> LOCATION: (1)..(1)
<223> OTHER INFORMATION: side-chain functional group is substituted with
      phenylacetyl
      group
<220> FEATURE:
<221> NAME/KEY: MISC_FEATURE
<222> LOCATION: (1)..(7)
<223> OTHER INFORMATION: cyclic structure is formed by a disulfide
      linkage between homocysteine and cysteine
<220> FEATURE:
<221> NAME/KEY: MISC_FEATURE
<222> LOCATION: (3)..(3)
<223> OTHER INFORMATION: side-chain functional group is substituted with
      iPr
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
```

```
<223> OTHER INFORMATION: 2NaI
<220> FEATURE:
<221> NAME/KEY: MISC_FEATURE
<222> LOCATION: (8)..(8)
<223> OTHER INFORMATION: side-chain functional group is substituted with
      iPr

<400> SEQUENCE: 40

Asn Tyr Lys Arg Asn Gly Cys Lys Gly
1               5

<210> SEQ ID NO 41
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: homocysteine
<220> FEATURE:
<221> NAME/KEY: MISC_FEATURE
<222> LOCATION: (1)..(1)
<223> OTHER INFORMATION: side-chain functional group is substituted with
      Trt
<220> FEATURE:
<221> NAME/KEY: MISC_FEATURE
<222> LOCATION: (2)..(2)
<223> OTHER INFORMATION: side-chain functional group is substituted with
      tBu
<220> FEATURE:
<221> NAME/KEY: MISC_FEATURE
<222> LOCATION: (3)..(3)
<223> OTHER INFORMATION: side-chain functional group is substituted with
      iPr and Boc
<220> FEATURE:
<221> NAME/KEY: MISC_FEATURE
<222> LOCATION: (4)..(4)
<223> OTHER INFORMATION: side-chain functional group is substituted with
      Pbf
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (7)..(7)
<223> OTHER INFORMATION: side-chain functional group is substituted with
      Trt
<220> FEATURE:
<221> NAME/KEY: MISC_FEATURE
<222> LOCATION: (8)..(8)
<223> OTHER INFORMATION: side-chain functional group is substituted with
      iPr and Boc

<400> SEQUENCE: 41

Asn Tyr Lys Arg Asn Gly Cys Lys Gly
1               5

<210> SEQ ID NO 42
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: homocysteine
<220> FEATURE:
```

```
<221> NAME/KEY: MISC_FEATURE
<222> LOCATION: (1)..(1)
<223> OTHER INFORMATION: side-chain functional group is substituted with
      Acyl group
<220> FEATURE:
<221> NAME/KEY: MISC_FEATURE
<222> LOCATION: (1)..(7)
<223> OTHER INFORMATION: cyclic structure is formed by a disulfide
      linkage between homocysteine and cysteine
<220> FEATURE:
<221> NAME/KEY: MISC_FEATURE
<222> LOCATION: (3)..(3)
<223> OTHER INFORMATION: side-chain functional group is substituted with
      iPr
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (8)..(8)
<223> OTHER INFORMATION: side-chain functional group is substituted with
      iPr
<220> FEATURE:
<221> NAME/KEY: MISC_FEATURE
<222> LOCATION: (9)..(9)
<223> OTHER INFORMATION: terminal amide group is substituted with ethyl
      group.

<400> SEQUENCE: 42

Asn Tyr Lys Arg Asn Gly Cys Lys Gly
1               5

<210> SEQ ID NO 43
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: homocysteine
<220> FEATURE:
<221> NAME/KEY: MISC_FEATURE
<222> LOCATION: (1)..(1)
<223> OTHER INFORMATION: side-chain functional group is substituted with
      Trt
<220> FEATURE:
<221> NAME/KEY: MISC_FEATURE
<222> LOCATION: (2)..(2)
<223> OTHER INFORMATION: side-chain functional group is substituted with
      tBu
<220> FEATURE:
<221> NAME/KEY: MISC_FEATURE
<222> LOCATION: (3)..(3)
<223> OTHER INFORMATION: side-chain functional group is substituted with
      iPr and Boc
<220> FEATURE:
<221> NAME/KEY: MISC_FEATURE
<222> LOCATION: (4)..(4)
<223> OTHER INFORMATION: side-chain functional group is substituted with
      Pbf
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
```

```
<222> LOCATION: (7)..(7)
<223> OTHER INFORMATION: side-chain functional group is substituted with
      Trt
<220> FEATURE:
<221> NAME/KEY: MISC_FEATURE
<222> LOCATION: (8)..(8)
<223> OTHER INFORMATION: side-chain functional group is substituted with
      iPr and Boc

<400> SEQUENCE: 43

Asn Tyr Lys Arg Asn Gly Cys Lys Gly
1               5

<210> SEQ ID NO 44
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: 3-mercaptopropionic acid
<220> FEATURE:
<221> NAME/KEY: MISC_FEATURE
<222> LOCATION: (1)..(7)
<223> OTHER INFORMATION: cyclic structure is formed by a disulfide
      linkage between 3-mercaptopropionic acid and cysteine
<220> FEATURE:
<221> NAME/KEY: MISC_FEATURE
<222> LOCATION: (3)..(3)
<223> OTHER INFORMATION: side-chain functional group is substituted with
      iPr
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (8)..(8)
<223> OTHER INFORMATION: side-chain functional group is substituted with
      iPr
<220> FEATURE:
<221> NAME/KEY: MISC_FEATURE
<222> LOCATION: (9)..(9)
<223> OTHER INFORMATION: side-chain functional group is substituted with
      Ac

<400> SEQUENCE: 44

Asn Tyr Lys Arg Asn Gly Cys Lys Lys
1               5

<210> SEQ ID NO 45
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: 3-mercaptopropionic acid
<220> FEATURE:
<221> NAME/KEY: MISC_FEATURE
<222> LOCATION: (1)..(1)
<223> OTHER INFORMATION: side-chain functional group is substituted with
      Trt
<220> FEATURE:
<221> NAME/KEY: MISC_FEATURE
<222> LOCATION: (2)..(2)
<223> OTHER INFORMATION: side-chain functional group is substituted with
```

```
      tBu
<220> FEATURE:
<221> NAME/KEY: MISC_FEATURE
<222> LOCATION: (3)..(3)
<223> OTHER INFORMATION: side-chain functional group is substituted with
      iPr and Boc
<220> FEATURE:
<221> NAME/KEY: MISC_FEATURE
<222> LOCATION: (4)..(4)
<223> OTHER INFORMATION: side-chain functional group is substituted with
      Pbf
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (7)..(7)
<223> OTHER INFORMATION: side-chain functional group is substituted with
      Trt
<220> FEATURE:
<221> NAME/KEY: MISC_FEATURE
<222> LOCATION: (8)..(8)
<223> OTHER INFORMATION: side-chain functional group is substituted with
      iPr and Boc
<220> FEATURE:
<221> NAME/KEY: MISC_FEATURE
<222> LOCATION: (9)..(9)
<223> OTHER INFORMATION: side-chain functional group is substituted with
      Ac

<400> SEQUENCE: 45

Asn Tyr Lys Arg Asn Gly Cys Lys Lys
1               5

<210> SEQ ID NO 46
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: 3-mercaptopropionic acid
<220> FEATURE:
<221> NAME/KEY: MISC_FEATURE
<222> LOCATION: (1)..(7)
<223> OTHER INFORMATION: cyclic structure is formed by a disulfide
      linkage between 3-mercaptopropionic acid and cysteine
<220> FEATURE:
<221> NAME/KEY: MISC_FEATURE
<222> LOCATION: (3)..(3)
<223> OTHER INFORMATION: side-chain functional group is substituted with
      iPr
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (8)..(8)
<223> OTHER INFORMATION: side-chain functional group is substituted with
      iPr
<220> FEATURE:
<221> NAME/KEY: MISC_FEATURE
<222> LOCATION: (9)..(9)
<223> OTHER INFORMATION: side-chain functional group is substituted with
      lauroyl
```

```
<400> SEQUENCE: 46

Asn Tyr Lys Arg Asn Gly Cys Lys Lys
1               5

<210> SEQ ID NO 47
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: side-chain functional group is substituted with
      Trt
<220> FEATURE:
<221> NAME/KEY: MISC_FEATURE
<222> LOCATION: (2)..(2)
<223> OTHER INFORMATION: side-chain functional group is substituted with
      tBu
<220> FEATURE:
<221> NAME/KEY: MISC_FEATURE
<222> LOCATION: (3)..(3)
<223> OTHER INFORMATION: side-chain functional group is substituted with
      iPr and Boc
<220> FEATURE:
<221> NAME/KEY: MISC_FEATURE
<222> LOCATION: (4)..(4)
<223> OTHER INFORMATION: side-chain functional group is substituted with
      Pbf
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (7)..(7)
<223> OTHER INFORMATION: side-chain functional group is substituted with
      Trt
<220> FEATURE:
<221> NAME/KEY: MISC_FEATURE
<222> LOCATION: (8)..(8)
<223> OTHER INFORMATION: side-chain functional group is substituted with
      iPr and Boc
<220> FEATURE:
<221> NAME/KEY: MISC_FEATURE
<222> LOCATION: (9)..(9)
<223> OTHER INFORMATION: side-chain functional group is substituted with
      iPr and dde

<400> SEQUENCE: 47

Asn Tyr Lys Arg Asn Gly Cys Lys Lys
1               5

<210> SEQ ID NO 48
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: 3-mercaptopropionic acid
<220> FEATURE:
<221> NAME/KEY: MISC_FEATURE
<222> LOCATION: (1)..(7)
<223> OTHER INFORMATION: cyclic structure is formed by a disulfide
      linkage between homocysteine and cysteine
<220> FEATURE:
```

-continued

```
<221> NAME/KEY: MISC_FEATURE
<222> LOCATION: (3)..(3)
<223> OTHER INFORMATION: side-chain functional group is substituted with
      iPr
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (8)..(8)
<223> OTHER INFORMATION: side-chain functional group is substituted with
      iPr
<220> FEATURE:
<221> NAME/KEY: MISC_FEATURE
<222> LOCATION: (9)..(9)
<223> OTHER INFORMATION: side-chain functional group is substituted with
      palmitoyl.

<400> SEQUENCE: 48

Asn Tyr Lys Arg Asn Gly Cys Lys Lys
1               5

<210> SEQ ID NO 49
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: side-chain functional group is substituted with
      Trt
<220> FEATURE:
<221> NAME/KEY: MISC_FEATURE
<222> LOCATION: (1)..(1)
<223> OTHER INFORMATION: 3-mercaptopropionic acid
<220> FEATURE:
<221> NAME/KEY: MISC_FEATURE
<222> LOCATION: (2)..(2)
<223> OTHER INFORMATION: side-chain functional group is substituted with
      tBu
<220> FEATURE:
<221> NAME/KEY: MISC_FEATURE
<222> LOCATION: (3)..(3)
<223> OTHER INFORMATION: side-chain functional group is substituted with
      iPr and Boc
<220> FEATURE:
<221> NAME/KEY: MISC_FEATURE
<222> LOCATION: (4)..(4)
<223> OTHER INFORMATION: side-chain functional group is substituted with
      Pbf
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (7)..(7)
<223> OTHER INFORMATION: side-chain functional group is substituted with
      Trt
<220> FEATURE:
<221> NAME/KEY: MISC_FEATURE
<222> LOCATION: (8)..(8)
<223> OTHER INFORMATION: side-chain functional group is substituted with
      iPr and Boc
<220> FEATURE:
<221> NAME/KEY: MISC_FEATURE
```

```
<222> LOCATION: (9)..(9)
<223> OTHER INFORMATION: side-chain functional group is substituted with
      dde

<400> SEQUENCE: 49

Asn Tyr Lys Arg Asn Gly Cys Lys Lys
1               5

<210> SEQ ID NO 50
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: alpha-amino group is substituted with benzoyl
<220> FEATURE:
<221> NAME/KEY: MISC_FEATURE
<222> LOCATION: (1)..(7)
<223> OTHER INFORMATION: cyclic structure is formed by a disulfide
      linkage between two cysteine groups
<220> FEATURE:
<221> NAME/KEY: MISC_FEATURE
<222> LOCATION: (3)..(3)
<223> OTHER INFORMATION: side-chain functional group is substituted with
      iPr
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (8)..(8)
<223> OTHER INFORMATION: side-chain functional group is substituted with
      iPr

<400> SEQUENCE: 50

Cys Tyr Lys Arg Asn Gly Cys Lys Gly
1               5

<210> SEQ ID NO 51
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: side-chain functional group is substituted with
      Trt
<220> FEATURE:
<221> NAME/KEY: MISC_FEATURE
<222> LOCATION: (2)..(2)
<223> OTHER INFORMATION: side-chain functional group is substituted with
      tBu
<220> FEATURE:
<221> NAME/KEY: MISC_FEATURE
<222> LOCATION: (3)..(3)
<223> OTHER INFORMATION: side-chain functional group is substituted with
      iPr and Boc
<220> FEATURE:
<221> NAME/KEY: MISC_FEATURE
<222> LOCATION: (4)..(4)
<223> OTHER INFORMATION: side-chain functional group is substituted with
      Pbf
<220> FEATURE:
<221> NAME/KEY: MISC_FEATURE
<222> LOCATION: (4)..(4)
```

```
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (7)..(7)
<223> OTHER INFORMATION: side-chain functional group is substituted with
      Trt
<220> FEATURE:
<221> NAME/KEY: MISC_FEATURE
<222> LOCATION: (8)..(8)
<223> OTHER INFORMATION: side-chain functional group is substituted with
      iPr and Boc

<400> SEQUENCE: 51

Cys Tyr Lys Arg Asn Gly Cys Lys Gly
1               5

<210> SEQ ID NO 52
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: 3-mercaptopropionic acid
<220> FEATURE:
<221> NAME/KEY: MISC_FEATURE
<222> LOCATION: (1)..(7)
<223> OTHER INFORMATION: cyclic structure is formed by a disulfide
      linkage between 3-mercaptopropionic acid and cysteine
<220> FEATURE:
<221> NAME/KEY: MISC_FEATURE
<222> LOCATION: (3)..(3)
<223> OTHER INFORMATION: side-chain functional group is substituted with
      iPr
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (8)..(8)
<223> OTHER INFORMATION: side-chain functional group is substituted with
      iPr
<220> FEATURE:
<221> NAME/KEY: MISC_FEATURE
<222> LOCATION: (9)..(9)
<223> OTHER INFORMATION: terminal amide group is substituted with ethyl
      group.

<400> SEQUENCE: 52

Asn Tyr Lys Arg Asn Gly Cys Lys Gly
1               5

<210> SEQ ID NO 53
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: 3-mercaptopropionic acid
<220> FEATURE:
<221> NAME/KEY: MISC_FEATURE
```

```
<222> LOCATION: (1)..(1)
<223> OTHER INFORMATION: side-chain functional group is substituted with
      Trt
<220> FEATURE:
<221> NAME/KEY: MISC_FEATURE
<222> LOCATION: (2)..(2)
<223> OTHER INFORMATION: side-chain functional group is substituted with
      tBu
<220> FEATURE:
<221> NAME/KEY: MISC_FEATURE
<222> LOCATION: (3)..(3)
<223> OTHER INFORMATION: side-chain functional group is substituted with
      iPr and Boc
<220> FEATURE:
<221> NAME/KEY: MISC_FEATURE
<222> LOCATION: (4)..(4)
<223> OTHER INFORMATION: side-chain functional group is substituted with
      Pbf
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (7)..(7)
<223> OTHER INFORMATION: side-chain functional group is substituted with
      Trt
<220> FEATURE:
<221> NAME/KEY: MISC_FEATURE
<222> LOCATION: (8)..(8)
<223> OTHER INFORMATION: side-chain functional group is substituted with
      iPr and Boc

<400> SEQUENCE: 53

Asn Tyr Lys Arg Asn Gly Cys Lys Gly
1               5

<210> SEQ ID NO 54
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: alpha-amino group is substituted with acyl
<220> FEATURE:
<221> NAME/KEY: MISC_FEATURE
<222> LOCATION: (1)..(7)
<223> OTHER INFORMATION: cyclic structure is formed by a disulfide
      linkage between two cysteine groups.
<220> FEATURE:
<221> NAME/KEY: MISC_FEATURE
<222> LOCATION: (3)..(3)
<223> OTHER INFORMATION: side-chain functional group is substituted with
      iPr
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (8)..(8)
<223> OTHER INFORMATION: side-chain functional group is substituted with
      iPr

<400> SEQUENCE: 54
```

Cys Tyr Lys Arg Asn Gly Cys Lys Gly
1               5

<210> SEQ ID NO 55
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: side-chain functional group is substituted with
      Trt
<220> FEATURE:
<221> NAME/KEY: MISC_FEATURE
<222> LOCATION: (2)..(2)
<223> OTHER INFORMATION: side-chain functional group is substituted with
      tBu
<220> FEATURE:
<221> NAME/KEY: MISC_FEATURE
<222> LOCATION: (3)..(3)
<223> OTHER INFORMATION: side-chain functional group is substituted with
      iPr and Boc
<220> FEATURE:
<221> NAME/KEY: MISC_FEATURE
<222> LOCATION: (4)..(4)
<223> OTHER INFORMATION: side-chain functional group is substituted with
      Pbf
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (7)..(7)
<223> OTHER INFORMATION: side-chain functional group is substituted with
      Trt
<220> FEATURE:
<221> NAME/KEY: MISC_FEATURE
<222> LOCATION: (8)..(8)
<223> OTHER INFORMATION: side-chain functional group is substituted with
      iPr and Boc

<400> SEQUENCE: 55

Cys Tyr Lys Arg Asn Gly Cys Lys Gly
1               5

<210> SEQ ID NO 56
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: alpha amino-group is substituted with acyl
<220> FEATURE:
<221> NAME/KEY: MISC_FEATURE
<222> LOCATION: (1)..(7)
<223> OTHER INFORMATION: cyclic structure is formed by a disulfide
      linkage between two cysteine groups
<220> FEATURE:
<221> NAME/KEY: MISC_FEATURE
<222> LOCATION: (3)..(3)
<223> OTHER INFORMATION: side-chain functional group is substituted with
      iPr
<220> FEATURE:
<221> NAME/KEY: MISC_FEATURE
<222> LOCATION: (4)..(4)
<223> OTHER INFORMATION: D-isomer

```
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (8)..(8)
<223> OTHER INFORMATION: side-chain functional group is substituted with
      iPr

<400> SEQUENCE: 56

Cys Tyr Lys Arg Asn Gly Cys Lys Gly
1               5

<210> SEQ ID NO 57
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: side-chain functional group is substituted with
      Trt
<220> FEATURE:
<221> NAME/KEY: MISC_FEATURE
<222> LOCATION: (2)..(2)
<223> OTHER INFORMATION: side-chain functional group is substituted with
      tBu
<220> FEATURE:
<221> NAME/KEY: MISC_FEATURE
<222> LOCATION: (3)..(3)
<223> OTHER INFORMATION: side-chain functional group is substituted with
      iPr and Boc
<220> FEATURE:
<221> NAME/KEY: MISC_FEATURE
<222> LOCATION: (4)..(4)
<223> OTHER INFORMATION: side-chain functional group is substituted with
      Pbf
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (7)..(7)
<223> OTHER INFORMATION: side-chain functional group is substituted with
      Trt
<220> FEATURE:
<221> NAME/KEY: MISC_FEATURE
<222> LOCATION: (8)..(8)
<223> OTHER INFORMATION: side-chain functional group is substituted with
      iPr and Boc

<400> SEQUENCE: 57

Cys Tyr Lys Arg Asn Gly Cys Lys Gly
1               5
```

What is claimed is:

1. A composition comprising (i) a therapeutic agent comprising a chemotherapeutic agent, an antiviral agent, or a combination thereof, and (ii) a CXCR4 antagonist of the formula:

(SEQ ID NO:1)

I

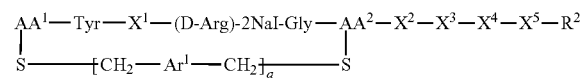

or a pharmaceutically acceptable salt thereof, wherein
a is 0 or 1;
$AA^1$ along with the sulfur atom that is attached thereto is 3-mercaptopropionic acid, optionally substituted cysteine, or optionally substituted homocysteine;
$AA^2$ along with the sulfur atom that is attached thereto is cysteine or homocysteine;
$Ar^1$ is an optionally substituted aryl;
$X^1$ is Arg, Dap, Dab, Orn, Lys, Dap(iPr), Dab(iPr), Orn(iPr), or Lys(iPr);
$X^2$ is Arg, Dap, Dab, Orn, Lys, Dap(iPr), Dab(iPr), Orn(iPr), Lys(iPr), D-Arg, D-Dap, D-Dab, D-Orn, D-Lys, D-Dap(iPr), D-Dab(iPr), D-Orn(iPr), D-Lys(iPr), or absent;
$X^3$ is Gly or absent;
$X^4$ is Phe, 2Nal, 1Nal, the D-isomer thereof, or absent;
$X^5$ is Gly or absent;
$R^2$ is —$OR^4$ or —$NHR^5$;
$R^4$ is H or alkyl; and
$R^5$ is H, alkyl, optionally substituted aryl, optionally substituted aralkyl.

2. The composition of claim 1, wherein said chemotherapeutic agent is selected from the group consisting of Altretamine; Asparaginase; Bleomycin; Busulfan; Carboplatin; Carmustine; Chlorambucil; Cisplatin; Cladribine; Cyclophosphamide; Cytarabine; Dacarbazine; Diethylstilbestrol; Ethinyl; estradiol; Etoposide; Mitomycin; Mitotane; Mitoxantrone; Paclitaxel; Pentastatin; Pipobroman; Plicamycin; Prednisone; Procarbazine; Streptozocin; Tamoxifen; Teniposide; Vinblastine; Vincristine; and a combination thereof.

3. The composition of claim 1, wherein said chemotherapeutic agent is an antibody selected from the group consisting of pembrolizumab, tremelimumab, ipilimumab, nivolumab, pidilizumab, durvalumab, atezolimab, trastuzumab, bevacizumab, cetuximab, panitumumab, rituximab, alemtuzumab, ofatumumab, gemtuzumab, brentuximab and a combination thereof.

4. The composition according to claim 1, wherein the CXCR4 antagonist is of the formula:

(SEQ ID NO:2)

IA

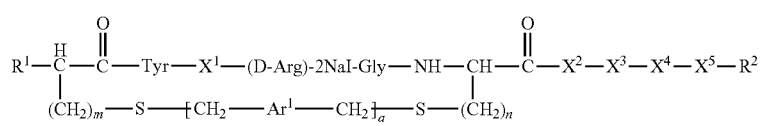

or a pharmaceutically acceptable salt thereof, wherein:
a is an integer 0 or 1;
m and n are independently 1 or 2;
$R^1$ is H or $NHR^3$, wherein $R^3$ is H, alkyl, acyl, optionally substituted aryl, optionally substituted aralkyl, —C(=O)—$Ar^a$, wherein $Ar^a$ is optionally substituted aryl; and
$Ar^1$, $X^2$, $X^3$, $X^4$, $X^5$ and $R^2$ are those defined in claim 1.

5. The composition according to claim 4, wherein a=1 and $Ar^1$ is an optionally substituted phenyl.

6. The composition according to claim 1, wherein (i) $X^2$ is a (D)-isomer or absent or (ii) $X^4$ is a (D)-isomer or absent.

7. The composition according to claim 4, wherein $R^1$ is H and m=1.

8. The composition according to claim 4, wherein $R^1$ is Ac-NH and m=2.

9. The composition according to claim 4, wherein $R^2$ is —NH(Et), and $X^4$ and $X^5$ are absent.

10. The composition according to claim 1, wherein the CXCR4 antagonist is selected from the group consisting of:
cyclo[Mpa-Tyr-Arg-(D-Arg)-2Nal-Gly-Cys]-Arg-Gly-(D-Phe)-Gly-$NH_2$;
cyclo[Mpa-Tyr-Lys(iPr)-(D-Arg)-2Nal-Gly-Cys]-Arg-Gly-(D-Phe)-Gly-$NH_2$;
cyclo[Mpa-Tyr-Lys(iPr)-(D-Arg)-2Nal-Gly-Cys]-Lys(iPr)-Gly-(D-Phe)-Gly-$NH_2$;
cyclo[Mpa-Tyr-Lys(iPr)-(D-Arg)-2Nal-Gly-Cys]-(D-Arg)-Gly-(D-Phe)-Gly-$NH_2$;
cyclo[Mpa-Arg-Tyr-Arg-2Nal-Gly-Cys]-Arg-Gly-(D-Phe)-Gly-$NH_2$;
cyclo[Mpa-Tyr-Lys(iPr)-(D-Arg)-2Nal-Gly-Cys]-Lys(iPr)-Gly-(D-Phe)-Gly-NH(Et);
cyclo[Mpa-Tyr-Lys(iPr)-(D-Arg)-2Nal-Gly-Cys]-Lys(iPr)-Gly-NH(Et);
cyclo[Mpa-Tyr-Lys(iPr)-(D-Arg)-2Nal-Gly-Cys]-Lys(iPr)-Gly-2Nal-Gly-$NH_2$;
Ac-cyclo[hCys-Tyr-Lys(iPr)-(D-Arg)-2Nal-Gly-Cys]-Lys(iPr)-Gly-(D-Phe)-Gly-$NH_2$;
Ac-cyclo[hCys-Tyr-Lys(iPr)-(D-Arg)-2Nal-Gly-Cys]-Lys(iPr)-Gly-$NH_2$;
Benzoylcyclo[hCys-Tyr-Lys(iPr)-(D-Arg)-2Nal-Gly-Cys]-Lys(iPr)-Gly-$NH_2$;
Benzoyl-cyclo[Cys-Tyr-Lys(iPr)-(D-Arg)-2Nal-Gly-hCys]-Lys(iPr)-Gly-$NH_2$;
Benzoyl-cyclo[hCys-Tyr-Lys(iPr)-(D-Arg)-2Nal-Gly-Cys]-Lys(iPr)-Gly-NH(Et);
Phenylacetyl-cyclo[hCys-Tyr-Lys(iPr)-(D-Arg)-2Nal-Gly-Cys]-Lys(iPr)-Gly-$NH_2$;
Ac-cyclo[hCys-Tyr-Lys(iPr)-(D-Arg)-2Nal-Gly-Cys]-Lys(iPr)-Gly-NH(Et);
cyclo[Mpa-Tyr-Lys(iPr)-(D-Arg)-2Nal-Gly-Cys]-Lys(iPr)-Lys(Ac)-NH(Et);

cyclo[Mpa-Tyr-Lys(iPr)-(D-Arg)-2Nal-Gly-Cys]-Lys(iPr)-Lys(lauroyl)-NH(Et);

cyclo[Mpa-Tyr-Lys(iPr)-(D-Arg)-2Nal-Gly-Cys]-Lys(iPr)-Lys(palmitoyl)-NH(Et);

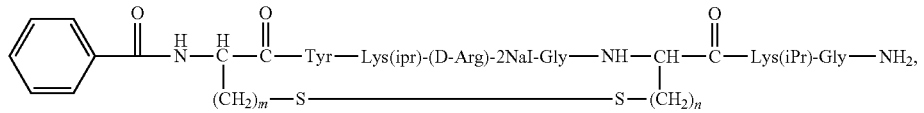

wherein each of m and n is independently 1 or 2;

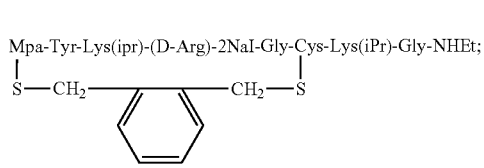

and

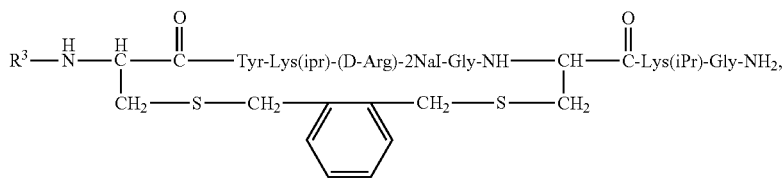

wherein $R^3$ is an alkyl or an acyl.

11. The composition according to claim 4, wherein m=1 or 2, n=1 or 2, and $R^1$ is $NHR^3$.

12. A method treating a subject suffering from a cancer selected from the group consisting of breast cancer, pancreatic cancer, melanoma, prostate cancer, kidney cancer, neuroblastoma, non-Hodgkin's lymphoma, lung cancer, ovarian cancer, colorectal cancer, multiple myeloma, glioblastoma multiforme, and chronic lymphocytic leukemia, said method comprising administering to a subject in need of such a treatment a therapeutically effective amount of a composition according to claim 1, wherein said therapeutic agent is a chemotherapeutic agent.

13. The method of claim 12, wherein said chemotherapeutic agent is a biological chemotherapeutic agent.

14. The method of claim 13, wherein said biological chemotherapeutic agent comprises an antibody selective to said anticancer.

15. The method of claim 13, wherein said biological chemotherapeutic agent comprises an immune checkpoint inhibitor.

16. The method of claim 13, wherein said biological chemotherapeutic agent is selected from the group consisting of PD-1 antibody, PD-L1 antibody, anti(α)-CTLA-4, pembrolizumab, atezolizumab, bevacizumab, and durvalumab.

* * * * *